(12) United States Patent
Miller et al.

(10) Patent No.: US 9,339,325 B2
(45) Date of Patent: *May 17, 2016

(54) SYSTEM AND METHOD FOR ASSESSING LESIONS IN TISSUE

(71) Applicant: St. Jude Medical, Atrial Fibrillation Division, Inc., St. Paul, MN (US)

(72) Inventors: Stephan P. Miller, Vadnais Heights, MN (US); Don Curtis Deno, Andover, MN (US); Saurav Paul, Minneapolis, MN (US); Liane R. Teplitsky, Manhattan Beach, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 37 days.

This patent is subject to a terminal disclaimer.

(21) Appl. No.: 13/850,060

(22) Filed: Mar. 25, 2013

(65) Prior Publication Data

US 2013/0226169 A1 Aug. 29, 2013

Related U.S. Application Data

(63) Continuation of application No. 12/622,488, filed on Nov. 20, 2009, now Pat. No. 8,403,925, which is a continuation-in-part of application No. 12/253,637, filed on Oct. 17, 2008, now Pat. No. 8,449,535, which (Continued)

(51) Int. Cl.
*A61B 18/12* (2006.01)
*A61B 18/00* (2006.01)
(Continued)

(52) U.S. Cl.
CPC ......... *A61B 18/1233* (2013.01); *A61B 18/1492* (2013.01); *A61B 18/14* (2013.01);
(Continued)

(58) Field of Classification Search
CPC ............... A61B 18/1223; A61B 18/14; A61B 18/1492; A61B 2018/00178; A61B 2018/00648; A61B 2018/00773; A61B 2018/00875; A61B 2018/00904; A61B 2019/465
USPC .......................................... 606/34
See application file for complete search history.

(56) References Cited

U.S. PATENT DOCUMENTS 2,184,511 A 12/1939 Bagno et al.
3,316,896 A 5/1967 Thomasset
(Continued)

FOREIGN PATENT DOCUMENTS

EP 1472976 11/2004
EP 1586281 4/2009
(Continued)

OTHER PUBLICATIONS

Supplementary European Search Report issued in EP Patent Application No. 11842330.0 (Jan. 20, 2014).
(Continued)

*Primary Examiner* — Michael Peffley
*Assistant Examiner* — Daniel Fowler
(74) *Attorney, Agent, or Firm* — Dykema Gossett PLLC

(57) ABSTRACT

A method and system for assessing lesion formation in tissue is provided. The system includes an electronic control unit (ECU). The ECU is configured to acquire values for first and second components of a complex impedance between the electrode and the tissue, and to calculate an index responsive to the first and second values. The ECU is further configured to process the ECI to assess lesion formation in the tissue.

19 Claims, 39 Drawing Sheets

Related U.S. Application Data is a continuation-in-part of application No. 12/095,688, filed as application No. PCT/US2006/061714 on Dec. 6, 2006.

(60) Provisional application No. 60/748,234, filed on Dec. 6, 2005, provisional application No. 61/177,876, filed on May 13, 2009.

(51) Int. Cl.
*A61B 18/14* (2006.01)
*A61B 19/00* (2006.01)

(52) U.S. Cl.
CPC .............. *A61B2018/00178* (2013.01); *A61B 2018/00773* (2013.01); *A61B 2018/00875* (2013.01); *A61B 2019/465* (2013.01)

(56) References Cited

U.S. PATENT DOCUMENTS

| | | | |
|---|---|---|---|
| 3,949,736 A | 4/1976 | Vrana et al. |
| 4,641,649 A | 2/1987 | Walinsky et al. |
| 5,230,349 A | 7/1993 | Langberg |
| 5,257,635 A | 11/1993 | Langberg |
| 5,297,549 A | 3/1994 | Beatty et al. |
| 5,311,866 A | 5/1994 | Kagan et al. |
| 5,341,807 A | 8/1994 | Nardella |
| 5,366,896 A | 11/1994 | Margrey et al. |
| 5,423,808 A | 6/1995 | Edwards et al. |
| 5,429,131 A | 7/1995 | Scheinman |
| 5,447,529 A | 9/1995 | Marchlinski et al. |
| 5,546,940 A | 8/1996 | Panescu et al. |
| 5,562,721 A | 10/1996 | Marchlinski et al. |
| 5,582,609 A | 12/1996 | Swanson et al. |
| 5,588,432 A | 12/1996 | Crowley et al. |
| 5,630,034 A | 5/1997 | Oikawa et al. |
| 5,657,755 A | 8/1997 | Desai |
| 5,659,624 A | 8/1997 | Fazzari et al. |
| 5,673,704 A | 10/1997 | Marchlinski et al. |
| 5,688,267 A | 11/1997 | Panescu et al. |
| 5,697,377 A | 12/1997 | Wittkampf |
| 5,702,386 A | 12/1997 | Stern et al. |
| 5,718,241 A | 2/1998 | Ben-Haim et al. |
| 5,722,402 A | 3/1998 | Swanson |
| 5,730,127 A | 3/1998 | Avitall |
| 5,759,159 A | 6/1998 | Masreliez |
| 5,782,900 A | 7/1998 | de la Rama |
| 5,800,350 A | 9/1998 | Coppleson |
| 5,810,742 A | 9/1998 | Pearlman |
| 5,814,043 A | 9/1998 | Shapeton |
| 5,836,943 A * | 11/1998 | Miller, III ................. 606/34 |
| 5,836,990 A | 11/1998 | Li |
| 5,837,001 A | 11/1998 | Mackey |
| 5,846,238 A | 12/1998 | Jackson et al. |
| 5,904,709 A | 5/1999 | Arndt |
| 5,944,022 A | 8/1999 | Nardella et al. |
| 5,954,665 A | 9/1999 | Ben-Haim |
| 6,001,093 A | 12/1999 | Swanson et al. |
| 6,019,757 A | 2/2000 | Scheldrup |
| 6,026,323 A | 2/2000 | Skladnev |
| 6,035,341 A | 3/2000 | Nunally et al. |
| 6,063,078 A | 5/2000 | Wittkampf |
| 6,129,669 A | 10/2000 | Panescu et al. |
| 6,171,304 B1 | 1/2001 | Netherly |
| 6,179,824 B1 | 1/2001 | Eggers et al. |
| 6,206,874 B1 | 3/2001 | Ubby et al. |
| 6,217,574 B1 | 4/2001 | Webster et al. |
| 6,217,576 B1 | 4/2001 | Tu |
| 6,221,070 B1 | 4/2001 | Tu et al. |
| 6,226,542 B1 | 5/2001 | Reisfeld |
| 6,233,476 B1 | 5/2001 | Strommer et al. |
| 6,246,896 B1 | 6/2001 | Dumoulin et al. |
| 6,256,540 B1 | 7/2001 | Panescu et al. |
| 6,322,558 B1 | 11/2001 | Taylor et al. |
| 6,337,994 B1 | 1/2002 | Stoianovici et al. |
| 6,391,024 B1 | 5/2002 | Sun et al. |
| 6,423,057 B1 | 7/2002 | He et al. |
| 6,427,089 B1 | 7/2002 | Knowlton |
| 6,443,894 B1 | 9/2002 | Sumanaweera et al. |
| 6,445,952 B1 | 9/2002 | Manrodt et al. |
| 6,456,864 B1 | 9/2002 | Swanson et al. |
| 6,471,693 B1 | 10/2002 | Carroll et al. |
| 6,475,215 B1 | 11/2002 | Tanrisever |
| 6,490,474 B1 | 12/2002 | Willis et al. |
| 6,498,944 B1 | 12/2002 | Ben-Haim et al. |
| 6,507,751 B2 | 1/2003 | Blume et al. |
| 6,511,478 B1 | 1/2003 | Burnside et al. |
| 6,558,382 B2 | 5/2003 | Jahns et al. |
| 6,569,160 B1 | 5/2003 | Goldin et al. |
| 6,573,704 B2 | 6/2003 | Mirov |
| 6,575,969 B1 | 6/2003 | Rittman et al. |
| 6,605,082 B2 | 8/2003 | Hareyama et al. |
| 6,652,518 B2 | 11/2003 | Wellman et al. |
| 6,663,622 B1 | 12/2003 | Foley et al. |
| 6,683,280 B1 | 1/2004 | Wofford et al. |
| 6,690,963 B2 | 2/2004 | Ben-Haim et al. |
| 6,696,844 B2 | 2/2004 | Wong et al. |
| 6,712,074 B2 | 3/2004 | Edwards et al. |
| 6,743,225 B2 | 6/2004 | Sanchez et al. |
| 6,755,790 B2 | 6/2004 | Stewart et al. |
| 6,780,182 B2 | 8/2004 | Bowman et al. |
| 6,788,967 B2 | 9/2004 | Ben-Haim et al. |
| 6,813,515 B2 | 11/2004 | Hashimshony |
| 6,840,938 B1 | 1/2005 | Morley et al. |
| 6,917,834 B2 | 7/2005 | Koblish et al. |
| 6,918,876 B1 | 7/2005 | Kamiyama |
| 6,926,669 B1 | 8/2005 | Stewart |
| 6,936,047 B2 | 8/2005 | Nasab et al. |
| 6,950,689 B1 | 9/2005 | Willis et al. |
| 6,964,867 B2 | 11/2005 | Downs |
| 6,965,795 B2 | 11/2005 | Rock |
| 6,993,384 B2 | 1/2006 | Bradley et al. |
| 7,041,096 B2 | 5/2006 | Malis et al. |
| 7,106,043 B1 | 9/2006 | Da Silva |
| 7,197,354 B2 | 3/2007 | Sobe |
| 7,248,032 B1 | 7/2007 | Hular |
| 7,263,395 B2 | 8/2007 | Chan et al. |
| 7,263,397 B2 | 8/2007 | Hauck et al. |
| 7,386,339 B2 | 6/2008 | Strommer et al. |
| 7,497,858 B2 | 3/2009 | Chapelon et al. |
| 7,499,745 B2 | 3/2009 | Littrup |
| 7,536,218 B2 | 5/2009 | Govari et al. |
| 7,565,613 B2 | 7/2009 | Forney |
| 7,610,078 B2 | 10/2009 | Willis |
| 7,633,502 B2 | 12/2009 | Willis et al. |
| 7,671,871 B2 | 3/2010 | Gonsalves |
| 7,776,034 B2 | 8/2010 | Kampa |
| 7,819,870 B2 | 10/2010 | Thao et al. |
| 7,865,236 B2 | 1/2011 | Cory |
| 7,904,174 B2 | 3/2011 | Hammill et al. |
| 7,953,495 B2 | 5/2011 | Sommer et al. |
| 8,075,498 B2 | 12/2011 | Leo et al. |
| 2001/0034501 A1 | 10/2001 | Tom |
| 2001/0039413 A1 | 11/2001 | Bowe |
| 2001/0047129 A1 | 11/2001 | Hall |
| 2001/0051774 A1 | 12/2001 | Littrup et al. |
| 2002/0022836 A1 | 2/2002 | Goble et al. |
| 2002/0049375 A1 | 4/2002 | Strommer et al. |
| 2002/0068931 A1 | 6/2002 | Wong et al. |
| 2002/0072686 A1 | 6/2002 | Hoey et al. |
| 2002/0077627 A1 * | 6/2002 | Johnson et al. ............. 606/41 |
| 2002/0120188 A1 | 8/2002 | Brock et al. |
| 2002/0123749 A1 | 9/2002 | Jain |
| 2002/0177847 A1 | 11/2002 | Long |
| 2003/0004587 A1 | 1/2003 | Raymond et al. |
| 2003/0028183 A1 | 2/2003 | Sanchez et al. |
| 2003/0045871 A1 | 3/2003 | Jain et al. |
| 2003/0060696 A1 | 3/2003 | Skladnev et al. |
| 2003/0065364 A1 | 4/2003 | Wellman |
| 2003/0093067 A1 | 5/2003 | Panescu |
| 2003/0093069 A1 | 5/2003 | Panescu |
| 2003/0100823 A1 | 5/2003 | Kipke et al. |
| 2003/0109871 A1 | 6/2003 | Johnson et al. |

(56) References Cited

U.S. PATENT DOCUMENTS

| | | |
|---|---|---|
| 2003/0130711 A1 | 7/2003 | Pearson et al. |
| 2003/0187430 A1 | 10/2003 | Vorisek |
| 2004/0006337 A1* | 1/2004 | Nasab et al. ............... 606/41 |
| 2004/0030258 A1 | 2/2004 | Williams et al. |
| 2004/0044292 A1 | 3/2004 | Yasushi et al. |
| 2004/0078036 A1* | 4/2004 | Keidar ............... 606/41 |
| 2004/0078058 A1 | 4/2004 | Holmstrom et al. |
| 2004/0082946 A1 | 4/2004 | Malis et al. |
| 2004/0087975 A1 | 5/2004 | Lucatero et al. |
| 2004/0097806 A1 | 5/2004 | Hunter |
| 2004/0147920 A1 | 7/2004 | Keidar |
| 2004/0181165 A1 | 9/2004 | Hoey et al. |
| 2004/0243018 A1 | 12/2004 | Organ |
| 2004/0243181 A1 | 12/2004 | Conrad et al. |
| 2004/0267252 A1 | 12/2004 | Washington et al. |
| 2005/0010263 A1 | 1/2005 | Schauerte |
| 2005/0054944 A1 | 3/2005 | Nakada et al. |
| 2005/0065507 A1 | 3/2005 | Hartley |
| 2005/0222554 A1 | 10/2005 | Wallace et al. |
| 2006/0015033 A1 | 1/2006 | Blakley et al. |
| 2006/0085049 A1 | 4/2006 | Cory et al. |
| 2006/0173251 A1 | 8/2006 | Govari |
| 2006/0200049 A1 | 9/2006 | Leo et al. |
| 2006/0235286 A1 | 10/2006 | Stone |
| 2007/0016006 A1 | 1/2007 | Shachar |
| 2007/0055142 A1 | 3/2007 | Webler |
| 2007/0073179 A1 | 3/2007 | Afonso et al. |
| 2007/0083193 A1 | 4/2007 | Werneth et al. |
| 2007/0100332 A1 | 5/2007 | Paul et al. |
| 2007/0106289 A1 | 5/2007 | O'Sullivan |
| 2007/0123764 A1 | 5/2007 | Thao et al. |
| 2007/0161915 A1 | 7/2007 | Desai |
| 2007/0225558 A1 | 9/2007 | Hauck |
| 2007/0225593 A1 | 9/2007 | Porath |
| 2007/0244479 A1 | 10/2007 | Beatty et al. |
| 2007/0255162 A1 | 11/2007 | Abboud et al. |
| 2008/0091193 A1 | 4/2008 | Kauphusman |
| 2008/0097220 A1 | 4/2008 | Lieber et al. |
| 2008/0097422 A1 | 4/2008 | Edwards et al. |
| 2008/0132890 A1 | 6/2008 | Woloszko |
| 2008/0183071 A1 | 7/2008 | Strommer et al. |
| 2008/0183189 A1 | 7/2008 | Teichman et al. |
| 2008/0234564 A1 | 9/2008 | Beatty et al. |
| 2008/0249536 A1 | 10/2008 | Stahler |
| 2008/0275465 A1 | 11/2008 | Paul et al. |
| 2008/0288023 A1 | 11/2008 | John |
| 2008/0288038 A1 | 11/2008 | Paul et al. |
| 2008/0300589 A1 | 12/2008 | Paul et al. |
| 2008/0312713 A1 | 12/2008 | Wilfey |
| 2009/0012533 A1 | 1/2009 | Barbagli |
| 2009/0036794 A1 | 2/2009 | Stubhaug et al. |
| 2009/0163904 A1 | 6/2009 | Miller et al. |
| 2009/0171235 A1 | 7/2009 | Schneider et al. |
| 2009/0171345 A1 | 7/2009 | Miller et al. |
| 2009/0177111 A1 | 7/2009 | Miller et al. |
| 2009/0247942 A1 | 10/2009 | Kirschenman |
| 2009/0247943 A1 | 10/2009 | Kirschenman |
| 2009/0247944 A1 | 10/2009 | Kirschenman |
| 2009/0247993 A1 | 10/2009 | Kirschenman et al. |
| 2009/0248042 A1 | 10/2009 | Kirschenman |
| 2009/0275827 A1 | 11/2009 | Aiken et al. |
| 2009/0276002 A1 | 11/2009 | Sommer |
| 2009/0306655 A1 | 12/2009 | Stangenes |
| 2010/0069921 A1 | 3/2010 | Miller et al. |
| 2010/0168550 A1 | 7/2010 | Byrd et al. |
| 2010/0168735 A1 | 7/2010 | Deno et al. |
| 2010/0191089 A1 | 7/2010 | Stebler et al. |
| 2010/0256558 A1 | 10/2010 | Olson et al. |
| 2010/0274239 A1 | 10/2010 | Paul |
| 2010/0298823 A1 | 11/2010 | Cao et al. |
| 2011/0015569 A1 | 1/2011 | Kirschenman |
| 2011/0118727 A1 | 5/2011 | Fish et al. |
| 2011/0313311 A1 | 12/2011 | Gaw |
| 2011/0313417 A1 | 12/2011 | De La Rama et al. |
| 2012/0158011 A1 | 6/2012 | Sandhu |

FOREIGN PATENT DOCUMENTS

| | | |
|---|---|---|
| JP | H08511440 | 12/1996 |
| JP | 3585491 | 11/2004 |
| JP | 2005279256 | 10/2005 |
| WO | 9846149 | 10/1998 |
| WO | WO-98/46149 | 10/1998 |
| WO | WO-00/78239 | 12/2000 |
| WO | 2007/067628 | 6/2007 |
| WO | 2007/067938 | 6/2007 |
| WO | WO-2007/067941 | 6/2007 |
| WO | WO-2009/065140 | 5/2009 |
| WO | WO-2009/085457 | 7/2009 |
| WO | 2009/120982 | 10/2009 |
| WO | 2011/123669 | 10/2011 |

OTHER PUBLICATIONS

, "International Search Report & Written Opinion", PCT/US2011/047235, Dec. 14, 2011.

, "International Search Report and Written Opinion of the International Searching Authority", PCT/US2006/061714, Sep. 22, 2008.

Avitall, Boaz et al., "The Effects of Electrode-Tissue Contact on Radiofrequency Lesion Generation", PACE, vol. 20, Dec. 1997, 2899-2910.

Chakraborty, D. P. , "ROC curves predicted by a model of visual search", Institute of Physics Publishing, Phys. Med. Biol. 51, 2006, 3463-3482.

Cho, Sungbo et al., "Design of electrode array for impedance measurement of lesions in arteries", Physiol. Meas. 26 S19-S26, doi: 10.1088/0967-3334/26/2/002, 2005.

Dumas, John H. et al., "Myocardial electrical impedance as a predictor of the quality of RF-induced linear lesions", Physiological Measurement, vol. 29, 2008, Abstract only.

Fenici, R. R. et al., "Biomagnetically localizable multipurpose catheter and method for MCG guided intracardiac electrophysiology, biopsy and ablation of cardiac arrhythmias", International Journal of Cardiac Imaging 7, 1991, 207-215.

Gales, Rosemary et al., "Use of bioelectrical impedance analysis to assess body composition of seals", Marine Mammal Science, vol. 10, Issue 1, Abstract, Aug. 26, 2006.

Gao, Xin et al., "Computer-Assisted Quantative Evaluation of Therapeutic Responses for Lymphoma Using Serial PET/CT Imaging", NIH Public Access, Acad Radiol. 17(4), Apr. 2010, 1-21.

He, Ding S. et al., "Assessment of Myocardial Lesion Size during In Vitro Radio Frequency Catheter Ablation", IEEE Transactions on Biomedical Engineering, vol. 50, No. 6, Jun. 2003, 768-776.

Himel, Herman D. , "Development of a metric to assess completeness of lesions produced by radiofrequency ablation in the heart", Dept. of Biomedical Engineering, University of NC, Chapel Hill, 2006, i-xvii; 1-138.

Holmes, Douglas et al., "Tissue Sensing Technology Enhances Lesion Formation During Irrigated Catheter Ablation", HRS, 2008, Abstract only.

ISR PCT/US2008/084194, , "ISR mailed Feb. 5, 2009".

Masse, Stephane et al., "A Three-dimensional display for cardiac activation mapping", Pace, vol. 14, Apr. 1991.

Salazar, Y et al., "Transmural versus nontransmural in situ electrical impedance spectrum for healthy, ischemic, and healed myocardium", IEEE Xplore, Abstract, 2009.

Zheng, Xiangsheng et al., "Electrode Impedance: An Indicator of Electrode-Tissue Contact and Lesion Dimensions During Linear Ablation", Journal of Interventional Cardiac Electrophysiology 4, 2000, 645-654.

International Search Report and Written Opinon in PCT Application No. PCT/US2006/061710 (Feb. 15, 2008).

International Search Report and Written Opinon in PCT Application No. PCT/US2006/061711 (Oct. 5, 2007).

International Search Report and Written Opinion in PCT Application No. PCT/US2006/061712 (Oct. 29, 2007).

International Search Report and Written Opinion in PCT Application No. PCT/US2006/061716 (Oct. 4, 2007).

International Search Report and Written Opinion in PCT Application No. PCT/US2006/061717 (Oct. 4, 2007).

(56) References Cited

OTHER PUBLICATIONS

International Search Report and Written Opinion in PCT Application No. PCT/US2008/084200 (Jan. 22, 2009).
International Search Report and Written Opinion in PCT Application No. PCT/US2010/034412 (Jun. 29, 2010).
International Search Report and Written Opinion in PCT Application No. PCT/US2010/034414 (Sep. 1, 2010).
Supplementary European Search Report in EP Application No. 06839102.8 (Nov. 16, 2009).
Supplementary European Search Report in EP Application No. 06840133.0 (Nov. 16, 2009).
Supplementary European Search Report in EP Application No. 10775417.8 (Oct. 25, 2013).
Supplementary Partial European Search Report in EP Application No. 06848530.9 (Nov. 17, 2009).
Thomas, Stuart P., et al., Comparison of Epicardial and Endocardial Linear Ablation Using Handheld Probes, The Annals of Thoracic Surgery, vol. 75, Issue 2, pp. 543-548, Feb. 2003.
Written Opinion of the International Searching Authority in PCT Application No. PCT/US2006/046565 (May 2, 2007).
International Search Report and Written Opinion in PCT Application No. PCT/US2006/061713 (Oct. 3, 2007).

* cited by examiner

SYSTEM AND METHOD FOR ASSESSING LESIONS IN TISSUE

This application is a continuation of U.S. patent application Ser. No. 12/622,488, filed Nov. 20, 2009, now U.S. Pat. No. 8,403,925, which claims the benefit of U.S. Provisional Application Ser. No. 61/177,876 filed on May 13, 2009, and which is a continuation-in-part of U.S. patent application Ser. No. 12/253,637, filed Oct. 17, 2008, now U.S. Pat. No. 8,449, 535, the entire disclosures of which are incorporated herein by reference. U.S. patent application Ser. No. 12/253,637 is, in turn, a continuation-in-part of U.S. patent application Ser. No. 12/095,688 filed May 30, 2008, the entire disclosure of which is also incorporated herein by reference. U.S. patent application Ser. No. 12/095,688 is a national stage application of, and claims priority to, International Application No. PCT/US2006/061714 filed Dec. 6, 2006, the entire disclosure of which is incorporated herein by reference. The International Application was published in the English language on Jun. 14, 2007 as International Publication No. WO 2007/067941 A2 and itself claims the benefit of U.S. Provisional Patent Application No. 60/748,234 filed Dec. 6, 2005, the entire disclosure of which is incorporated herein by reference.

BACKGROUND a. Technical Field

This invention relates to a system and method for assessing the formation of lesions in tissue in a body. In particular, the instant invention relates to a system and method for assessing the formation of lesions created by one or more electrodes on a therapeutic medical device, such as an ablation catheter, in tissue, such as cardiac tissue.

b. Background Art

It is generally known that ablation therapy may be used to treat various conditions afflicting the human anatomy. One such condition that ablation therapy finds a particular application is in the treatment of atrial arrhythmias, for example. When tissue is ablated, or at least subjected to ablative energy generated by an ablation generator and delivered by ablation catheter, lesions form in the tissue. More particularly, electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter). Arrhythmia can create a variety of dangerous conditions including irregular heart rates, loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

One challenge with ablation procedures is in the assessment of the lesion formation as a result of the application of ablative energy to the tissue. For example, it may be difficult to determine whether a particular area of tissue has been ablated or not, the extent to which ablated tissue has been ablated, whether a lesion line is continuous or has gaps therein, etc. Lesion formation has typically been fairly crudely assessed using any one of a number of different empirical techniques.

One such technique depends on a subjective sense for catheter contact combined with RF power settings, for example, and the duration the electrode spends in contact with the tissue. Another technique employs temperature sensing. Ablation generators and their ablation catheters monitor temperature, but with the advent of saline cooled catheters, temperature has gone from an index of catheter temperature (and less directly an index of tissue temperature), to a nearly useless index primarily reflecting irrigant saline flow. A further method relies on ablation catheter electrogram signals. RF ablated myocardium demonstrates poor depolarization wavefront conduction and thus local electrogram amplitude reduction and morphology changes are sometimes, but not consistently, observed. Accordingly, the assessment of lesion formation has ordinarily no direct objective basis.

The inventors herein have recognized a need for a system and method for assessing or the formation of lesions in tissue that will minimize and/or eliminate one or more of the above-identified deficiencies.

SUMMARY

The present invention is directed to a system and method for assessing the formation of lesions in a tissue in a body. The system according to the present teachings includes an electronic control unit (ECU). The ECU is configured to acquire values for first and second components of a complex impedance between the electrode and the tissue. The ECU is further configured to calculate an index responsive to the first and second values. The ECU is still further configured to process the calculated index to assess lesion formation in a particular area of the tissue.

In an exemplary embodiment, the ECU is further configured to acquire values for a predetermined variable and to calculate the index responsive to the first and second complex impedance components and the value of the predetermined variable. In an exemplary embodiment the predetermined variable comprises at least one of a contact force applied by the electrode against the tissue, a contact pressure applied by the electrode against the tissue, a temperature of the tissue, a change in temperature of the tissue, trabeculation of the tissue, saline flow rate, and blood flow rate.

In accordance with another aspect of the invention, an article of manufacture is provided. The article of manufacture includes a computer-readable storage medium having a computer program encoded thereon for assessing the formation of lesions in tissue. The computer program includes code that, when executed by a computer, causes the computer to perform the steps of calculating an index responsive to values for first and second components of a complex impedance between the electrode and the tissue, and processing the calculated index to assess lesion formation in a particular area of tissue.

In accordance with yet another aspect of the invention, a method for assessing the formation of lesions in a tissue in a body is provided. The method includes a first step of acquiring values for first and second components of a complex impedance between the electrode and the tissue. In a second step, an index responsive to the first and second values is calculated. A third step includes processing the calculated index to assess lesion formation in a particular area of tissue.

Finally, in accordance with yet still another aspect of the invention, an automated catheter guidance system is provided. The system includes a catheter manipulator assembly and a catheter associated with the catheter manipulator assembly. The catheter, in turn, has an electrode associated therewith. The system further includes a controller configured to direct movement of the catheter in response to an index calculated from first and second components of a complex impedance between the electrode and a tissue in a body.

In one exemplary embodiment, the catheter manipulator assembly is a robotic catheter device cartridge, and the controller is configured to direct movement of the catheter device cartridge, and therefore, the catheter. In another exemplary embodiment, the catheter manipulator assembly comprises a magnetic field generator that is configured to generate a magnetic field to control the movement of a magnetic element located in or on the catheter, and therefore, to control the movement of the catheter.

The foregoing and other aspects, features, details, utilities, and advantages of the present invention will be apparent from reading the following description and claims, and from reviewing the accompanying drawings.

DETAILED DESCRIPTION

Figure 1:
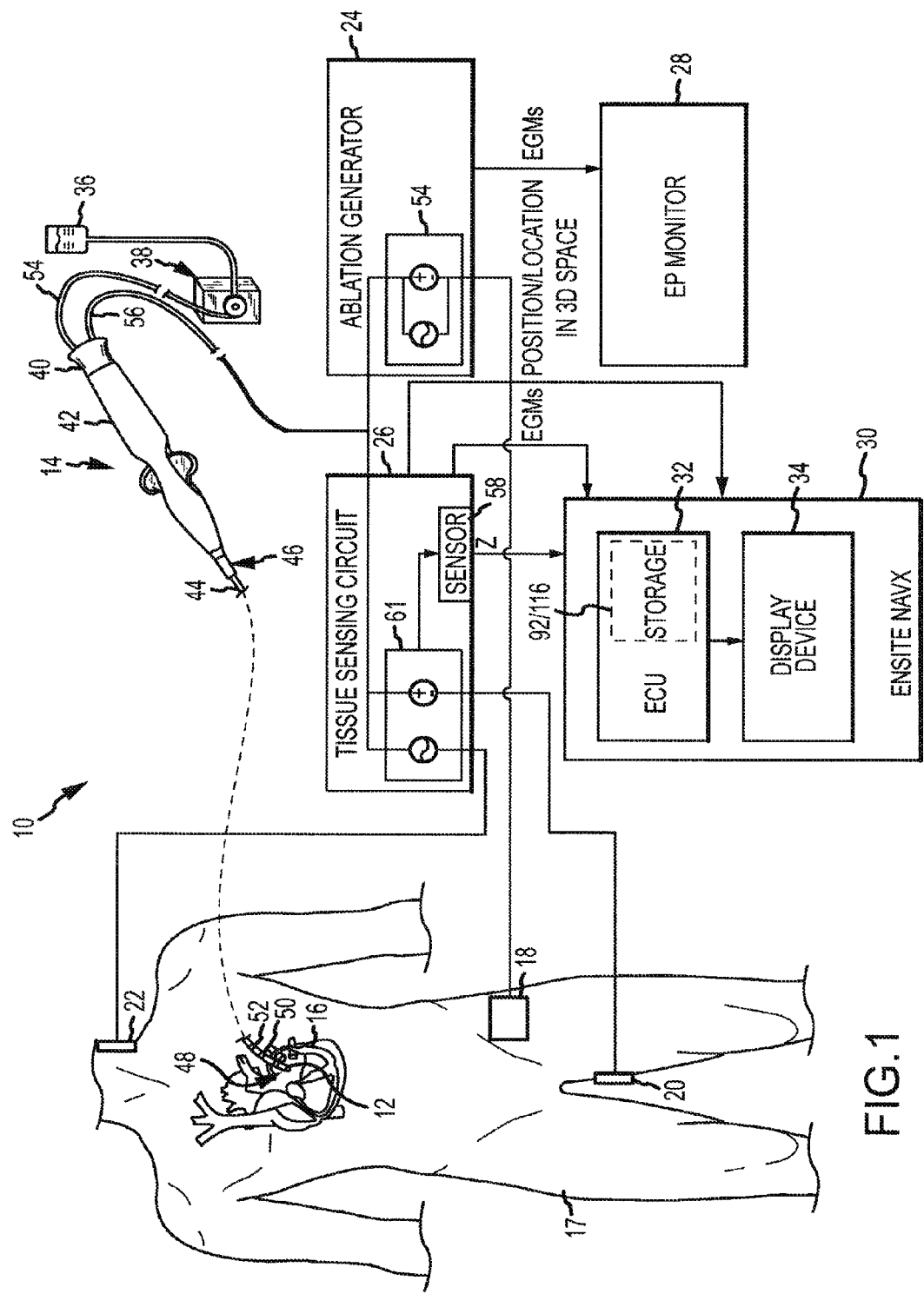
FIG. 1 is diagrammatic view of a system in accordance with the present teachings.

Referring now to the drawings wherein like reference numerals are used to identify identical components in the various views, FIG. 1 illustrates one embodiment of a system 10 for one or more diagnostic and therapeutic functions including components providing an improved assessment of, among other things, a degree of coupling between an electrode 12 on a catheter 14 and a tissue 16 in a body 17. As will be described in greater detail below, the degree of coupling can be useful for assessing, among other things, the degree of contact between the electrode 12 and the tissue 16, the relative proximity of the electrode 12 to the tissue 16, and the formation of lesions in the tissue 16. In the illustrated embodiment, the tissue 16 comprises heart or cardiac tissue. It should be understood, however, that the present invention may be used to evaluate coupling between electrodes and a variety of body tissues. Further, although the electrode 12 is illustrated as part of the catheter 14, it should be understood that the present invention may be used to assess a degree of coupling between any type of electrode and tissue including, for example, intracardiac electrodes, needle electrodes, patch electrodes, wet brush electrodes (such as the electrodes disclosed in commonly assigned U.S. patent application Ser. No. 11/190,724 filed Jul. 27, 2005, the entire disclosure of which is incorporated herein by reference) and virtual electrodes (e.g., those formed from a conductive fluid medium such as saline including those disclosed in commonly assigned U.S. Pat. No. 7,326,208 issued Feb. 5, 2008, the entire disclosure of which is incorporated herein by reference). In addition to the catheter 14, the system 10 may include patch electrodes 18, 20, 22, an ablation generator 24, a tissue sensing circuit 26, an electrophysiology (EP) monitor 28, and a system 30 for visualization, mapping and navigation of internal body structures which may include an electronic control unit 32 in accordance with the present invention and a display device 34, among other components.

The catheter 14 is provided for examination, diagnosis and treatment of internal body tissues such as the tissue 16. In accordance with one embodiment of the invention, the catheter 14 comprises an ablation catheter and, more particularly, an irrigated radio-frequency (RF) ablation catheter. It should be understood, however, that the present invention can be implemented and practiced regardless of the type of ablation energy provided (e.g., cryoablation, ultrasound, etc.) In an exemplary embodiment, the catheter 14 is connected to a fluid source 36 having a biocompatible fluid such as saline through a pump 38 (which may comprise, for example, a fixed rate roller pump or variable volume syringe pump with a gravity feed supply from the fluid source 36 as shown) for irrigation. It should be noted, however, that the present invention is not meant to be limited to irrigated catheters. In an exemplary embodiment, the catheter 14 is also electrically connected to the ablation generator 24 for delivery of RF energy. The catheter 14 may include a cable connector or interface 40, a handle 42, a shaft 44 having a proximal end 46 and a distal 48 end (as used herein, "proximal" refers to a direction toward the end of the catheter near the clinician, and "distal" refers to a direction away from the clinician and (generally) inside the body of a patient) and one or more electrodes 12, 50, 52. The catheter 14 may also include other conventional components not illustrated herein such as a temperature sensor, additional electrodes, and corresponding conductors or leads.

The connector 40 provides mechanical, fluid and electrical connection(s) for cables 54, 56 extending from the pump 38 and the ablation generator 24. The connector 40 is conventional in the art and is disposed at a proximal end of the catheter 14.

The handle 42 provides a location for the clinician to hold the catheter 14 and may further provide means for steering or the guiding shaft 44 within the body 17. For example, the handle 42 may include means to change the length of a guidewire extending through the catheter 14 to the distal end 48 of the shaft 44 to steer the shaft 44. The handle 42 is also conventional in the art and it will be understood that the construction of the handle 42 may vary. In an alternate exemplary embodiment, the catheter 14 may be robotically driven or controlled. Accordingly, rather than a clinician manipulating a handle to steer or guide the catheter 14, and the shaft 44 thereof, in particular, a robot is used to manipulate the catheter 14.

The shaft 44 is an elongated, tubular, flexible member configured for movement within the body 17. The shaft 44 support the electrodes 12, 50, 52, associated conductors, and possibly additional electronics used for signal processing or conditioning. The shaft 44 may also permit transport, delivery and/or removal of fluids (including irrigation fluids and bodily fluids), medicines, and/or surgical tools or instruments. The shaft 44 may be made from conventional materials such as polyurethane and defines one or more lumens configured to house and/or transport electrical conductors, fluids or surgical tools. The shaft 44 may be introduced into a blood vessel or other structure within the body 17 through a conventional introducer. The shaft 44 may then be steered or guided through the body 17 to a desired location such as the tissue 16 with guidewires or other means known in the art.

The electrodes 12, 50, 52 are provided for a variety of diagnostic and therapeutic purposes including, for example, electrophysiological studies, catheter identification and location, pacing, cardiac mapping and ablation. In the illustrated embodiment, the catheter 14 includes an ablation tip electrode 12 at the distal end 48 of the shaft 44, and a pair of ring electrodes 50, 52. It should be understood, however, that the number, shape, orientation and purpose of the electrodes 12, 50, 52 may vary.

The patch electrodes 18, 20, 22 provide RF or navigational signal injection paths and/or are used to sense electrical potentials. The electrodes 18, 20, 22 may also have additional purposes such as the generation of an electromechanical map. The electrodes 18, 20, 22 are made from flexible, electrically conductive material and are configured for affixation to the body 17 such that the electrodes 18, 20, 22 are in electrical contact with the patient's skin. The electrode 18 may function as an RF indifferent/dispersive return for the RF ablation signal. The electrodes 20, 22 may function as returns for the RF ablation signal source and/or an excitation signal generated by the tissue sensing circuit 26 as described in greater detail below. In accordance with one aspect of the present invention discussed below, the electrodes 20, 22 are preferably spaced relatively far apart. In the illustrated embodiment, the electrodes 20, 22 are located on the medial aspect of the left leg and the dorsal aspect of the neck. The electrodes 20, 22, may alternatively be located on the front and back of the torso or in other conventional orientations.

The ablation generator 24 generates, delivers, and controls RF energy output by the ablation catheter 14. The generator 24 is conventional in the art and may comprise the commercially available unit sold under the model number IBI-1500T RF Cardiac Ablation Generator, available from Irvine Biomedical, Inc. The generator 24 includes an RF ablation signal source 54 configured to generate an ablation signal that is output across a pair of source connectors: a positive polarity connector SOURCE (+) which may connect to the tip electrode 12; and a negative polarity connector SOURCE(−) which may be electrically connected by conductors or lead wires to one of the patch electrodes 18, 20, 22 (see FIG. 2). It should be understood that the term connectors as used herein does not imply a particular type of physical interface mechanism, but is rather broadly contemplated to represent one or more electrical nodes. The source 54 is configured to generate a signal at a predetermined frequency in accordance with one or more user specified parameters (e.g., power, time, etc.) and under the control of various feedback sensing and control circuitry as is know in the art. The source 54 may generate a signal, for example, with a frequency of about 450 kHz or greater. The generator 24 may also monitor various parameters associated with the ablation procedure including impedance, the temperature at the tip of the catheter, ablation energy and the position of the catheter and provide feedback to the clinician regarding these parameters. The impedance measurement output by the generator 24, however, reflects the magnitude of impedance not only at the tissue 16, but the entire impedance between the tip electrode 12 and the corresponding patch electrode 18 on the body surface. The impedance output by the generator 24 is also not easy to interpret and correlate to tissue contact by the clinician. In an exemplary embodiment, the ablation generator 24 may generate a higher frequency current for the purposes of RF ablation, and a second lower frequency current for the purpose of measuring impedance.

The tissue sensing circuit 26 provides a means, such as a tissue sensing signal source 61, for generating an excitation signal used in impedance measurements and means, such as a complex impedance sensor 58, for resolving the detected impedance into its component parts. The signal source 61 is configured to generate an excitation signal across source connectors SOURCE(+) and SOURCE (−) (See FIG. 2). The source 61 may output a signal having a frequency within a range from about 1 kHz to over 500 kHz, more preferably within a range of about 2 kHz to 200 kHz, and even more preferably about 20 kHz. In one embodiment, the excitation signal is a constant current signal, preferably in the range of between 20-200 µA, and more preferably about 100 µA. As discussed below, the constant current AC excitation signal generated by the source 61 is configured to develop a corresponding AC response voltage signal that is dependent on the complex impedance of the tissue 16 and is sensed by the complex impedance sensor 58. The complex impedance is resolved into its component parts (i.e., the resistance (R) and reactance (X) or the impedance magnitude (|Z|) and phase angle (∠Z or φ)). Sensor 58 may include conventional filters (e.g., bandpass filters) to block frequencies that are not of interest, but permit appropriate frequencies, such as the excitation frequency, to pass, as well as conventional signal processing software used to obtain the component parts of the measured complex impedance.

It should be understood that variations are contemplated by the present invention. For example, the excitation signal may be an AC voltage signal where the response signal comprises an AC current signal. Nonetheless, a constant current excitation signal is preferred as being more practical. While in some situations there can be advantages to having an excitation signal frequency at or near the frequency of the RF ablation signal, it should be appreciated that the excitation signal frequency is preferably outside of the frequency range of the RF ablation signal, which allows the complex impedance sensor 58 to more readily distinguish the two signals, and facilitates filtering and subsequent processing of the AC response voltage signal. Alternatively, the system can cycle each signal (RF ablation and excitation) on and off in alternating periods so they do not overlap in time. The excitation signal frequency is also preferably outside the frequency range of conventionally expected electrogram (EGM) signals in the frequency range of 0.05 Hz-1 kHz. Thus, in summary, the excitation signal preferably has a frequency that is preferably above the typical EGM signal frequencies and below the typical RF ablation signal frequencies.

The circuit 26 is also connected, for a purpose described below, across a pair of sense connectors: a positive polarity connector SENSE (+) which may connect to the tip electrode 12; and a negative polarity connector SENSE (−) which may be electrically connected to one of the patch electrodes 18, 20, 22 (see FIG. 2; note, however, that the connector SENSE (−) should be connected to a different electrode of the electrodes 18, 20, 22 relative to the connector SOURCE (−) as discussed below). It should again be understood that the term connectors as used herein does not imply a particular type of physical interface mechanism, but is rather broadly contemplated to represent one or more electrical nodes.

Figure 2:
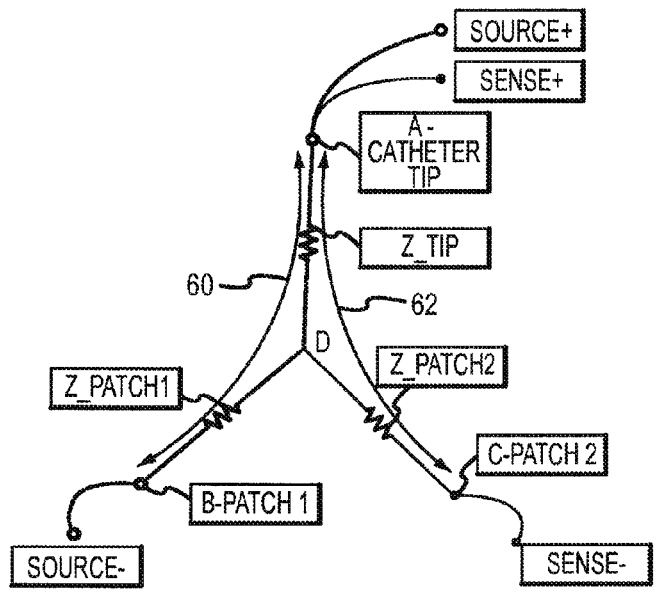
FIG. 2 is a simplified schematic diagram illustrating how impedance is determined in accordance with the present teachings.

Referring now to FIG. 2, connectors SOURCE (+), SOURCE (−), SENSE (+) and SENSE (−) form a three terminal arrangement permitting measurement of the complex impedance at the interface of the tip electrode 12 and the tissue 16. Complex impedance can be expressed in rectangular coordinates as set forth in equation (1):

$$Z = R + jX \quad (1)$$

where R is the resistance component (expressed in ohms); and X is a reactance component (also expressed in ohms). Complex impedance can also be expressed polar coordinates as set forth in equation (2):

$$Z = r \cdot e^{j\theta} = |Z| \cdot e^{j \angle Z} \quad (2)$$

where |Z| is the magnitude of the complex impedance (expressed in ohms) and $\angle Z = \theta$ is the phase angle expressed in radians. Alternatively, the phase angle may be expressed in terms of degrees where $$\phi = \left(\frac{180}{\pi}\right)\theta.$$

Throughout the remainder of this specification, phase angle will be preferably referenced in terms of degrees. The three terminals comprise: (1) a first terminal designated "A-Catheter Tip" which is the tip electrode 12; (2) a second terminal designated "B-Patch 1" such as the source return patch electrode 22; and (3) a third terminal designated "C-Patch 2" such as the sense return patch electrode 20. In addition to the ablation (power) signal generated by the source 54 of the ablation generator 24, the excitation signal generated by the source 61 in the tissue sensing circuit 26 is also be applied across the source connectors (SOURCE (+), SOURCE(−)) for the purpose of inducing a response signal with respect to the load that can be measured and which depends on the complex impedance. As described above, in one embodiment, a 20 kHz, 100 µA AC constant current signal is sourced along a path 60, as illustrated, from one connector (SOURCE (+), starting at node A) through the common node (node D) to a return patch electrode (SOURCE (−), node B). The complex impedance sensor 58 is coupled to the sense connectors (SENSE (+), SENSE (−)), and is configured to determine the impedance across a path 62. For the constant current excitation signal of a linear circuit, the impedance will be proportional to the observed voltage developed across SENSE (+)/SENSE(−), in accordance with Ohm's Law: Z=V/I. Because voltage sensing is nearly ideal, the current flows through the path 60 only, so the current through the path 62 (node D to node C) due to the excitation signal is effectively zero. Accordingly, when measuring the voltage along the path 62, the only voltage observed will be where the two paths intersect (i.e., from node A to node D). Depending on the degree of separation of the two patch electrodes (i.e., those forming nodes B and C), an increasing focus will be placed on the tissue volume nearest the tip electrode 12. If the patch electrodes are physically close to each other, the circuit pathways between the catheter tip electrode 12 and the patch electrodes will overlap significantly and impedance measured at the common node (i.e., node D) will reflect impedances not only at the interface of the catheter electrode 12 and the tissue 16, but also other impedances between the tissue 16 and the surface of body 17. As the patch electrodes are moved further apart, the amount of overlap in the circuit paths decreases and impedance measured at the common node is only at or near the tip electrode 12 of the catheter 14.

Figure 3:
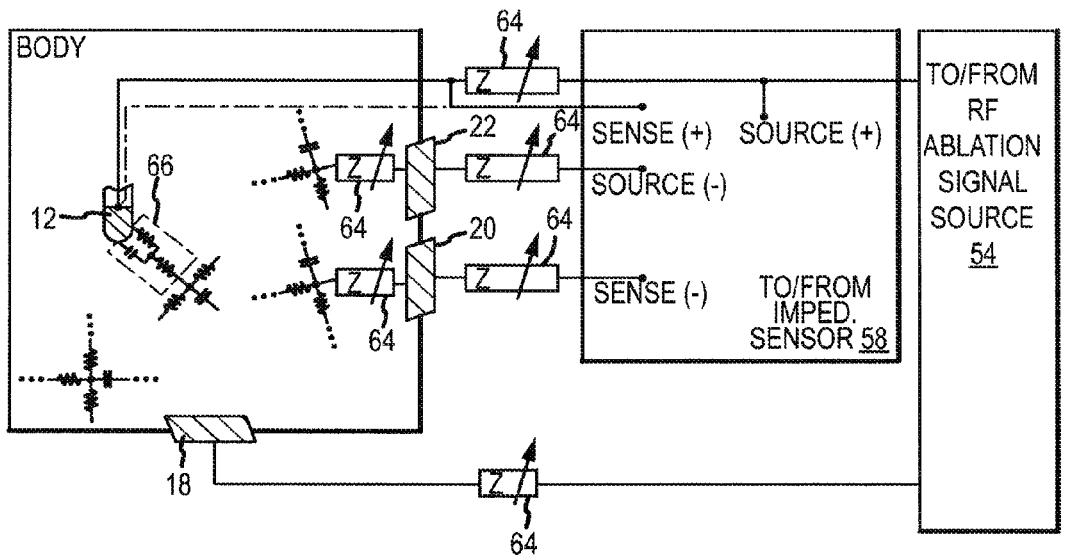
FIG. 3 is a diagrammatic and block diagram illustrating the approach in FIG. 2 in greater detail.

Referring now to FIG. 3, the concept illustrated in FIG. 2 is extended. FIG. 3 is a simplified schematic and block diagram of the three-terminal measurement arrangement of the invention. For clarity, it should be pointed out that the SOURCE (+) and SENSE (+) lines may be joined in the catheter connector 40 or the handle 42 (as in solid line) or may remain separate all the way to the tip electrode 12 (the SENSE (+) line being shown in phantom line from the handle 42 to the tip electrode 12). FIG. 3 shows, in particular, several sources of complex impedance variations, shown generally as blocks 64, that are considered "noise" because such variations do not reflect the physiologic changes in the tissue 16 or electrical coupling whose complex impedance is being measured. For reference, the tissue 16 whose complex impedance is being measured is that near and around the tip electrode 12 and is enclosed generally by a phantom-line box 66 (and the tissue 16 is shown schematically, in simplified form, as a resistor/capacitor combination). One object of the invention is to provide a measurement arrangement that is robust or immune to variations that are not due to changes in or around the box 66. For example, the variable complex impedance boxes 64 that are shown in series with the various cable connections (e.g., in the SOURCE (+) connection, in the SOURCE (−) and SENSE (−) connections, etc.) may involve resistive/inductive variations due to cable length changes, cable coiling and the like. The variable complex impedance boxes 64 that are near the patch electrodes 20, 22, may be more resistive/capacitive in nature, and may be due to body perspiration and the like over the course of a study. As will be seen, the various arrangements of the invention are relatively immune to the variations in the blocks 64, exhibiting a high signal-to-noise (S/N) ratio as to the complex impedance measurement for the block 66.

Although the SOURCE (−) and SENSE (−) returns are illustrated in FIG. 3 as patch electrodes 20, 22, it should be understood that other configurations are possible. In particular, the indifferent/dispersive return electrode 18 can be used as a return as well as another electrode 50, 52 on the catheter 14, such as the ring electrode 50 as described in commonly assigned U.S. patent application Ser. No. 11/966,232 filed on Dec. 28, 2007 and titled "System and Method for Measurement of an Impedance Using a Catheter such as an Ablation Catheter," the entire disclosure of which is incorporated herein by reference.

The EP monitor 28 is provided to display electrophysiology data including, for example, an electrogram. The monitor 28 is conventional in the art and may comprise an LCD or CRT monitor or another conventional monitor. The monitor 28 may receive inputs from the ablation generator 24 as well as other conventional EP lab components not shown in the illustrated embodiment.

The system 30 is provided for visualization, mapping, and navigation of internal body structures. The system 30 may comprise the system having the model name EnSite NavX™ and commercially available from St. Jude Medical, Inc. and as generally shown with reference to commonly assigned U.S. Pat. No. 7,263,397 titled "Method and Apparatus for Catheter Navigation and Location and Mapping in the Heart," the entire disclosure of which is incorporated herein by reference. Other systems may include the Biosense Webster Carto™ System, commonly available fluoroscopy systems, or a magnetic location system such as the gMPS system from Mediguide Ltd. The system 30 may include the electronic control unit (ECU) 32 and the display device 34 among other components. However, in another exemplary embodiment, the ECU 32 is a separate and distinct component that is electrically connected to the system 30.

The ECU 32 is provided to acquire values for first and second components of a complex impedance between the catheter tip electrode 12 and the tissue 16 and to calculate an electrical coupling index (ECI) responsive to the values with the coupling index indicative of a degree of coupling between the electrode 12 and the tissue 16. The ECU 32 preferably comprises a programmable microprocessor or microcontroller, but may alternatively comprise an application specific integrated circuit (ASIC). The ECU 32 may include a central processing unit (CPU) and an input/output (I/O) interface through which the ECU 32 may receive a plurality of input signals including signals from the sensor 58 of the tissue sensing circuit 26 and generate a plurality of output signals including those used to control the display device 34. In accordance with one aspect of the present invention, the ECU 32 may be programmed with a computer program (i.e., software) encoded on a computer storage medium for determining a degree of coupling between the electrode 12 on the catheter 14 and the tissue 16 in the body 17. The program includes code for calculating an ECI responsive to values for first and second components of the complex impedance between the catheter electrode 12 and the tissue 16 with the ECI indicative of a degree of coupling between the catheter electrode 12 and the tissue 16.

The ECU 32 acquires one or more values for two component parts of the complex impedance from signals generated by the sensor 58 of the tissue sensing circuit 26 (i.e., the resistance (R) and reactance (X) or the impedance magnitude (|Z|) and phase angle ($\phi$) or any combination of the foregoing or derivatives or functional equivalents thereof). In accordance with one aspect of the present invention, the ECU 32 combines values for the two components into a single ECI that provides an improved measure of the degree of coupling between the electrode 12 and the tissue 16 and, in particular, the degree of electrical coupling between the electrode 12 and the tissue 16. As will be described in greater detail below, the single ECI may provide an improved measure of the proximity of the electrode 12 relative to the tissue 16, as well as improved assessment of lesion formation in the tissue 16.

Validation testing relating to the coupling index was performed in a pre-clinical animal study. The calculated coupling index was compared to pacing threshold as an approximation of the degree of coupling. Pacing threshold was used for comparison because it is objective and particularly sensitive to the degree of physical contact between the tip electrode and tissue when the contact forces are low and the current density paced into the myocardium varies. In a study of seven swine (n=7, 59+/−3 kg), a 4 mm tip irrigated RF ablation catheter was controlled by an experienced clinician who scored left and right atrial contact at four levels (none, light, moderate and firm) based on clinician sense, electrogram signals, three-dimensional mapping, and fluoroscopic images. Several hundred pacing threshold data points were obtained along with complex impedance data, electrogram amplitudes and data relating to clinician sense regarding contact. A regression analysis was performed using software sold under the registered trademark "MINITAB" by Minitab, Inc. using the Log 10 of the pacing threshold as the response and various impedance parameters as the predictor. The following table summarizes the results of the analysis:

| Model | | | Regression Factors in Model | | | Regression $R^2$ $R^2$ | $R^2$_adj |
|---|---|---|---|---|---|---|---|
| 1 | | | | | | R1_mean (p < 0.001) | 43.60% | 43.50% |
| 2 | | | | | | X1_mean (p < 0.001) | 35.70% | 35.50% |
| 3 | | | | | X1_mean (p < 0.001) | R1_mean (p < 0.001) | 47.20% | 46.90% |
| 4 | | X1_stdev (p = 0.300) | R1_stdev (p = 0.155) | X1_mean (p < 0.001) | R1_mean (p < 0.001) | 48.70% | 48.00% |
| 5 | R1_P-P (p = 0.253) | X1_stdev (p = 0.280) | R1_stdev (p = 0.503) | X1_mean (p < 0.001) | R1_mean (p < 0.001) | 49.00% | 48.10% |

As shown in the table, it was determined that a mean value for resistance accounted for 43.5% of the variation in pacing threshold while a mean value for reactance accounted for 35.5% of the variation in pacing threshold. Combining the mean resistance and mean reactance values increased the predictive power to 46.90% demonstrating that an ECI based on both components of the complex impedance will yield improved assessment of coupling between the catheter electrode 12 and the tissue 16. As used herein, the "mean value" for the resistance or reactance may refer to the average of N samples of a discrete time signal $x_i$ or a low-pass filtered value of a continuous x(t) or discrete $x(t_i)$ time signal. As shown in the table, adding more complex impedance parameters such as standard deviation and peak to peak magnitudes can increase the predictive power of the ECI. As used herein, the "standard deviation" for the resistance or reactance may refer to the standard deviation, or equivalently root mean square (rms) about the mean or average of N samples of a discrete time signal $x_i$ or the square root of a low pass filtered value of a squared high pass filtered continuous x(t) or discrete $x(t_i)$ time signal. The "peak to peak magnitude" for the resistance or reactance may refer to the range of the values over the previous N samples of the discrete time signal $x_i$ or the $k^{th}$ root of a continuous time signal $[abs(x(t))]^k$ that has been low pass filtered for sufficiently large k>2. It was further determined that, while clinician sense also accounted for significant variation in pacing threshold (48.7%)—and thus provided a good measure for assessing coupling—the combination of the ECI with clinician sense further improved assessment of coupling (accounting for 56.8% of pacing threshold variation).

Because of the processing and resource requirements for more complex parameters such as standard deviation and peak to peak magnitude, and because of the limited statistical improvement these parameters provided, it was determined that the most computationally efficient ECI would be based on mean values of the resistance (R) and reactance (X), and more specifically, the equation:

$$ECI=a*Rmean+b*Xmean+c.$$

From the regression equation, and using a 4 mm irrigated tip catheter, the best prediction of pacing threshold—and therefore coupling—was determined to be the following equation (3):

$$ECI=Rmean-5.1*Xmean \quad (3)$$

where Rmean is the mean value of a plurality of resistance values and Xmean is the mean value of a plurality of reactance values. It should be understood, however, that other values associated with the impedance components, such as a standard deviation of a component or peak to peak magnitude of a component which reflect variation of impedance with cardiac motion or ventilation, can also serve as useful factors in the ECI. Further, although the above equation and following discussion focus on the rectangular coordinates of resistance (R) and reactance (X), it should be understood that the ECI could also be based on values associated with the polar coordinates impedance magnitude (|Z|) and phase angle (φ) or indeed any combination of the foregoing components of the complex impedance and derivatives or functional equivalents thereof. Finally, it should be understood that coefficients, offsets and values within the equation for the ECI may vary depending on, among other things, the specific catheter used, the patient, the equipment, the desired level of predictability, the species being treated, and disease states. In accordance with the present invention, however, the coupling index will always be responsive to both components of the complex impedance in order to arrive at an optimal assessment of coupling between the catheter electrode 12 and the tissue 16.

The above-described analysis was performed using a linear regression model wherein the mean value, standard deviation, and/or peak to peak magnitude of components of the complex impedance were regressed against pacing threshold values to enable determination of an optimal ECI. It should be understood, however, that other models and factors could be used. For example, a nonlinear regression model may be used in addition to, or as an alternative to, the linear regression model. Further, other independent measures of tissue coupling such as atrial electrograms could be used in addition to, or as an alternative to, pacing thresholds.

Validation testing was also performed in a human trial featuring twelve patients undergoing catheter ablation for atrial fibrillation. The patients were treated using an irrigated, 7 French radio frequency (RF) ablation catheter with a 4 mm tip electrode operating at a standard setting of a 50° C. tip temperature, 40 W power, and 30 ml/min. flow rate (adjusted accordingly proximate the esophagus). An experienced clinician placed the catheter in the left atrium in positions of unambiguous non-contact and unambiguous contact (with varying levels of contact including "light," "moderate," and "firm") determined through fluoroscopic imaging, tactile feedback electrograms, clinician experience, and other information. In addition to impedance, measurements of electrogram amplitudes and pacing thresholds were obtained for comparison. Each measure yielded corresponding changes in value as the catheter electrode moved from a no-contact position to a contact position. In particular, electrogram amplitudes increased from 0.14+/−0.16 to 2.0+/−1.9 mV, pacing thresholds decreased from 13.9+/−3.1 to 3.1+/−20 mA and the ECI increased from 118+/−15 to 145+/−24 (with resistance increasing from 94.7+/−11.0 to 109.3+/−15.1Ω and reactance decreasing from −4.6+/−0.9 to −6.9+/−2Ω). Further, the ECI increased (and resistance increased and reactance decreased) as the catheter electrode was moved from a "no-contact" (115+/−12) position to "light," (135+/−15) "moderate," (144+/−17) and "firm" (159+/−34) positions. These measurements further validate the use of the ECI to assess coupling between the catheter electrode 12 and the tissue 16. The calculated ECI and clinician sense of coupling were again compared to pacing threshold as an approximation of the degree of coupling. A regression analysis was performed using a logarithm of the pacing threshold as the response and various impedance parameters and clinician sense as predictors. From this analysis, it was determined that clinician sense accounted for approximately 47% of the variability in pacing threshold. The addition of the ECI, however, with clinician sense resulted in accounting for approximately 51% of the variability in pacing threshold—further demonstrating that the ECI can assist clinicians in assessing coupling between the catheter electrode 12 and the tissue 16.

Figure 4:
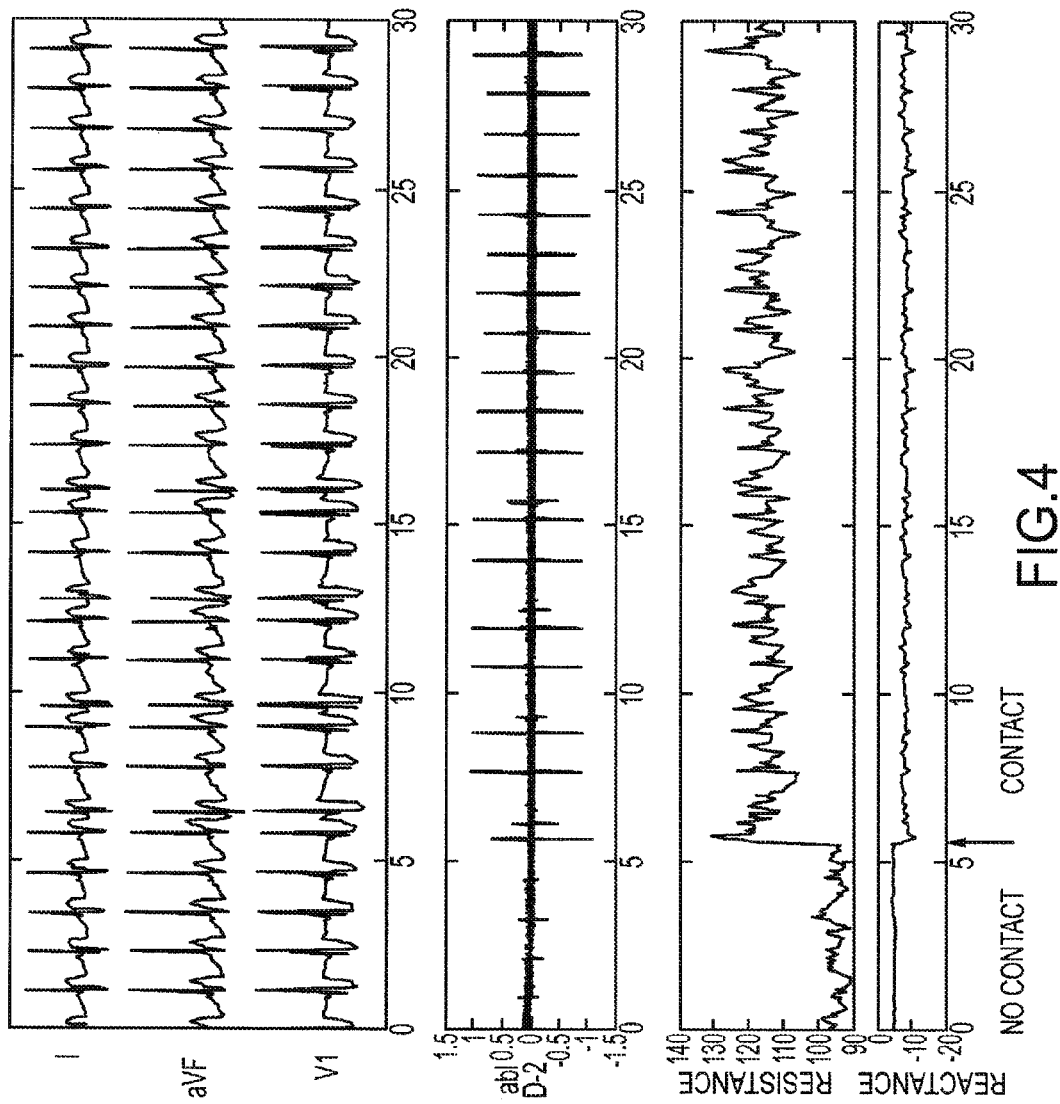
FIG. 4 is a series of diagrams illustrating complex impedance variations during atrial tissue ablation and cardiac tissue contact over thirty (30) seconds.
Figure 5:
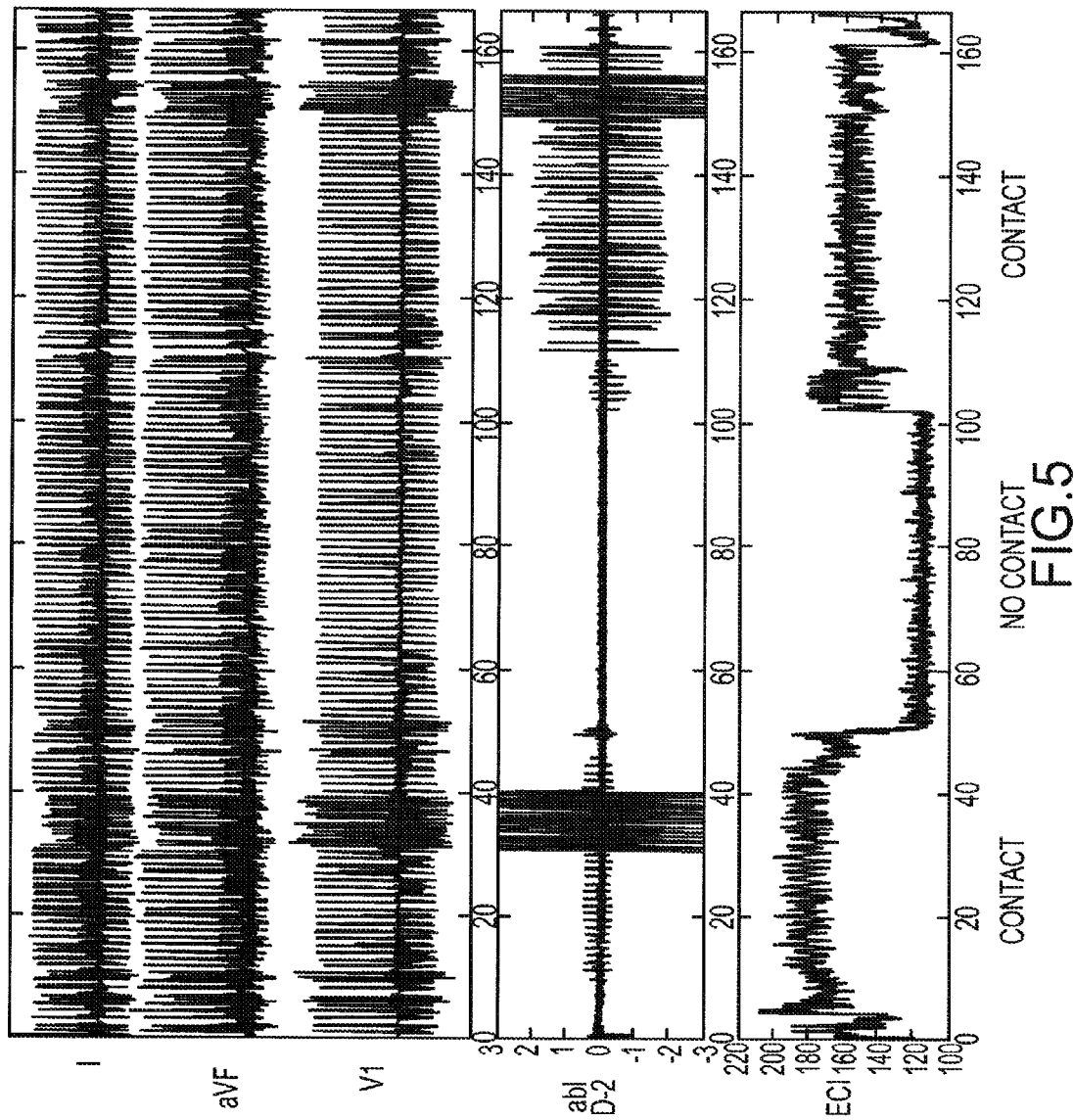
FIG. 5 is a series of diagrams illustrating variations in a coupling index during atrial tissue ablation and cardiac tissue contact over one hundred and sixty (160) seconds.

Referring now to FIGS. 4-5, a series of timing diagrams (in registration with each other) illustrate a comparison of atrial electrograms relative to changes in resistance and reactance (FIG. 4) and the composite ECI (FIG. 5). As noted hereinabove, atrial electrograms are one traditional measurement for assessing coupling between the catheter electrode 12 and the tissue 16. As shown in FIG. 4, the signal amplitude of the atrial electrogram (labeled "ABL D-2" in FIG. 4) increases when the catheter electrode 12 moves from a position of "no contact" to "contact" with the tissue 16. Similarly, measured resistance (R) increases and reactance (X) decreases and become more variable (FIG. 4) and the calculated ECI increases (FIG. 5), further demonstrating the utility of the ECI in assessing coupling between the electrode 12 and the tissue 16.

The human validation testing also revealed that the ECI varied depending on tissue types. For example, the ECI tended to be higher when the catheter electrode was located inside a pulmonary vein than in the left atrium. As a result, in accordance with another aspect of the present invention, the ECI may be used in identifying among tissue types (e.g., to identify vascular tissue as opposed to trabeculated and myocardial tissue). Further, because force sensors may not adequately estimate the amount of energy delivered into tissue in constrained regions, such as the pulmonary vein or trabeculae, the inventive ECI may provide a more meaningful measure of ablation efficacy than force sensors. In addition, in certain situations, it may be advantageous to utilize both a force sensor and the ECI. For example, if a particular location indicates a low reading on a force sensor but a high ECI reading, it can be an indication that the catheter is in a constrained region or is in close proximity to trabeculated tissue. Combining the readings of the force sensor, ECI and a mapping system allows the system to map tissue types on the 3D map, as well as differentiate between trabeculated tissue or constrained regions and smooth tissue with significant electrode applied force.

Impedance measurements are also influenced by the design of the catheter 14, the connection cables 56, or other factors. Therefore, the ECI may preferably comprise a flexible equation in which coefficients and offsets are variable in response to design parameters associated with the catheter 14 (e.g., ECI=a*Rmean+b*Xmean+c). The catheter 14 may include a memory such as an EEPROM that stores numerical values for the coefficients and offsets or stores a memory address for accessing the numerical values in another memory location (either in the catheter EEPROM or in another memory). The ECU 32 may retrieve these values or addresses directly or indirectly from the memory and modify the ECI accordingly.

The physical structure of the patient is another factor that may influence impedance measurements and the ECI. Therefore, the ECU 32 may also be configured to offset or normalize the ECI (e.g., by adjusting coefficients or offsets within the index) responsive to an initial measurement of impedance or another parameter in a particular patient. In addition, it may be beneficial to obtain and average values for the ECI responsive to excitation signals generated by the source 61 at multiple different frequencies.

Figure 6:
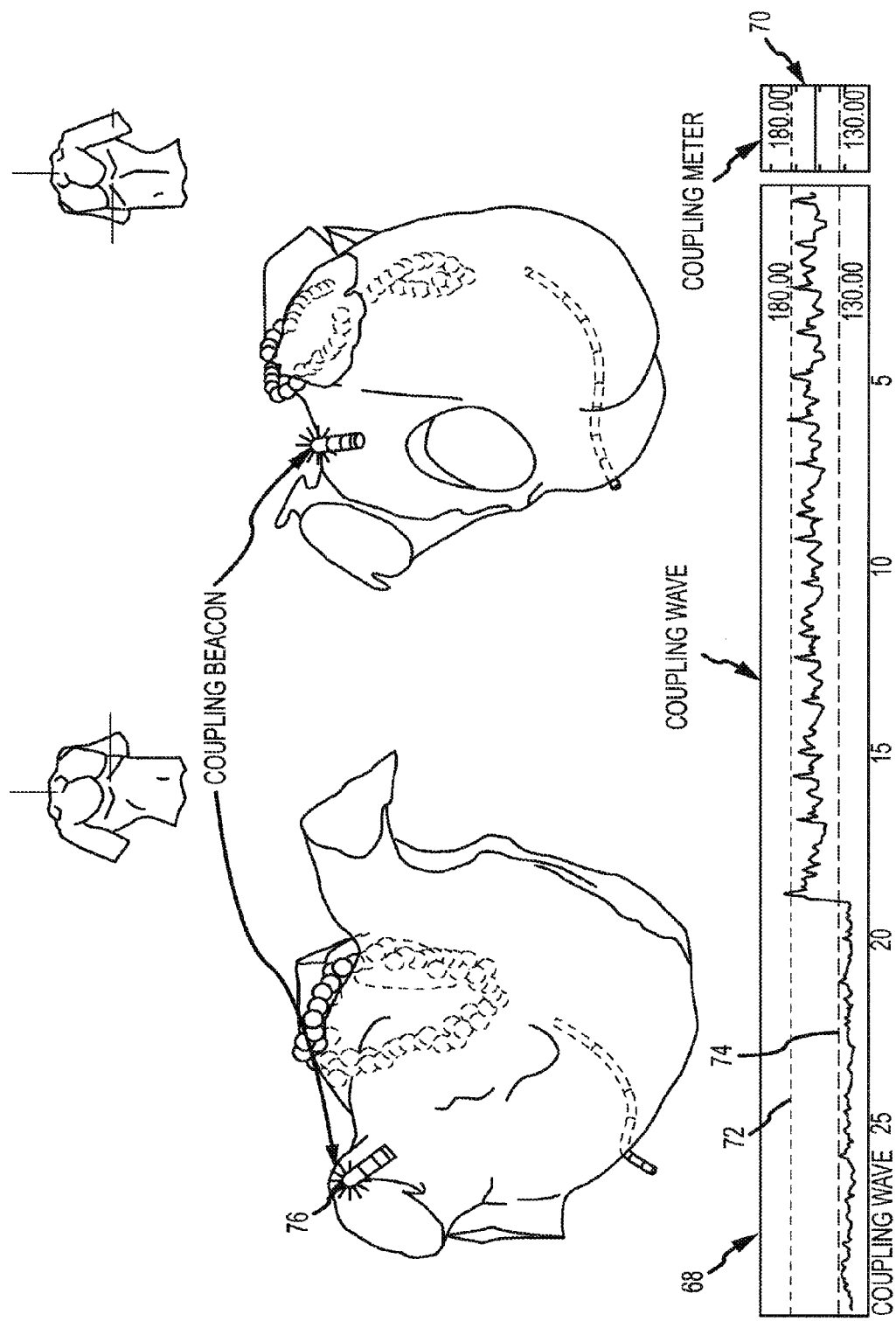
FIG. 6 is a screen display illustrating possible formats for presenting a coupling index to a clinician.

Referring now to FIG. 6, the display device 34 is provided to present the ECI in a format useful to the clinician. The device 34 may also provide a variety of information relating to visualization, mapping, and navigation, as is known in the art, including measures of electrical signals, two and three dimensional images of the tissue 16, and three-dimensional reconstructions of the tissue 16. The device 34 may comprise an LCD monitor or other conventional display device. In accordance with another aspect of the present invention, the ECI may be displayed in one or more ways to provide easy interpretation and correlation to tissue contact and/or proximity of the electrode 12 to the tissue 16 for the clinician. Referring to FIG. 6, the ECI may be displayed as a scrolling waveform 68. The ECI may also be displayed as a meter 70 which displays the one second average value of the ECI. For either the scrolling waveform 68 or the meter 70, upper and lower thresholds 72, 74 may be set (either pre-programmed in the ECU 32 or input by the user using a conventional I/O device). Characteristics of the waveform 68 and/or the meter 70 may change depending upon whether the value of the ECI is within the range set by the thresholds (e.g., the waveform 68 or the meter 70 may change colors, such as from green to red, if the value of the ECI moves outside of the range defined by the thresholds). Changes to the ECI may also be reflected in changes to the image of the catheter 14 and/or the catheter electrode 12 on the display device 34. For example, the catheter electrode 12 may be displayed on the screen (including within a two or three dimensional image or reconstruction of the tissue) as a beacon 76. Depending on the value of the ECI, the appearance of the beacon 76 may change. For example, the color of the beacon 76 may change (e.g., from green to red) and/or lines may radiate outwardly from the beacon 76 as the index falls above, below or within a range of values. In another exemplary embodiment, the length of the splines of the beacon 76 may continuously vary with the ECI.

In summary, the degree of coupling between a catheter electrode 12 and the tissue 16, which may be used to assess the proximity of the electrode 12 to the tissue 16, may be assessed through several method steps in accordance with one embodiment of the invention. First, an excitation signal is applied between the electrode 12 and a reference electrode such as the patch electrode 22 between connectors SOURCE (+) and SOURCE (−) along the first path 60 (see FIG. 2). As discussed above, the signal source 61 of the tissue sensing circuit 26 may generate the excitation signal at a predetermined frequency or frequencies. This action induces a voltage along the path 62 between the electrode 12 and another reference electrode such as the patch electrode 20. The voltage may be measured by the sensor 58 which resolves the sensed voltage into component parts of the complex impedance at the tissue 16. As a result, the ECU 32 acquires values for the components of the complex impedance. The ECU 32 then calculates a ECI responsive to the values that is indicative of a degree of coupling between the electrode 12 and the tissue 16. The index may then be presented to a clinician in a variety of forms including by display on the display device 34 as, for example, the waveform 68, the meter 70, or the beacon 76.

An ECI formed in accordance with the teaching of the present invention may be useful in a variety of applications. As shown in the embodiment illustrated in FIG. 1, the ECI can be used as part of the system 10 for ablation of the tissue 16. The ECI provides an indication of the degree of electrical coupling between the tip electrode 12 and the tissue 16, thereby assisting in the safe and effective delivery of ablation energy to the tissue 16.

The ECI may further provide an indication of the proximity or orientation of the tip electrode 12 to the adjacent tissue 16. Referring to FIGS. 1 and 2, the signal source 61 of the sensing circuit 26 may generate excitation signals across source connectors SOURCE (+) and SOURCE (−) defined between the tip electrode 12 and the patch electrode 22, and also between the ring electrode 50 and the patch electrode 22. The impedance sensor 58 may then measure the resulting voltages across sense connectors SENSE (+) and SENSE (−)) defined between the tip electrode 12 and the patch electrode 20, and also between the ring electrode 50 and the patch electrode 22. In an exemplary embodiment, the measurements for the tip 12 and the ring 50 are taken at different frequencies or times. The ECU 32 may compare the measured values directly or, more preferably, determine an ECI for each of the electrodes 12, 50 responsive to the measured values, and compare the two ECIs. Differences between the measured impedance or ECI for the electrodes 12, 50 may indicate that the electrode 12 is disposed at an angle (as well as the degree of that angle) relative to the tissue 16.

It should be understood that the electrode 50 is used for exemplary purposes only. Similar results could be obtained with other electrodes disposed proximate the tip electrode 12 or from using a split tip electrode. For example, in another exemplary embodiment, the ECI may provide an indication of proximity or orientation of the catheter's tip to adjacent tissue by employing two or more electrodes near the tip. In one such embodiment, the tip electrode 12 is used together with and adjacent the ring electrode 50 to provide two independent measures of complex impedance and ECI. This is accomplished in the manner described with respect to FIGS. 1-3, but relies on separate SOURCE and SENSE circuits and connections that operate on different frequencies, or that are time division multiplexed to achieve independence. Cutaneous patch electrodes 20, 22 may be used in common for both tip and ring electrode impedance and ECU determinations. The ECU 32 may employ the two impedance measurements directly or operate on the difference of the impedances or ECIs. When in non-contact and of a defined proximity region, the tip and ring ECIs will both be constant and exhibit a fixed difference (depending on electrode design). Changes in this differential impedance or ECI reflect proximity of one (or both) electrodes to tissue. Once the tip electrode is in contact, the value of the differential ECI may indicate the angle of incidence of the catheter tip with tissue. Similar results could be obtained from other electrodes disposed near the tip electrode 12 or from using a split-tip electrode.

As briefly described above, the present invention may also be used as a proximity sensor to assess or determine the proximity of the electrode 12 to the tissue 16, as well as to assess the formation of lesions in the tissue 16. With respect to proximity assessment, as an electrode, such as the electrode 12, approaches the tissue 16, the impedance changes as does the ECI. The ECI is therefore indicative of the proximity of the electrode 12 to the tissue 16. In some applications, the general position (with a frame of reference) and speed of the tip of the catheter 14 and the electrode 12 are known (although the proximity of the electrode 12 to the tissue 16 is unknown). As will be described in greater detail below, this information can be combined to define a value (the "electrical coupling index rate" or ECIR) that is indicative of the rate of change in the ECI as the electrode 12 approaches the tissue 16 and which may provide an improved measure of the proximity of the electrode 12 to the tissue 16. This information can be used, for example, in robotic catheter applications to slow the rate of approach prior to contact, and also in connection with a transseptal access sheath having a distal electrode to provide an indication that the sheath is approaching (and/or slipping away from) the septum.

Figure 7:
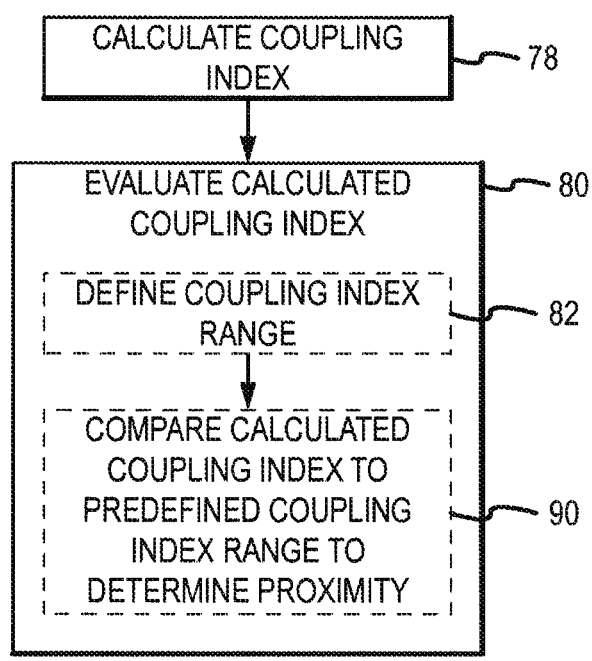
FIG. 7 is a flow diagram illustrative of an exemplary embodiment of a method for assessing the proximity of an electrode to tissue in accordance with present teachings.

In exemplary embodiment, the raw calculated ECI may be used to assess the proximity of the electrode 12 to the tissue 16. This particular embodiment provides a relatively simple discrimination of proximity. The ECU 32 calculates the ECI as described in detail above. The calculated ECI may then be used to assess the proximity of the electrode 12 to the tissue 16. FIG. 7 illustrates an exemplary embodiment of a method for assessing the proximity using the ECI.

In this particular embodiment, a current ECI is calculated in a first step 78. In a second step 80, the calculated ECI is evaluated to determine whether the electrode 12 is within a predetermined distance from the tissue 16, in contact with the tissue 16, or further away from the tissue 16 than the predetermined distance. More particularly, in a first substep 82 of second step 80, an ECI range 84 is defined that correlates to a predetermined distance from the tissue 16. In an exemplary embodiment provided for illustrative purposes only, the predetermined distance is 2 mm, and so the ECI range 84 has a first threshold value 86 that corresponds to 0 mm from the tissue 16 (i.e., the electrode is in contact with the tissue), and a second threshold value 88 that corresponds to location that is 2 mm from the tissue 16. These thresholds may be set by either preprogramming them into the ECU 32, or a user may input them using a conventional I/O device. In a second substep 90 of second step 80, the calculated ECI is compared to the predefined ECI range 84. Based on this comparison, the relative proximity of the electrode 12 is determined.

More particularly, if the calculated ECI is within the range 84, then the electrode 12 is deemed to be in "close proximity" of the tissue 16. In this particular embodiment, if the electrode is within 0-2 mm of the tissue, it is deemed to be in "close proximity." If the calculated ECI falls below the first threshold value 86, then the electrode 12 is deemed to be in contact with the tissue 16. Finally, if the calculated ECI falls outside of the second threshold value 88, then the electrode 12 is deemed to not be in close proximity of the tissue 16, but rather is further away than the predetermined distance, which, in this embodiment would mean that the electrode 12 is further than 2 mm from the tissue 16. It should be noted that a range of 0-2 mm is used throughout as the range corresponding to "close proximity." However, this range is provided for exemplary purposes only and is not meant to be limiting in nature. Rather, any other ranges of distance from the tissue 16 may be used depending on the application.

Figure 8A:
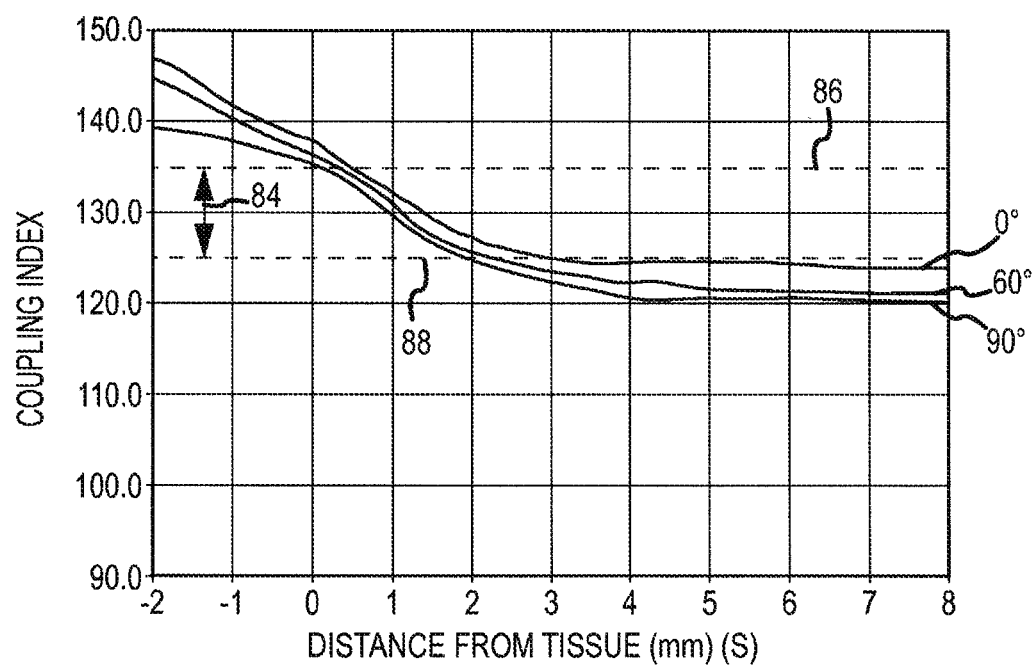
FIGS. 8a and 8b are charts illustrating the relationship of electrical coupling index (ECI) as a function of distance from tissue.
Figure 8B:
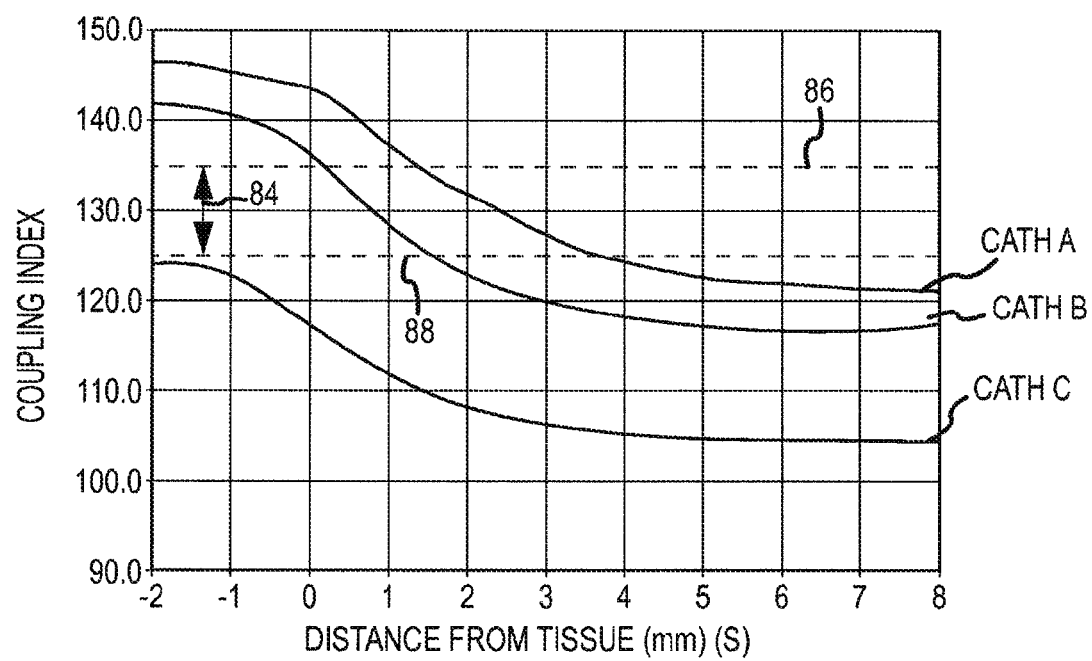

FIGS. 8a and 8b are provided to illustrate how the above described methodology may be applied. FIG. 8a illustrates examples of the results of ECI calculations that are meant to correspond to calculations representing three different angles of approach—0, 60, and 90 degrees—of the electrode 12 to the tissue 16. FIG. 8b illustrates examples of the results of ECI calculations that are meant to correspond to calculations resulting from the use of different types of catheters (i.e., CATH A, CATH B, and CATH C), which may influence the ECI calculations. It should be noted that the illustrated calculations do not correspond to actual test data or calculations made during an actual procedure, but rather are provided solely for illustrative purposes. In this example, the predetermined distance from the heart that is deemed to be "close proximity" was 0 to 2 mm.

As seen in FIG. 8a, in this particular example, the calculations for each angle of approach are fairly consistent with each other. As such, a single ECI range 84 may be defined that can be compared to any calculated ECI regardless of the angle of approach. In this particular example, the ECI range 84 is defined by the first threshold 86 having a value of 135, which corresponds to 0 mm from the tissue 16, and the second threshold 88 having a value of 125, which corresponds to 2 mm from the tissue 16. When the electrode is more than approximately 2 mm away from the tissue 16, the ECI is below 125, the second threshold 88 of the ECI range 84, and is relatively stable. As the electrode 12 approaches the tissue 16, however, the ECI begins to increase. When the electrode 12 is approximately 2 mm away, the ECI is around 125, which, again, is the second threshold 88 of the ECI range 84. As the electrode 12 continues to get closer the tissue 16, and therefore in closer proximity to the tissue 16, the ECI continues to increase. When the electrode 12 reaches the tissue 16 and makes contact, the ECI is at the first threshold 86 of approximately 135.

With respect to FIG. 8b, in this particular example, the illustrated calculations are spaced apart, as opposed to being closely grouped together. As such, a single ECI range 84 cannot be defined that would allow for the comparison with any calculated ECI. A number of factors may contribute to the spacing out of the calculations. For example, the type of catheter used, the particular environment in which the calculations are made, attributes of the patient, etc. may all contribute to the resulting spacing out of the calculations. To compensate for such factors, an offset is used. More particularly, if one or more contributory factors are present, the clinician is able to enter such information into the ECU 32 via a user interface for example, which will then be configured to add or subtract a defined offset from one or both of the calculated ECI and/or the ECI range. In an exemplary embodiment, ECU 32 may be programmed with one or more offsets, or the offset(s) may be entered by a user using a conventional I/O interface. Accordingly, in one exemplary embodiment, rather than simply comparing the ECI to an ECI range, an offset is added to or subtracted from either the ECI range, or the calculated ECI itself. In either instance, the added or subtracted offset performs a scaling function that allows for the comparison described above to be made.

In the particular example illustrated in FIG. 8b, the ECI range 84 is a baseline ECI range defined by the first threshold 86 having a value of 135, which corresponds to 0 mm from the tissue 16, and the second threshold 88 having a value of 125, which corresponds to 2 mm from the tissue 16. If the particular procedure is one in which an offset would apply, the ECU 32 makes the necessary adjustments, and then the methodology continues as described above with respect to FIG. 7. When the electrode is more than approximately 2 mm away from the tissue 16, the ECI is below 125, the second threshold 88 of the ECI range 84, and is relatively stable. As the electrode 12 approaches the tissue 16, however, the ECI begins to increase. When the electrode 12 is approximately 2 mm away, the ECI is around 125, which, again, is the second threshold 88 of the ECI range 84. As the electrode 12 continues to get closer the tissue 16, and therefore in closer proximity to the tissue 16, the ECI continues to increase. When the electrode 12 reaches the tissue 16 and makes contact, the ECI is at the first threshold 86 of approximately 135.

Accordingly, by knowing the ECI (whether as calculated and/or with an offset) and comparing it to the ECI range representing a predetermined distance from the tissue 16 (which may include an offset depending on the circumstances), one can easily determine whether the electrode 12 is in contact with, in close proximity to, or far away from the heart tissue 16.

In another exemplary embodiment, rather than comparing a calculated finite ECI to a predefined range, the rate of change of the ECI $$\left(\text{i.e., } \frac{dECI}{dt}\right)$$

may be evaluated and used to assess the proximity of the electrode 12 to the tissue 16. When the electrode 12 is within a predetermined distance from the tissue 16, the rate of change of the ECI or the change in the slope between ECIs over a predetermined amount of time $$\left(\text{i.e., } \frac{d^2 ECI}{dt^2}\right)$$

is most evident, and therefore, the rate of change in the ECI is greater than when either in contact with or far away from the tissue 16. Accordingly, it follows that when the rate of change of the ECI over a predetermined period of time is within a certain range or equals a particular rate, one may be able to determine whether the electrode 12 is within a predetermined distance or in close proximity to the tissue 16.

Figure 9:
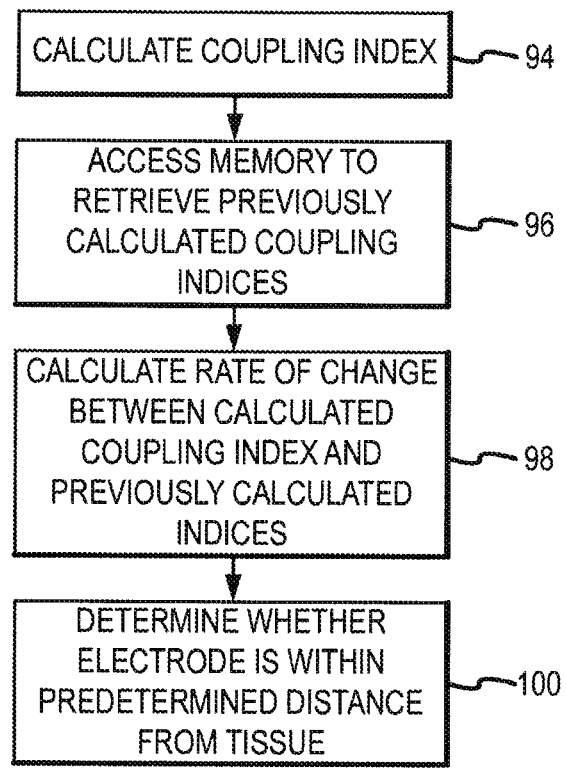
FIG. 9 is a flow diagram illustrative of another exemplary embodiment of a method for assessing the proximity of an electrode to tissue in accordance with present teachings.

FIG. 9 illustrates one exemplary embodiment of a methodology that uses the rate of change of the ECI. In this embodiment, a storage medium 92 (i.e., memory 92) is provided to store a predetermined number of previously calculated ECIs. The memory 92 may be part of the ECU 32 (See FIG. 1), or may be a separate component (or part of another component) that is accessible by the ECU 32 such that the ECU 32 may retrieve the stored ECIs. In an exemplary embodiment, the ECU 32 is configured to access the memory 92 and to calculate the rate of change in the ECI or the slope of a line drawn between a current or most recent ECI calculation and one or more previously calculated ECIs. If the rate of change or slope meets a predetermined value or falls within a predetermined or predefined range, then the ECU 32 will recognize that the ECI has changed at a certain rate, and therefore, that electrode 12 is within a certain distance of the tissue 16.

Accordingly, with specific reference to FIG. 9, in a first step 94 of this particular embodiment, a current ECI is calculated. In a second step 96, the ECU 32 accesses the memory 92 to retrieve one or more previously calculated ECIs. In a third step 98, the rate of change/slope between the current ECI and the one or more previously calculated ECIs is calculated. In a fourth step 100, the ECU 32 determines whether the electrode 12 is in close proximity to the tissue 16 based on the rate of change in the ECI.

This embodiment is particularly useful because the raw ECI is not being directly compared to a range of ECIs. Rather, because it is a rate of change or slope calculation, it does not matter what the magnitude of the ECI is, as it is the rate of change of the ECI that is being evaluated. Accordingly, it provides a more normalized approach for assessing proximity.

In an exemplary embodiment, whether the system 10 uses the raw ECI or the rate of change of the ECI to assess proximity, the system 10 is further configured to provide an indication to the clinician manipulating the catheter 14 or to a controller of a robotically controlled device that drives the catheter 14 that the electrode 12 is in "close proximity" to the tissue 16. In one exemplary embodiment, the ECU 32 is configured to generate a signal representative of an indicator that the electrode 12 is within the certain predetermined distance of the tissue 16 (e.g., 0-2 mm). In such an instance, this indicator indicates that the electrode 12 is in close proximity of the tissue 16 and allows the clinician or robotic controller to adjust its conduct accordingly (e.g., slow down the speed of approach). Such an indicator may be visually displayed on the display 34 of the system in the same manner described above with respect to the display of the ECI, may be displayed in a graphical form, may be in the form of an audible warning, or may comprise any other known indicators. With respect to robotic applications, the signal may be transmitted by the ECU 32 to a controller of the robotic device, which receives and processes the signal and then adjusts the operation of the robot as necessary. In other exemplary embodiments, the ECU 32 may also provide indicators that the electrode 12 is far away from the tissue 16 (i.e., further away than a predetermined distance), and/or that the electrode 12 is in contact with the tissue 16.

In another exemplary embodiment, the ECI may be used, in part, to calculate an electrical coupling index rate (ECIR). The resulting ECIR can, in turn, be used to assess the proximity of the electrode 12 to the tissue 16. In an exemplary embodiment, the ECU 32 is configured to calculate the ECIR, however, in other exemplary embodiments other processors or components may be used to perform the calculation. As will be described below, this particular embodiment provides a graded level of proximity.

In simple terms, the ECIR is calculated by dividing the change in ECI by the change in distance or position of the electrode 12 over a predetermined period of time. More specifically, the ECIR is calculated using the following equation (4):

$$ECIR := \frac{dECI}{ds} = \frac{dECI/dt}{ds/dt} \quad (4)$$

where "s" is the length of the path of the electrode in three-dimensional space (i.e., change in distance or position). The change in the ECI is calculated by sampling the ECI calculations performed by the ECU 32 (these calculations are described in great detail above) at a predetermined rate and then determining the difference between a current calculation and the most recent previous calculation, for example, that may be stored in a storage medium that is part of accessible by the ECU 32. In another exemplary embodiment, however, the difference may be between a current calculation and multiple previous calculations, or an average of previous calculations.

In an exemplary embodiment, the ECU 32 samples the calculated ECI every 10 to 30 ms, and then calculates the change in the ECI over that time interval $$\left(\text{i.e., } \frac{d^2 ECI}{dt^2}\right).$$

It will be appreciated by those of ordinary skill in the art that the ECI may be sampled at rates other than that described above, and that such rates are provided for exemplary purposes only. For example, in another exemplary embodiment, using techniques well known in the art, the sampling is timed or synchronized to coincide with the cardiac cycle so as to always sample at the same point in the cardiac cycle, thereby avoiding variances due to the cardiac cycle. In another exemplary embodiment, the sampling of the ECI is dependent upon a triggering event, as opposed to being a defined time interval. For example, in one exemplary embodiment, the sampling of the ECI is dependent upon the change in the distance/position of the electrode 12 meeting a particular threshold. More particularly, when the system 10 determines that the electrode has moved a predetermined distance, the ECU 32 will then sample the ECI over the same period of time in which the electrode 12 moved. Accordingly, it will be appreciated by those of ordinary skill in the art that many different sampling rates and/or techniques may be employed to determine the change in the ECI.

With respect to the change in the distance (or position/location) of the electrode, this change may be calculated by the ECU 32 based on location coordinates provided to it by the system 30 (i.e., x, y, z coordinates provided by the mapping, visualization, and navigation system 30), or may be calculated by the system 30 and then provided to the ECU 32. As with the change in ECI calculation, the change in distance or location is determined by sampling the location coordinates of the electrode 12 at a predetermined rate. From this, the change in distance over time $$\left(\text{i.e., } \frac{ds}{dt}\right)$$

can be derived. In an exemplary embodiment, the location coordinates of the electrode 12 are sampled every 10 to 30 ms, and then the change in the location is calculated over that time interval. It will be appreciated by those of ordinary skill in the art that the location/position of the electrode may be sampled at rates other than that described above, and that such rates are provided for exemplary purposes only. For example, in another exemplary embodiment, using techniques well known in the art, the sampling is timed or synchronized to coincide with the cardiac cycle so as to always sample at the same point in the cardiac cycle, thereby avoiding variances due to the cardiac cycle.

Once these two "change" calculations are complete, the ECU 32 is able to calculate the ECIR by dividing the change in the ECI by the change in the distance or location of the electrode 12

$$\left(\text{i.e., } \frac{d^2 ECI}{dt^2}\right).$$

In an exemplary embodiment, the calculated ECIR is saved in a storage medium that is accessible by the ECU 32.

Figure 10:
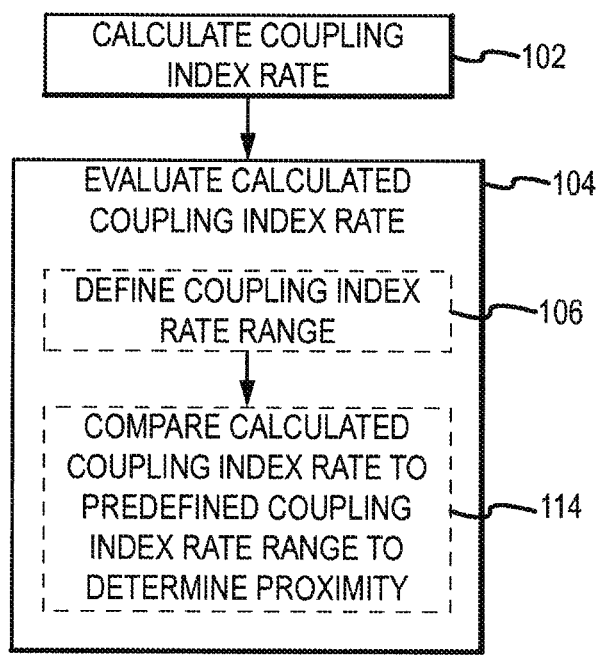
FIG. 10 is a flow diagram illustrative of yet another exemplary embodiment of a method for assessing the proximity of an electrode to tissue in accordance with present teachings.

Once the ECIR has been calculated, it may be used to assess, among other things, the proximity of the electrode 12 to the tissue 16. In an exemplary embodiment illustrated in FIG. 10, the ECIR is calculated in a first step 102. In a second step 104, the calculated ECIR is evaluated to determine whether the electrode 12 is within a predetermined distance from the tissue 16, in contact with the tissue 16, or further away from the tissue 16 than the predetermined distance.

More particularly, in a first substep 106 of step 104, a ECIR range 108 is defined that correlates to a predetermined distance from the tissue 16. In an exemplary embodiment provided for illustrative purposes only, the predetermined distance is 2 mm, and so the ECIR range 108 has a first threshold value 110 that corresponds to 0 mm from the tissue 16 (i.e., the electrode 12 is in contact with the tissue 16), and a second threshold value 112 that corresponds to a location that is 2 mm from the tissue 16. These thresholds may be set by either preprogramming them into the ECU 32, or a user may manually input them into the ECU 32 using a conventional I/O device.

In a second substep 114 of second step 104, the calculated ECIR is compared to the predefined range 108 of ECIRs. Based on this comparison, the relative proximity of the electrode 12 is determined. More particularly, if the calculated ECIR is within the range 108, then the electrode 12 is deemed to be in "close proximity" of the tissue 16. In this particular embodiment, if the electrode 12 is within 0-2 mm of the tissue 16, it is deemed to be in "close proximity." If the calculated ECIR falls below the first threshold value 110, then the electrode 12 is deemed to be in contact with the tissue 16. Finally, if the calculated ECIR falls outside of the second threshold value 112, then the electrode 12 is deemed to not be in close proximity of the tissue 16, but rather is further away than the predetermined distance, which, in this embodiment would mean that the electrode 12 is further than 2 mm from the tissue 16.

Figure 11:
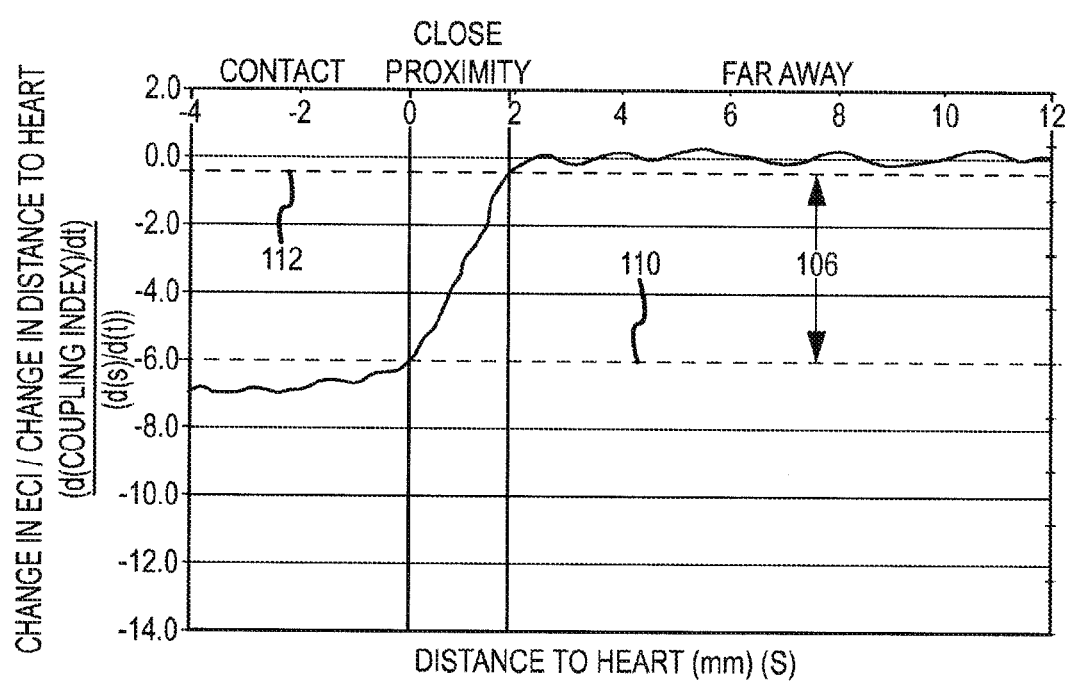
FIG. 11 is a chart illustrating the relationship of electrical coupling index rate (or ECIR) as a function of distance from tissue.

FIG. 11 is provided to show how the above described methodology may be applied, and illustrates what a ECIR calculation may look like. It should be noted that the illustrated calculations are not based on actual testing or ECIR calculations made during an actual procedure, but rather are provided solely for illustrative purposes. In this particular example, the ECIR range 108 is defined by a first threshold 110 having a value of −6.0, which corresponds to 0 mm from the tissue 16, and a second threshold 112 having a value of −0.5, which corresponds to 2 mm from the tissue 16. In this particular example, the predetermined distance from the heart that is deemed to be "close proximity" is 0-2 mm. It should be noted that the ECIR becomes negative as the tissue 16 is approached because as the electrode 12 comes closer to the tissue 16, the ECI increases. Accordingly, the value representing the change in ECI is negative since a higher ECI is subtracted from a lower ECI.

As seen in FIG. 11, in this example, when the electrode 12 is more than approximately 2 mm away from the tissue 16, the ECIR is close to zero (0) and relatively stable, but more particularly hovering between −0.5 and +0.5. This is partly because the further away from the tissue 16 the electrode 12 is, the ECIR is less responsive. However, as the electrode 12 approaches the tissue 16, the ECIR begins to decrease and becomes dramatically more dynamic. When electrode is approximately 2 mm away, the ECIR is around −0.5, which is the second threshold 112 of the ECIR range 108. As the electrode 12 continues to get closer the tissue 12, and therefore in closer proximity thereto, the ECIR continues to decrease. In this example, when the electrode 12 reaches the tissue 16 and makes initial contact, the ECIR is at −6.0, which is the first threshold 110 of the ECIR range 108. The ECIR then begins to stabilize at a level around −7.0 that is much lower than the level when the electrode is "far away" from the tissue (i.e., more than 2 mm) and outside of the predetermined ECIR range 108.

Accordingly, by knowing the ECIR and comparing that rate to a predefined ECIR range representing a predetermined distance from the tissue 16, one can easily determine whether the electrode 12 is in contact with, in close proximity to, or far away from the tissue 16.

Figure 12:
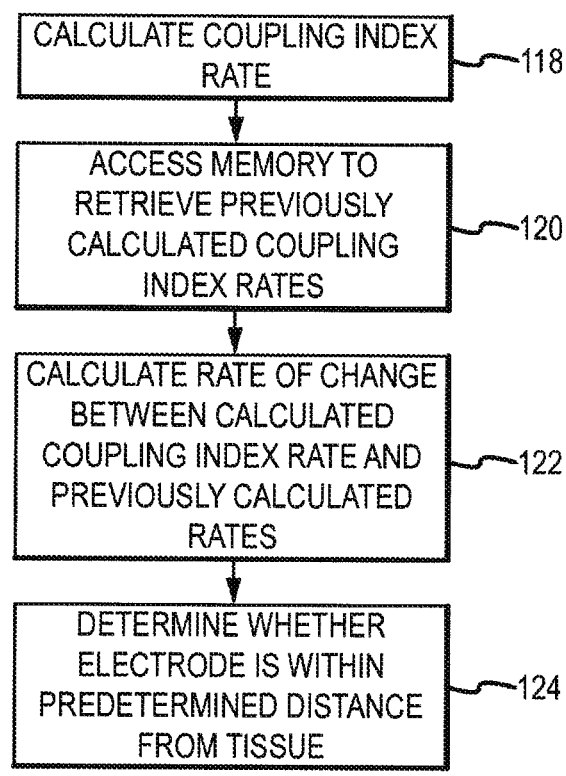
FIG. 12 is a flow diagram illustrative of yet another exemplary embodiment of a method for assessing the proximity of an electrode to tissue in accordance with present teachings.

With reference to FIG. 12, another exemplary embodiment of a method for assessing the proximity using the ECIR will be described. In this particular embodiment, rather than comparing a calculated finite ECIR to a predefined range, the rate of change of the ECIR $$\left(\text{i.e., } \frac{d}{dt}\left(\frac{dECI}{ds}\right) \text{ or } \frac{d^2 ECI}{ds^2}\right)$$

is evaluated. It will be appreciated by those of ordinary skill in the art that the rate of change in the ECIR may be with respect to time or space. Accordingly, both the temporal and spatial approaches will be described below. By evaluating the rate of change in the ECIR, a more robust and accurate proximity assessment can be performed.

More specifically, when the electrode 12 is within a predetermined distance from the tissue 16, the rate of change in the ECIR, or change in the slope between ECIRs over a predetermined period of time, is greater than when the electrode 12 is either in contact with or far away from the tissue 16. (See FIG. 11, for example). Accordingly, it follows that when the rate of change of the ECIR over a predetermined period of time is within a certain range or equals particular rate that may be preprogrammed into the ECU 32 or input by a user as described above, one may be able to determine whether the electrode is within a predetermined distance or in close proximity to the tissue. The methodology of this particular embodiment may carried out using either one of the calculations represented by equation (5) or equation (6) below:
(5) Rate of Change of $$ECIR = \frac{d}{dt}\left(\frac{dECI}{ds}\right)$$

(6) Rate of Change of $$ECIR = \frac{d/dt(dECI/ds)}{ds/dt} = \frac{d^2 ECI}{ds^2}$$

With reference to FIG. 12, in an exemplary embodiment, the rate of change in the ECIR may be determined by simply calculating the change between two or more ECIR calculations (i.e., equation (5) above). In such an embodiment, a storage medium 116 (i.e., memory 116) is provided to store a predetermined number of previously calculated ECIRs. The memory 116 may be part of the ECU 32 (See FIG. 1), or may be a separate component (or part of another component) that is accessible by the ECU 32 such that the ECU 32 may retrieve the stored ECIRs. In an exemplary embodiment, the ECU 32 is configured to access the memory 116 and to calculate the rate of change of the ECIR or slope of a line drawn between a current or most recent ECIR calculation and one or more prior ECIR calculations. If the rate of change or slope meets a predetermined value or falls with a predetermined range, then the ECU 32 will recognize that the ECIR has changed a certain amount, and therefore, that electrode 12 is within a certain distance of the tissue 16.

Accordingly, with reference to FIG. 12, in a first step 118 of this particular embodiment, a current ECIR is calculated. In a second step 120, the ECU 32 accesses the memory 116 to retrieve one or more previously calculated ECIRs. In a third step 122, the rate of change or the slope between the current ECIR and one or more previously calculated ECIRs is calculated. In a fourth step 124, the ECU 32 determines whether the electrode 12 is in close proximity to the tissue 16 based on the rate of change in the ECIR.

In another exemplary embodiment of a methodology based on a rate of change in ECIR, small changes in the location or position of the electrode 12, and therefore, the corresponding rate of change of the corresponding ECIR, can be taken advantage of to obtain a substantially continuous and robust assessment of proximity between the electrode 12 and the tissue 16.

More particularly, perturbations can be induced or instigated in the position of the electrode 12 either manually by a clinician or by way of a robotic controller. These small changes in position of the electrode 12 (e.g., on the order of 0.2 mm) can be measured by system 30, as described above, and processed, at least in part, with the corresponding change in the ECI and the change in position of the electrode 12 by the ECU 32, for example, to calculate the rate of change of the ECIR. The frequency of these perturbations may be sufficiently high to allow for the effective filtering or smoothing out of errors in the ECIR calculations. This may be beneficial for a number of reasons, such as, for example, to resolve environmental events such as cardiac cycle mechanical events. In such an instance, the perturbation frequency would be higher than the frequency of the cardiac cycle. In one exemplary embodiment, the frequency of the perturbations is five to ten perturbations per second. Accordingly, the cardiac frequency may be filtered out of, or compensated for, in the calculations so as to smooth out any changes resulting during the cardiac cycle because of the constant movement of the electrode.

Alternatively, if the perturbations occur less frequently, the inducement of the perturbations may be synchronized with or coordinated to occur at one or more points in the cardiac cycle using known methodologies. By doing so, the filtering or smoothing effect described above may be carried out and also allow for the observation of proximity changes as a result of catheter or electrode movement/manipulation or ventilation, for example. Accordingly, the inducement of perturbations and the resulting ECIR resulting from such perturbations can be used to filter or smooth variation in signals resulting from cardiac cycle mechanical events, thereby providing a more robust system.

Accordingly, in this particular aspect of the invention, fast perturbations of the catheter, and therefore, the electrode, permit frequent determinations of ECIR. At a separate and slower time scale, motions of the catheter and the electrode towards or away from the tissue permit a filtered derivative of ECIR. Changes over this longer time scale of the gradual distance toward or away from the tissue allow for a good determination of a second spatial derivative of ECI $$\left(\text{i.e., } \frac{d^2 ECI}{ds^2} = \frac{d/dt(ECIR)}{ds/dt}\right).$$

Figure 13:
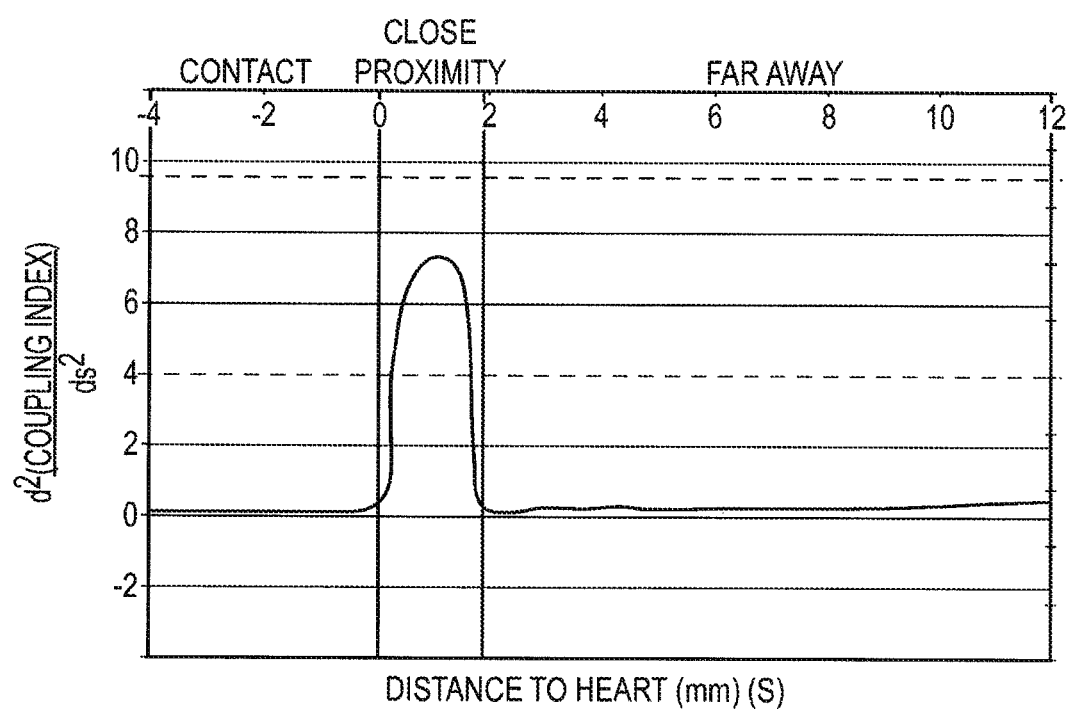
FIG. 13 is a chart illustrating an example employing a method of proximity assessment involving a two-time scale approach.

Accordingly, this particular methodology represents a two time-scale approach (i.e., fast perturbations of the electrode 12 combined with slow movement of the electrode 12 towards the tissue 16). FIG. 13 illustrates an exemplary representation of what the output of this methodology looks like, which provides a sound representation of proximity. Such a methodology results in a more robust discriminator of proximity.

Whether the calculated ECIR is compared to a predetermined range of ECIRs, or the rate of change of the ECIR is evaluated to assess the proximity of the electrode 12 to the tissue 16, in an exemplary embodiment, the system 10 may provide an indication to the clinician manipulating the catheter 14 or to a controller of a robotically controlled device driving the catheter 14 that the electrode is in "close proximity" to the tissue 16. In one exemplary embodiment, the ECU 32 is configured to generate a signal representative of an indicator that the electrode 12 is within the certain predetermined distance of the tissue 16 (e.g., 0-2 mm). In such an instance, this indicator indicates that the electrode 12 is in close proximity to the tissue 16 and allows the clinician or robotic controller to adjust its conduct accordingly (e.g., slow down the speed of approach). Such an indicator may be visually displayed on the display 34 of the system in the same manner described above with respect to the display of the ECI, may be displayed in graphical form, may be in the form of an audible warning, or may comprise any other known indicators. With respect to robotic applications, the signal may be transmitted by the ECU 32 to a controller from the robotic device, which receives and processes the signal and then adjusts the operation of the robot as necessary. In other exemplary embodiments, the ECU 32 may also provide indicators that the electrode 12 is far away from the tissue (i.e., further away than a predetermined distance), and/or that the electrode 12 is in contact with the tissue.

Additionally, whether the ECI or the ECIR are used to determine or assess the proximity of the electrode to the tissue, in an exemplary embodiment, the ECU 32 is programmed with a computer program (i.e., software) encoded on a computer storage medium for assessing and/or determining the proximity of the electrode 12 to the tissue 16. In such an embodiment, the program generally includes code for calculating a ECI responsive to values for first and second components of the complex impedance between the catheter electrode 12 and the tissue 16, and also code to process ECI in the various ways described above (i.e., comparison of ECI to a predefined range, calculating ECIRs and comparing calculated ECIR to predefined ranges, calculating rate of change in the ECI and evaluating the same, and calculating rate of change in ECIR and evaluating the same, for example).

In accordance with another aspect of the invention, ECI (as well as other similar indices described in greater detail below) can be used to assess the formation of lesions in tissue—and more specifically, whether a particular area of tissue at a particular location has been changed (e.g., ablated)—as a result of an ablation procedure. In the context of ablation, in an exemplary embodiment, tissue may be deemed to be "changed," for example, when a transmural lesion is formed in the tissue. Alternatively, tissue may be deemed to be unchanged, or at least not sufficiently changed, when no lesion is formed or a lesion is started but not fully formed in the tissue (e.g., the lesion is not transmural). Tissue that has been changed, such as, for example, ablated tissue or scar tissue, can have different electrical and functional properties than otherwise similar unchanged, or at least not sufficiently changed (e.g., unablated or not fully ablated), or virgin tissue. As such, the capacitive and resistive properties of changed tissue are likewise different than that of otherwise similar unchanged tissue, and therefore, the ECI, for example, of changed tissue is also different than otherwise similar unchanged or insufficiently changed tissue. More specifically, the ECI of changed (e.g., ablated) tissue is lower than that of otherwise similar unchanged or not sufficiently changed (e.g., unablated or not fully ablated) tissue. Accordingly, in an exemplary embodiment, the catheter 14, and one or more electrodes thereof, such as, for example, electrode 12, in contact with an area of tissue is moved manually by a physician/clinician or through automation by a robotic system, for example, along or across the tissue (i.e., along the longitudinal axis of the tissue or laterally relative to the longitudinal axis) and ECI calculations are made by the ECU 32 in the same manner described in great detail above. The ECI calculations may then be evaluated and/or processed to enable a determination to be made as to whether the particular area or portion of tissue in contact with the electrode 12 has been changed (e.g., ablated) to such an extent to cause a change in the ECI. It may also be necessary to evaluate the ECI calculation in light of contact readings, force readings, or some other readings to fully evaluate whether the tissue has changed.

For example, in an exemplary embodiment, it can be determined whether a lesion line created during an ablation procedure is contiguous or whether there are gaps therein that may or may not require additional ablation. This can be accomplished by dragging the electrode 12 along the perceived lesion line created during an ablation procedure, or back and forth across a perceived lesion line, and then processing/evaluating ECI calculations made at various points. The processing can determine if a lesion is present in a number of ways. For example, the ECI values calculated for a particular location can be compared to a preset value (e.g., a value set by prior clinical experience, by an operator, or by values taken during the current procedure) to determine if a lesion is present. Likewise, the calculated ECI values could be compared to a previously taken ECI value at that particular location. Similarly, changes in ECI over time and/or distance, or a rate of change in ECI values during an ablation procedure, could be considered. Alternatively, the ECU 32 can utilize multiple methods to identify a lesion.

Figure 14A:
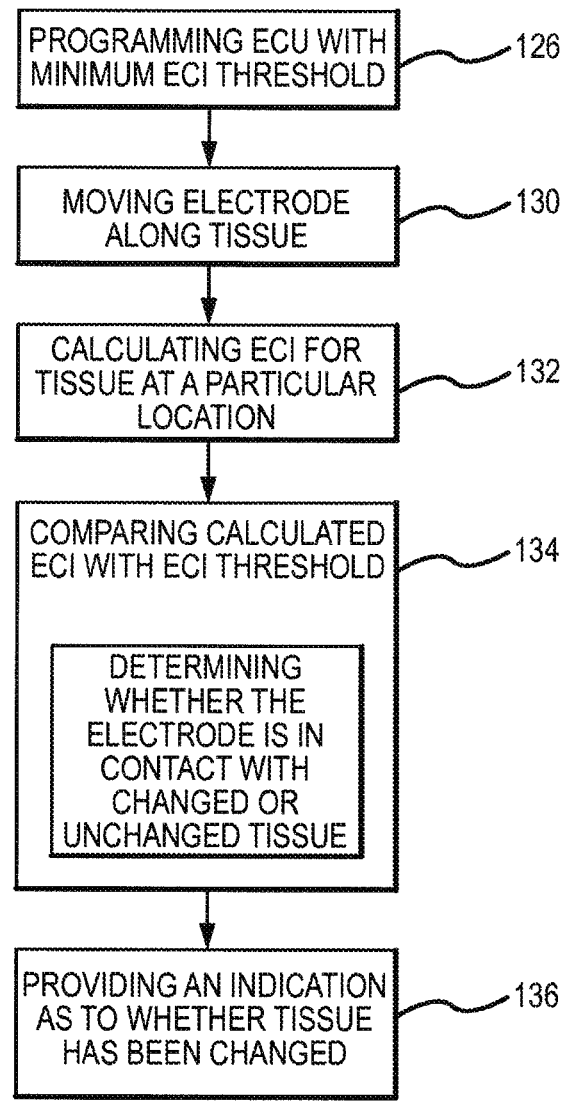
FIGS. 14a-20b are flow diagrams illustrative of a various exemplary embodiments of ECI-based methods for lesion assessment in tissue in accordance with the present teachings.

With reference to FIG. 14a, an exemplary embodiment of a method of ECI-based lesion assessment is illustrated. In a first step 126, the ECU 32 is programmed with a predetermined minimum ECI threshold 128 that represents the minimum ECI level for which contact between the electrode 12 and unchanged or not sufficiently changed (e.g., unablated or not fully ablated) tissue is attained. The ECU 32 may be preprogrammed with the threshold 128 or a user may input the threshold 128 via a conventional I/O interface, thereby allowing the threshold 128 to be changed. In a second step 130, while maintaining contact with the tissue, the electrode 12 is moved along or about an area of tissue that was, for example, subjected to an ablation procedure. In one exemplary application, the area of tissue may be a lesion line created during an ablation procedure, and a clinician/physician is dragging the electrode 12 along or across the lesion line to determine whether there are gaps in the lesion line that may require additional ablation. It should be noted, however, that the present invention is not limited solely to this particular application. Rather, any number of lesion or scar tissue assessment applications (such as, for example, assessing lesion size rather than gap detection, determining scar tissue borders, etc.) remain within the spirit and scope of the present invention.

As the electrode 12 is moved, in a third step 132, an ECI calculation is made. Once the ECI calculation is made it can be used in any number of ways. In one exemplary embodiment, the ECU 32 is configured to compare the ECI calculation to the ECI threshold 128, and in a fourth step 134, the ECU 32 makes such a comparison. If the calculated ECI value meets or exceeds the threshold 128, a determination can be made that the tissue at the particular location at which the ECI calculation was made has not changed, or at least not sufficiently changed (e.g., the tissue has not been ablated or not fully ablated), since the calculated ECI is above the minimum ECI value. If, on the other hand, the calculated ECI value is below the threshold 128, a determination can be made that the tissue at the location at which the ECI calculation was made has changed (e.g., the tissue has been ablated), since the calculated ECI is below the minimum ECI value corresponding to contact with unchanged tissue.

In a fifth step 136, an indication is provided to the clinician/physician as to whether the tissue that is in contact with the electrode 12 has changed. Accordingly, the ECU 32 is configured to generate a signal representative of an indicator that the electrode 12 is in contact with tissue that has or has not been changed (e.g., ablated tissue if the change meets certain quantitative standards, or unablated or not fully ablated tissue if the tissue is unchanged or not sufficiently changed) based on the ECI calculation and comparison. The indicator may take many forms. For example, the indicator may be displayed on the display monitor 34. Such a displayed indicator may include, for exemplary purposes only, displaying the actual ECI calculation on the monitor, a graphical representation, or the illumination/de-illumination or changing color of a beacon on the monitor. In other embodiments, the indicator may take the form of an audible alert, a visible indication on the catheter handle, haptic feedback, or any other indicators known in the art. In a robotics-based system, the indicator may take the form of a signal provided to a robotic controller. In still other embodiments the feedback can take the form of an indication placed on an anatomical map that is displayed on the display monitor 34, for example, an electroanatomical map of the sort generated by the St. Jude Medical EnSite™ Electroanatomical Modeling System, the Biosense Webster Carto™ System, a fluoroscopy system, an MRI image, a CT scan, a magnetic location system such as the gMPS system from Mediguide Ltd., or another image of the subject tissue displayed on the display monitor 34 to indicate what portions of the tissue have been changed, and which portions have not. In an exemplary embodiment, a display monitor, such as, for example, the display monitor 34, may be configured to display an image or map thereon that may provide a visual display of the effectiveness of an ablation procedure as set forth in U.S. patent application Ser. No. 12/622,626 entitled "System and Method for Assessing Effective Delivery of Ablation Therapy," filed Nov. 20, 2009 in the name of Deno, et al., which is incorporated herein by reference in its entirety. The above described process is then repeated as the electrode continues to move.

Figure 14B:
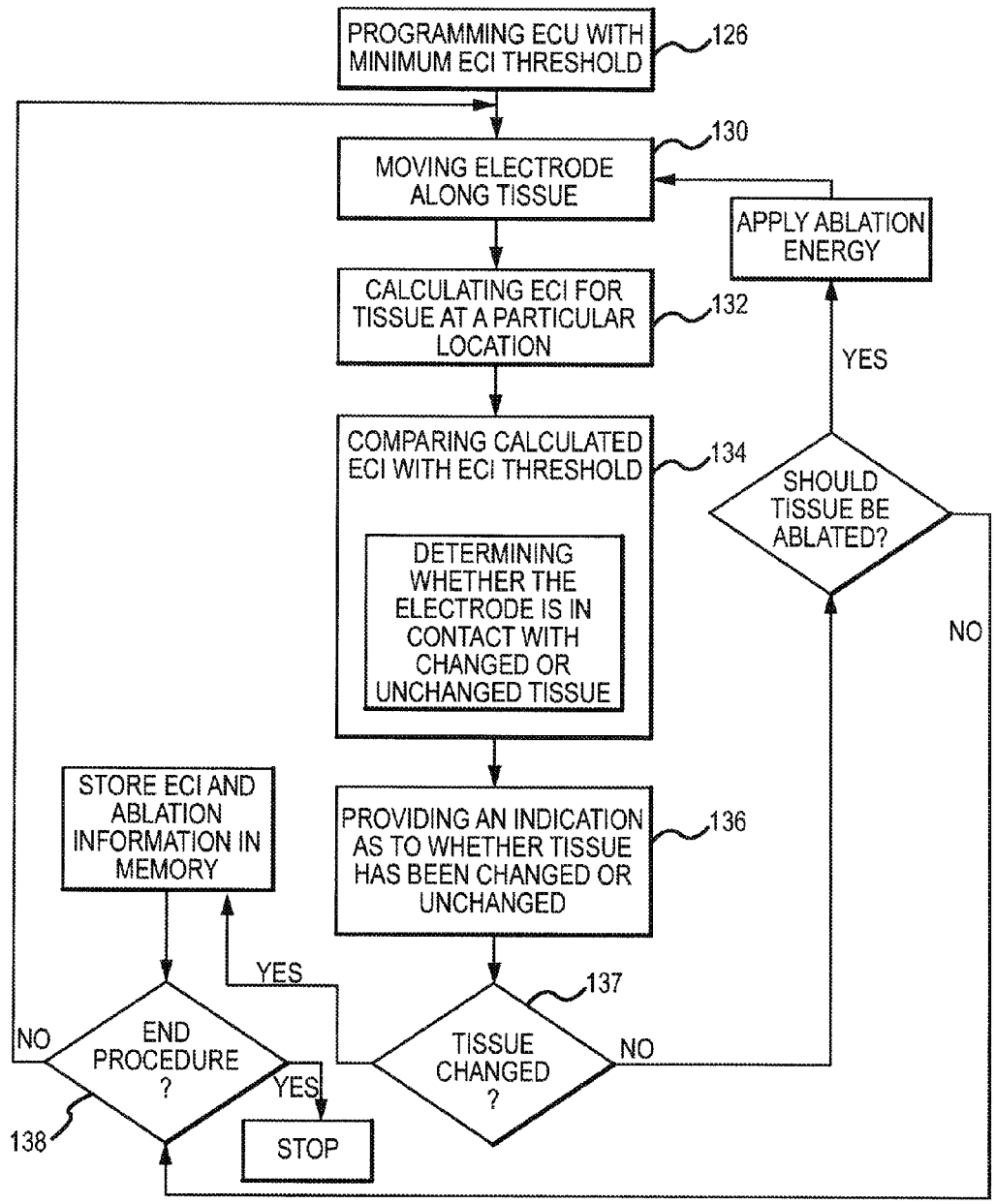

FIG. 14b depicts another exemplary embodiment of the method illustrated in FIG. 14a in which steps relating to an ablation procedure are included. For example, in a sixth step 137 a determination is made as to whether the portion of the tissue at the particular location that is being evaluated (i.e., the tissue that electrode 12 is in contact with) has been changed (e.g., ablated). In an exemplary embodiment, the particular location of the portion of the tissue is determined using the mapping, visualization, and navigation system 30.

If the tissue has been changed, the calculated ECI and ablation information may be stored in a storage medium, such as, for example, memory 92/116. In a seventh step 138, system 10 then determines whether the ablation procedure can be ended. If "yes," then the ablation procedure is stopped. If "no," then the process begins again at second step 130.

If the tissue has not been changed, or at least not sufficiently changed (e.g., the tissue is unablated or not fully ablated), then the physician/clinician can determine whether it should be ablated. Alternatively, in a robotic application, a robotic controller, or other component of the system, can make such a determination. If tissue should be ablated, ablative energy can be applied to the tissue at that particular location. Accordingly, the physician/clinician may move the catheter 14 to the particular location requiring ablation and then cause ablative energy to be applied. Alternatively, in a robotic application, the robotic controller may cause the catheter 14 to move to the particular location requiring ablation and then cause ablative energy to be applied. In such an embodiment, the system 30 may be used by the robotic controller to determine where the catheter is and where it needs to go, as well as to assist with the direction of the movement of the catheter 14 to the desired location. Once the tissue is ablated, the process may then proceed starting at step 130.

If the tissue should not be ablated, then the ECI and ablation information may be stored in a storage medium, such as, for example, memory 92/116. The system 10 then determines whether the ablation procedure can be ended. If "yes," then the ablation procedure is stopped. If "no," then the process begins again at second step 130.

Figure 15A:
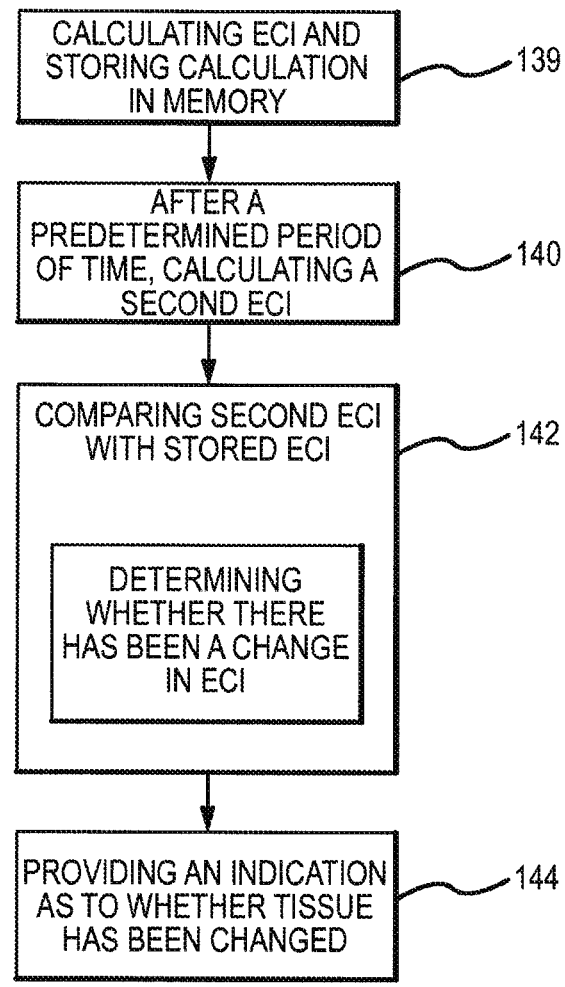

In another exemplary embodiment, rather than comparing a calculated ECI with an ECI threshold, the change in the ECI over either time or space (distance) is evaluated. In an exemplary embodiment, the change in ECI over a predetermined amount of time $$\left(\text{i.e., } \frac{dECI}{dt^2}\right)$$

is determined and evaluated. FIG. 15a illustrates an exemplary embodiment of a methodology based on change in ECI over time.

In a first step 139, an ECI calculation for a particular area of the tissue 16 is made and then stored in a storage medium, such as, for example, memory 92/116. In a second step 140, the ECU 32 calculates another ECI after a predetermined period of time has elapsed. This calculated ECI may correspond to the same area of the tissue 16 or a different area of the tissue 16. The ECU 32 may be programmed with the time interval or sampling rate that constitutes the predetermined period of time, or it may be entered by the user via a conventional I/O interface. In a third step 142, the ECU 32 compares the previously stored ECI calculation with the current ECI calculation and determines if there is a change, and if so, the degree of such a change. No change in ECI is indicative of the electrode remaining in contact with the same type of tissue (i.e., the electrode has not moved from unchanged or not sufficiently changed (e.g., unablated or not fully ablated) tissue to changed (e.g., ablated) tissue, or vice versa, and therefore, there is no appreciable change in ECI). A "positive" change value is indicative of the electrode 12 moving from contact with unchanged or not sufficiently changed tissue to changed tissue (i.e., higher ECI for unchanged or insufficiently changed (e.g., unablated or not fully ablated) tissue compared to lower ECI for changed (e.g., ablated) tissue results in a positive number). Finally, a "negative" change value is indicative of the electrode 12 moving from contact with changed tissue to unchanged or insufficiently changed tissue (i.e., lower ECI for changed (e.g., ablated) tissue compared to higher ECI for unchanged or insufficiently changed (e.g., unablated or not fully ablated) tissue results in a negative number).

In an instance where the comparison of the ECI calculations results in a change—whether positive or negative—in an exemplary embodiment, the degree of change may be taken into account such that the change must meet a predetermined threshold to be considered a change in contact from changed to unchanged or insufficiently changed tissue (or vice versa). This allows for some change in ECI without necessarily indicating a change in the tissue.

With continued reference to FIG. 15*a*, in a fourth step 144, an indication is provided to the clinician/physician, or to a robotic controller in a robotics-based system, as to whether the portion of the tissue that is presently in contact with the electrode 12 is changed (e.g., ablated) or unchanged or not sufficiently changed (e.g., unablated or not fully ablated) tissue. Accordingly, the ECU 32 is configured to generate signal representative of an indicator of the type of tissue the electrode 12 is in contact with based on the comparison of ECI calculations. The description set forth in great detail above relating to the generation and/or provision of indicators applies here with equal weight, and therefore, will not be repeated. This process repeats itself as the electrode 12 continues to move. Accordingly, each ECI calculation is saved in the memory 92/116 so that it may be compared to one or more subsequent ECI calculations.

Figure 15B:
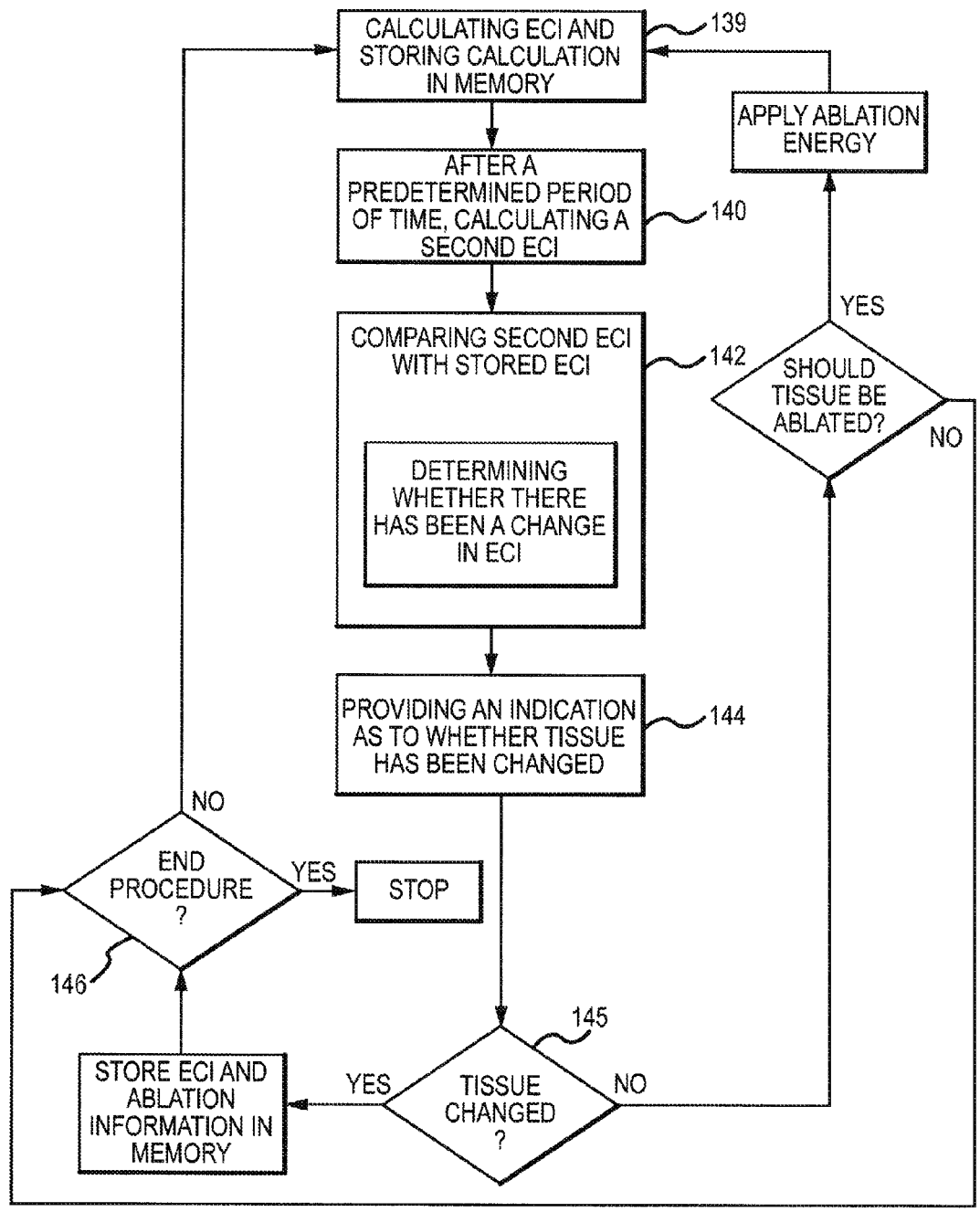

FIG. 15*b* depicts another exemplary embodiment of the method illustrated in FIG. 15*a* in which steps relating to an ablation procedure are included. For example, in a fifth step 145, a determination is made as to whether the tissue at the particular location that is being evaluated (i.e., the tissue that electrode 12 is in contact with) has been changed (e.g., ablated). If it has, the calculated ECI and ablation information may be stored in a storage medium, such as, for example, memory 92/116. In a sixth step 146, system 10 then determines whether the ablation procedure can be ended. If "yes," then the ablation procedure is stopped. If "no," then the process begins again at step 139.

If the tissue has not been changed, or at least not sufficiently changed (e.g., the tissue is unablated or not fully ablated), then the physician/clinician can determine whether it should be ablated. Alternatively, in a robotic application, a robotic controller can make such a determination. If tissue should be ablated, ablative energy can be applied to the tissue at that particular location. Accordingly, the physician/clinician may move the catheter 14 to the particular location requiring ablation and then cause the ablative energy to be applied. Alternatively, in a robotic application, the robotic controller may cause the catheter 14 to move to the particular location requiring ablation and then cause the ablative energy to be applied. In such an embodiment, the system 30 may be used by the robotic controller to determine where the catheter 14 is and where it needs to go, as well as to assist in the direction of the movement of the catheter 14 to the desired location. The process may then proceed starting at step 139. If the tissue should not be ablated, then the ECI and ablation information may be stored in a storage medium, such as, for example, memory 92/116. The system 10 then determines, whether the ablation procedure can be ended. If "yes," then the ablation procedure is stopped. If "no," then the process begins again at step 139.

Figure 16A:
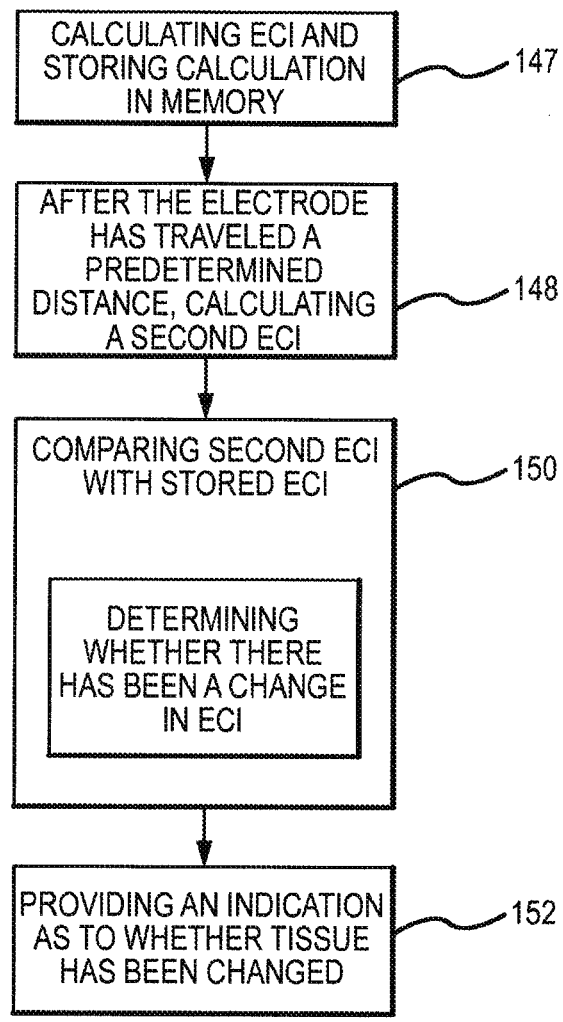

In another exemplary embodiment, besides comparing a calculated ECI with an ECI threshold or evaluating the change in the ECI over a predetermined time interval, the change in the ECI over a predetermined space or surface distance $$\left(\text{i.e., } \frac{dECI}{ds}\right)$$

is determined and evaluated. FIG. 16*a* illustrates an exemplary embodiment of a methodology based on change in ECI over distance or space.

In a first step 147, an ECI calculation is made for a particular area of the tissue 16 and then stored in a storage medium, such as, for example, memory 92/116. In a second step 148, the ECU 32 calculates another ECI calculation after it is determined that the electrode 12 has traveled a predetermined distance either longitudinally along the longitudinal axis of a lesion, or laterally relative to the longitudinal axis to another area of the tissue 16. In an exemplary embodiment, the ECU 32 is configured to receive location data (such as x, y, z coordinates) from the mapping, visualization, and navigation system 30 and to calculate change in distance relative to prior stored location data also received from system 30. In another exemplary embodiment, system 30 is configured to process the location data to calculate a change in distance and to provide the change to the ECU 32 for it determine whether the predetermined sampling distance has been met. Accordingly, the calculation may be triggered when the electrode moves a certain distance. The predetermined distance may be programmed into the ECU 32 or may be entered by a user via a conventional I/O interface.

In a third step 150, the ECU 32 compares the previously stored ECI calculation with the current ECI calculation and determines if there is a change, and if so, the degree of such a change. No change in ECI is indicative of the electrode remaining in contact with either changed or unchanged, or at least not sufficiently changed tissue (i.e., the electrode has not moved from unchanged or not sufficiently changed (e.g., unablated or not fully ablated) tissue to changed (e.g., ablated) tissue, or vice versa, and therefore, there is no appreciable change in ECI). A "positive" change value is indicative of the electrode 12 moving from contact with unchanged or insufficiently changed tissue to changed tissue (i.e., higher ECI for unchanged or not sufficiently changed (e.g., unablated or not fully ablated) tissue compared to lower ECI for changed (e.g., ablated) tissue results in a positive number). Finally, a "negative" change value is indicative of the electrode 12 moving from contact with changed tissue to unchanged, or at least not sufficiently changed tissue (i.e., lower ECI for changed (e.g., ablated) tissue compared to higher ECI for unchanged or insufficiently changed (e.g., unablated or not fully ablated) tissue results in a negative number).

In an instance where the comparison of the ECI calculations results in a change—whether positive or negative—in an exemplary embodiment the degree of change may be taken into account such that the change must meet a predetermined threshold to be considered a change in contact from changed to unchanged, or at least not sufficiently changed, tissue (or vice versa). This allows for some change in ECI without necessarily indicating a change in the tissue.

With continued reference to FIG. 16a, in a fourth step 152, an indication is provided to the clinician/physician, or to a robotic controller in a robotics-based system, as to whether the portion of the tissue that is presently in contact with the electrode 12 has sufficiently changed (e.g., is ablated) or is unchanged or insufficiently changed (e.g., is unablated or not fully ablated). Accordingly, depending on the result of the evaluation of the ECI values, the ECU 32 is configured to generate signal representative of an indicator of the type of tissue the electrode 12 is in contact with (e.g., changed (e.g., ablated) or unchanged/insufficiently changed (e.g., unablated or not fully ablated). The description set forth in great detail above relating to the generation and/or provision of indicators applies here with equal weight, and therefore, will not be repeated. This process repeats itself as the electrode 12 continues to move. Accordingly, each ECI calculation is saved in the memory 92/116 so that it may be compared to one or more subsequent ECI calculations.

Figure 16B:
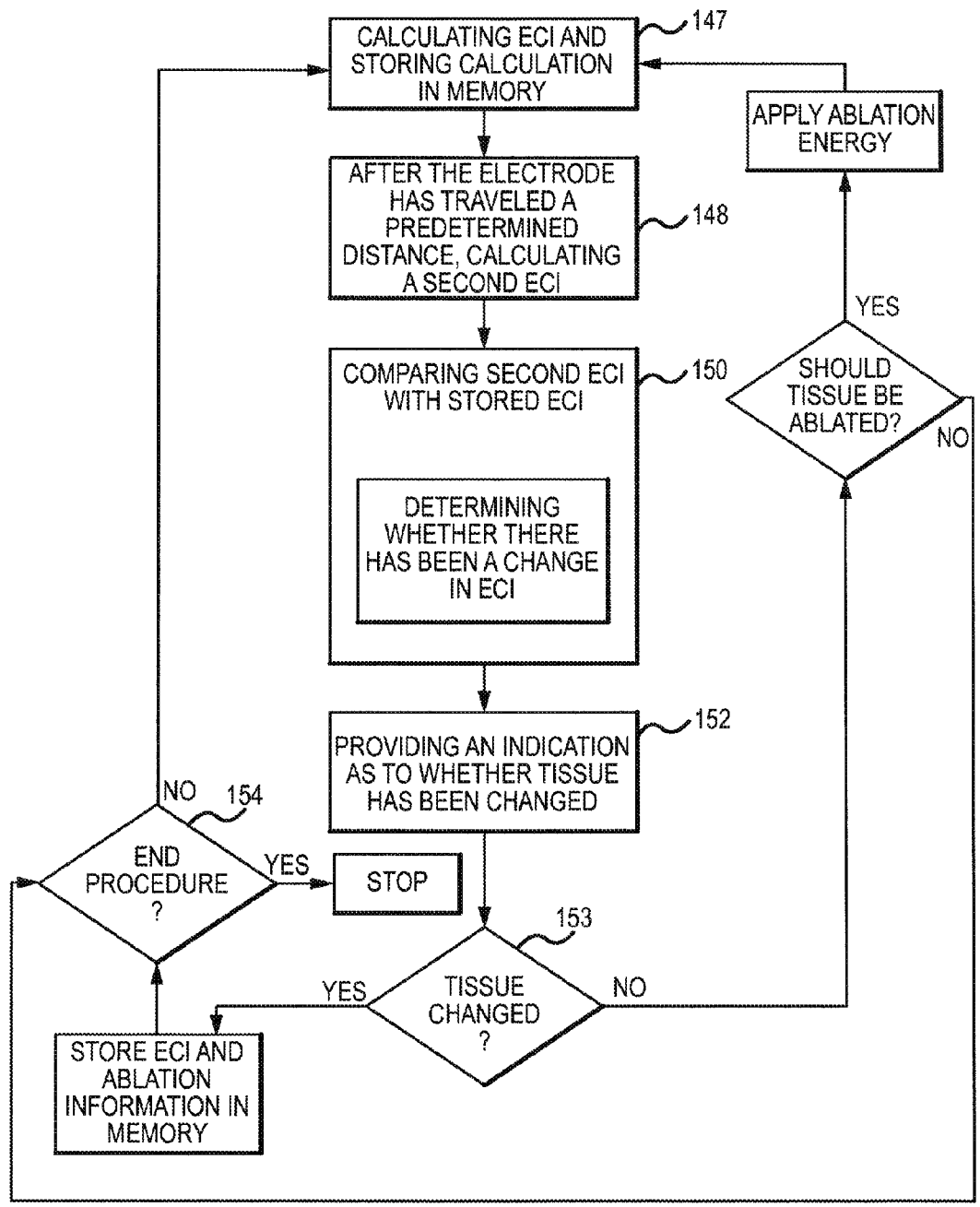

FIG. 16b depicts another exemplary embodiment of the method illustrated in FIG. 16a in which steps relating to an ablation procedure are included. For example, in a fifth step 153, a determination is made as to whether the tissue at the particular location that is being evaluated (i.e., the tissue that electrode 12 is in contact with) has been changed (e.g., ablated). If it has, the calculated ECI and ablation information may be stored in a storage medium, such as, for example, memory 92/116. In a sixth step 154, system 10 then determines whether the ablation procedure can be ended. If "yes," then the ablation procedure is stopped. If "no," then the process begins again at step 147.

If the tissue has not been changed, or at least not sufficiently changed (e.g., the tissue is unablated or not fully ablated), then the physician/clinician can determine whether it should be ablated. Alternatively, in a robotic application, a robotic controller can make such a determination. If the tissue should be ablated, ablative energy can be applied to the tissue at that particular location. Accordingly, the physician/clinician may move the catheter 14 to the particular location requiring ablation and then cause the ablative energy to be applied. Alternatively, in a robotic application, the robotic controller may cause the catheter 14 to move to the particular location requiring ablation and then cause the ablative energy to be applied. In such an embodiment, the system 30 may be used by the robotic controller to determine where the catheter 14 is and where it needs to go, as well as to assist in the direction of the movement of the catheter 14 to the desired location. The process may then proceed starting at step 147. If the tissue should not be ablated, then the ECI and ablation information may be stored in a storage medium, such as, for example, memory 92/116. The system 10 then determines whether the ablation procedure can be ended. If "yes," then the ablation procedure is stopped. If "no," then the process begins again at step 147.

In another exemplary embodiment, two or more ECI calculations for tissue at a particular location at two different points in time can be evaluated to determine whether the tissue at that particular location has been changed (e.g., ablated). More specifically, and with reference to FIG. 17a, in a first step 155, an ECI calculation is made for tissue at a particular location. In a second step 156, the ECI calculation and the corresponding location—which may be acquired from the mapping, visualization and navigation system 30—are saved in a storage medium, such as, for example and without limitation, the memory 92/116.

As the electrode 12 moves, a number of ECI calculations can be made. Once the procedure has been completed, in a third step 158, the electrode 12 can be brought back over the area that was to be ablated to determine if tissue at a particular location was, in fact, changed (e.g., ablated). In a fourth step 160, as the electrode visits each location for which a prior ECI calculation was made, another ECI calculation is made. In a fifth step 162, the ECU 32 accesses the prior ECI calculation that corresponds to the particular location, and compares the ECI calculations corresponding to the particular location to determine whether the ECI has changed. As described in greater detail above, whether the ECI value, or the change therein, meets, exceeds, or falls below a predetermined threshold, the ECU 32 is able to determine whether the tissue at that particular location has been changed (e.g., ablated). This process then continues as the electrode 12 continues to move along or about a perceived lesion line or area, or as long as the clinician/physician desires.

In an exemplary embodiment, in a sixth step 164, the ECU 32 may be configured to provide an indication of the respective ECI values, which a user may take into consideration and make a determination as to whether the tissue is changed (e.g., ablated) or unchanged, or at least not sufficiently changed (e.g., unablated or not fully ablated), and/or whether the tissue that the electrode is or was in contact with is changed or unchanged, or at least not sufficiently changed (e.g., unablated or not fully ablated) tissue. In either instance, the description set forth in great detail above relating to the generation and/or provision of indicators applies here with equal weight, and therefore, will not be repeated. Additionally, the description set forth above relating to the tolerances and/or the substantiality of the change in ECI applies here with equal force.

Figure 17A:
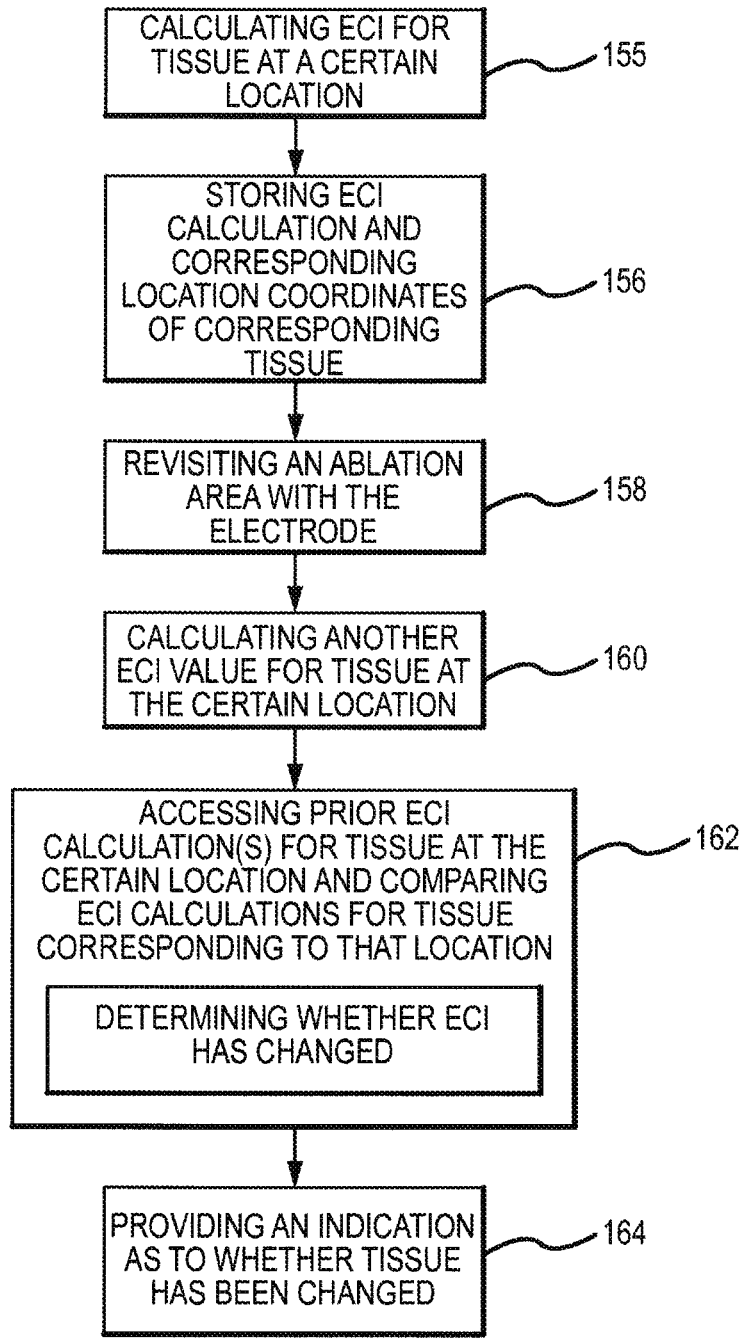
Figure 17B:
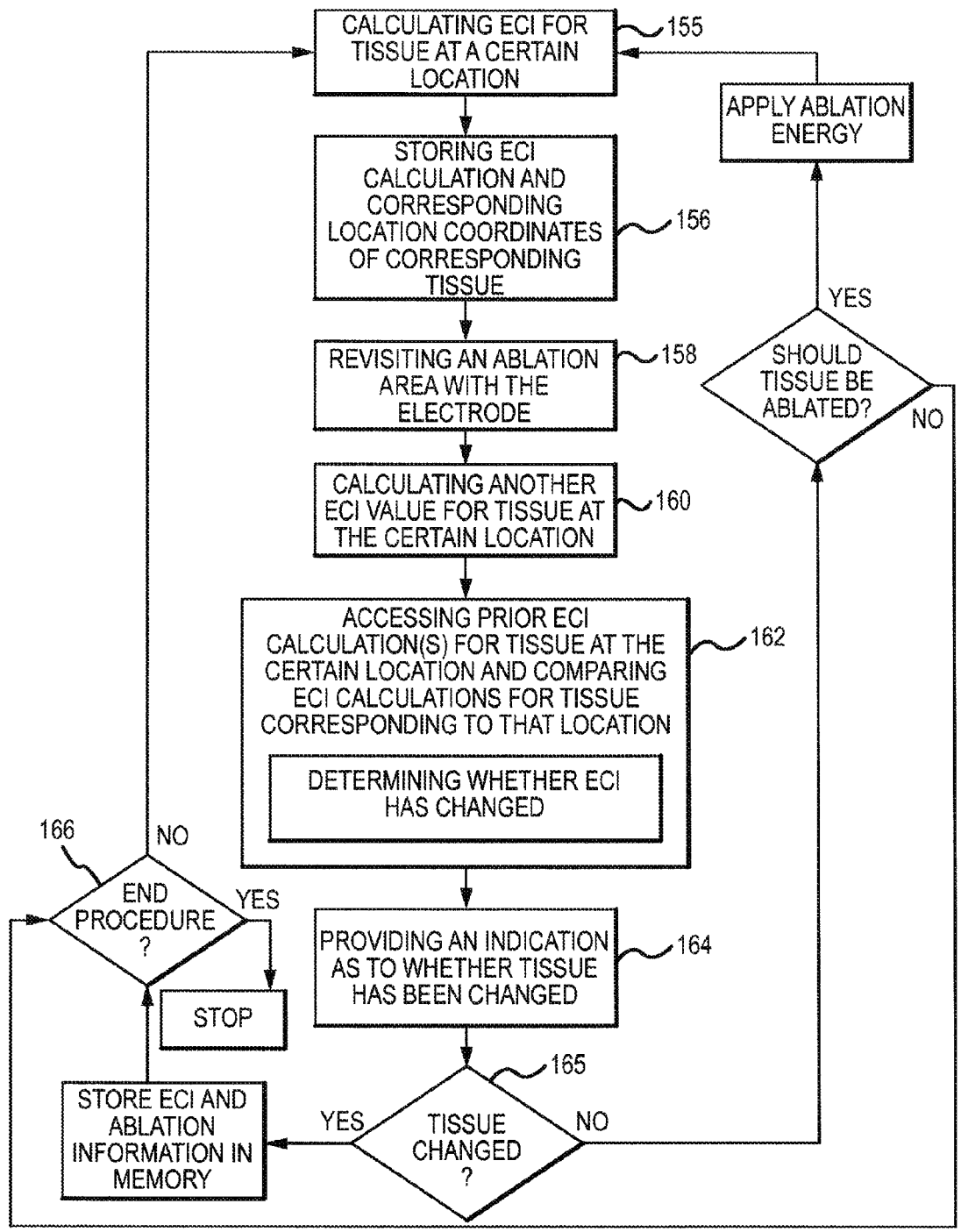

FIG. 17b depicts another exemplary embodiment of the method illustrated in FIG. 17a in which steps relating to an ablation procedure are included. For example, in a seventh step 165, a determination is made as to whether the tissue at the particular location that is being evaluated (i.e., the tissue that electrode 12 is in contact with) has been changed (e.g., ablated). If it has, the calculated ECI and ablation information may be stored in a storage medium, such as, for example, memory 92/116. In an eighth step 166, the system 10 then determines whether the ablation procedure can be ended. If "yes," then the ablation procedure is stopped. If "no," then the process begins again at step 155.

If the tissue has not been changed, or at least not sufficiently changed (e.g., the tissue is unablated or not fully ablated), then the physician/clinician can determine whether it should be ablated. Alternatively, in a robotic application, a robotic controller can make such a determination. If tissue should be ablated, ablation energy can be applied to the tissue at that particular location. Accordingly, the physician/clinician may move the catheter 14 to the particular location requiring ablation and then cause the ablative energy to be applied. Alternatively, in a robotic application, the robotic controller may cause the catheter 14 to move to the particular location requiring ablation and then cause the ablative energy to be applied. In such an embodiment, the system 30 may be used by the robotic controller to determine where the catheter 14 is and where it needs to go, as well as to assist in the direction of the movement of the catheter 14 to the desired location. The process may then proceed starting at step 155. If the tissue should not be ablated, then the ECI and ablation information may be stored in a storage medium, such as, for example, memory 92/116. The system 10 then determines whether the ablation procedure can be ended. If "yes," then the ablation procedure is stopped. If "no," then the process begins again at step 155.

In another exemplary embodiment, rather than evaluating the finite or raw ECI calculation or determining a change in two ECI calculations, the rate of change of the ECI or the slope of a line between at least two ECI calculations over a predetermined amount or time $$\left(\text{i.e., } \frac{d^2 ECI}{dt^2}\right)$$

is determined and used to assess lesion formation. More particularly, when the electrode 12 moves from tissue that has been changed (e.g., ablated) to tissue that has not been changed or at least not sufficiently changed (e.g., unablated or not fully ablated), the rate of change or the change in the slope over a predetermined amount of time is most evident. In other words, if the electrode 12 remains in contact with either changed (e.g., ablated) or unchanged/insufficiently changed (e.g., unablated or not fully ablated) tissue, respectively, the rate of change in the ECI may not be appreciable. However, when the electrode 12 moves from tissue that has been changed to tissue that has not been changed, or at least not sufficiently changed, or vice versa, the rate of change in the ECI may be appreciable. Thus, if the rate of change over a predetermined period of time meets, exceeds, or falls below (depending on the circumstances) a predetermined threshold value, then one is able to determine what type of tissue with which the electrode 12 is currently in contact. Accordingly, the rate of change in ECI or the change in the slope over a predetermined period of time can be useful in assessing lesion formation.

Figure 18A:
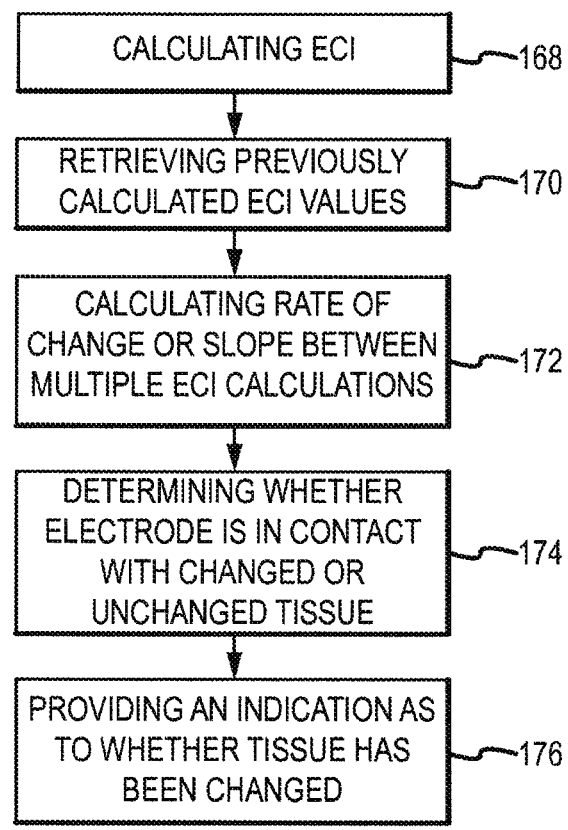

FIG. 18a illustrates one exemplary embodiment of a methodology that uses the rate of change of the ECI. In this embodiment, the memory 92/116 stores a predetermined number of previously calculated ECI calculations. As described above, the memory 92/116 may be part of the ECU 32 or may be a separate and distinct component that is accessible by the ECU 32 such that the ECU 32 may retrieve the stored ECIs. In an exemplary embodiment, the ECU 32 is configured to access the memory 92/116 and to calculate the rate of change in the ECI or the slope of a line drawn between a current or most recent ECI calculation and one or more previously calculated ECIs. Depending on if the rate of change meets, exceeds, or falls below a predetermined threshold that is programmed into ECU 32, the ECU 32 may be configured to recognize that the electrode 12 is in contact with changed (e.g., ablated) or unchanged/insufficiently changed (e.g., unablated or not fully ablated) tissue, or may simply provide the rate of change to a user for the user to determine the type of tissue with which the electrode is in contact.

Accordingly, with continued reference to FIG. 18a, in a first step 168, a current ECI is calculated and may be stored in the memory 92/116. In a second step 170, the ECU 32 accesses the memory 92/116 to retrieve one or more previously calculated ECIs. In a third step 172, the rate of change or slope between the current ECI and the one or more previously calculated ECIs stored in the memory 92/116 is calculated. In a fourth step 174, the ECU 32 determines whether the electrode 12 is in contact with tissue that has been changed (e.g., ablated) or tissue that has not been changed, or at least not sufficiently changed (e.g., unablated or not fully ablated) based on the calculated rate of change. In an exemplary embodiment, in a fifth step 176, an indication may be provided to the clinician/physician as to what type of tissue with which the electrode 12 is currently in contact. Accordingly, the ECU 32 may be further configured to generate a signal representative of an indicator corresponding to the type of tissue with which the electrode 12 is in contact. The description set forth above in great detail relating to the generation and/or provision of indicators applies herewith equal weight, and therefore, will not be repeated.

Figure 18B:
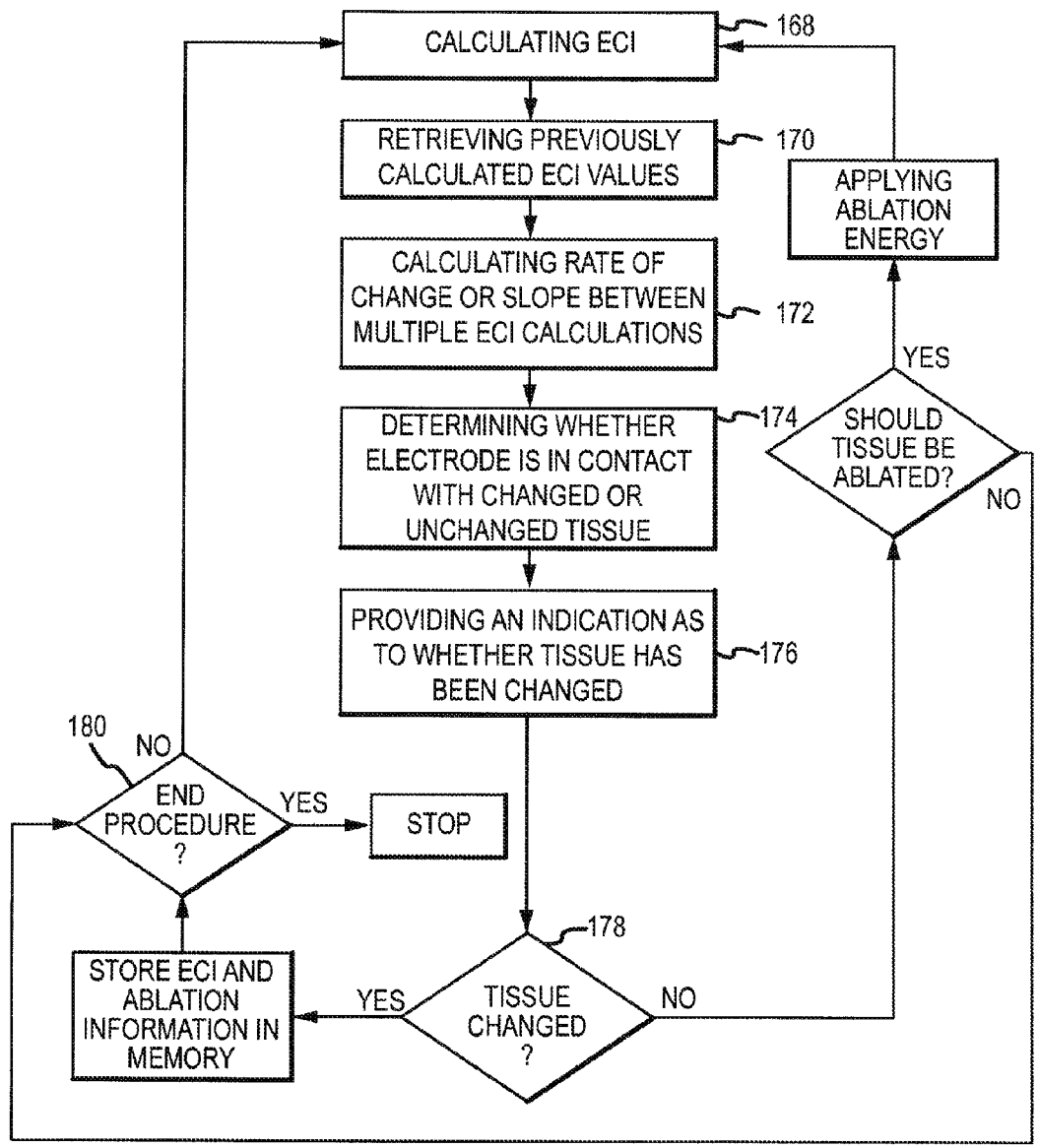

FIG. 18b depicts another exemplary embodiment of the method illustrated in FIG. 18a in which steps relating to an ablation procedure are included. For example, in a sixth step 178, a determination is made as to whether the tissue at the particular location that is being evaluated (i.e., the tissue that electrode 12 is in contact with) has been changed (e.g., ablated). If it has, the calculated ECI and ablation information may be stored in a storage medium, such as, for example, memory 92/116. In a seventh step 180, the system 10 then determines whether the ablation procedure can be ended. If "yes," then the ablation procedure is stopped. If "no," then the process begins again at step 168.

If the tissue has not been changed, or at least not sufficiently changed (e.g., the tissue is unablated or not fully ablated), then the physician/clinician can determine whether it should be ablated or reablated. Alternatively, in a robotic application, a robotic controller can make such a determination. If tissue should be ablated, ablative energy can be applied to the tissue at that particular location. Accordingly, the physician/clinician may move the catheter 14 to the particular location requiring ablation and then cause the ablative energy to be applied. Alternatively, in a robotic application, the robotic controller may cause the catheter 14 to move to the particular location requiring ablation and to then cause the ablative energy to be applied. In such an embodiment, the system 30 may be used by the robotic controller to determine where the catheter 14 is and where it needs to go, as well as to assist in the direction of the movement of the catheter 14 to the desired location. The process may then proceed starting at step 168. If the tissue should not be ablated, then the ECI and ablation information may be stored in a storage medium, such as, for example, memory 92/116. The system 10 then determines whether the ablation procedure can be ended. If "yes," then the ablation procedure is stopped. If "no," then the process begins again at step 168.

In another exemplary embodiment, rather than evaluating static or raw ECI calculations, or the rate of change in such calculations, ECI may be used, in part, to calculate an ECI rate (ECIR). The ECIR can be used in lesion assessment. In an exemplary embodiment, the ECU 32 is configured to calculate the ECIR, however, the present invention is not meant to be so limited. Rather, other processors or components may be employed to perform the calculation.

In simple terms, the ECIR is calculated by dividing the change in ECI over a predetermined amount of time by the change in the distance or position of the electrode 12 over the same predetermined amount of time. More specifically, the ECIR is calculated using equation (4) above. As described above, the change in the ECI is calculated by sampling the ECI calculations performed by the ECU 32 at a predetermined rate and then determining the difference between a current calculation and the most recent previous calculation, for example, that may be stored in the memory 92/116. In another exemplary embodiment, the difference may be between a current calculation and multiple previous calculations, or an average of previous calculations.

In an exemplary embodiment, the ECU 32 samples the calculated ECI at a predetermined sampling rate, and then calculates the change in the ECI over that time interval. It will be appreciated by those of ordinary skill in the art that the ECI may be sampled at any number of time intervals or rates. For example, in one embodiment using known techniques, the sampling is timed or synchronized to coincide with the cardiac cycle of the patient's heart so as to always sample at the same point in the cardiac cycle. In another embodiment, the sampling of the ECI is dependent upon a triggering event rather than a defined time interval. For instance, the sampling of the ECI may be dependent upon the change in the distance/position of the electrode 12 meeting a predetermined threshold. More specifically, when it is determined that the electrode 12 has moved a predetermined distance, the ECU 32 will sample the ECI over the time interval it took the electrode 12 to move the predetermined distance. Accordingly, it will be appreciated by those of ordinary skill in the art that many different sampling rates and/or techniques may be used to determine the change in ECI.

With respect to the change in distance/location of the electrode, as described above this change may be calculated by the ECU 32 based on location coordinates provided to it by the system 30, or may be calculated by the system 30 and then provided to the ECU 32. As with the change in ECI, the change in distance or location is determined by sampling the location coordinates of the electrode 12 at a predetermined sampling rate. From this, the change in distance over time can be derived. As with the sampling of the ECI calculations, the location coordinates of the electrode 12 are sampled at a predetermined sampling rate and then the change in the location is calculated over that time interval. It will be appreciated by those of ordinary skill in the art that the location/position may be sampled at various rates and using various techniques (e.g., synchronization with cardiac cycle). Accordingly, the present invention is not limited one particular sampling rate/technique.

Once the two "change" calculations have been made, the ECU 32 is able to calculate the ECIR by dividing the change in the ECI by the change in the distance or location of the electrode 12. In an exemplary embodiment, the calculated ECIR is stored in a storage medium, such as, for example, memory 92/116, that is accessible by the ECU 32.

Once the ECIR has been calculated, it may be used to assess, among other things, whether the electrode 12 is in contact with tissue that has been changed (e.g., ablated) or tissue that has not changed, or at least has not sufficiently changed (e.g., unablated or not fully ablated). In an exemplary embodiment illustrated in FIG. 19a, the ECIR is calculated in a first step 182 by dividing the change in ECI by the change in distance. In a second step 184, the calculated ECIR is evaluated to determine whether the calculated ECIR meets, exceeds, or falls below a predefined threshold value. Depending on where the calculated ECIR falls with respect to the threshold, a determination can be made as to what type of tissue with which the electrode 12 is in contact.

More particularly, in a first substep 186 of step 184, an ECIR threshold is defined. This threshold may be set by either preprogramming it into the ECU 32, or a user may manually input it into the ECU 32 using a conventional I/O interface.

In a second substep 188 of second step 184, the calculated ECIR is compared to the predefined threshold. Based on this comparison, the determination is made as to what type of tissue the electrode 12 is contacting (e.g., changed (e.g., ablated) or unchanged/insufficiently changed (e.g., unablated or not fully ablated), for example) or from what type of tissue the electrode has traveled. In an exemplary embodiment, in a third step 190, the ECU 32 may be configured to provide an indication as to the value of the ECIR, which a user may take into consideration and make a determination as to whether the tissue has been changed (e.g., ablated) or unchanged/insufficiently changed (e.g., unablated or not fully ablated), and/or whether the tissue that the electrode is or was in contact with has been changed or unchanged/insufficiently changed (e.g., ablated or unablated/not fully ablated tissue). The description set forth in great detail above relating to the generation and/or provision of indicators applies here with equal force, and therefore, will not be repeated.

Figure 19A:
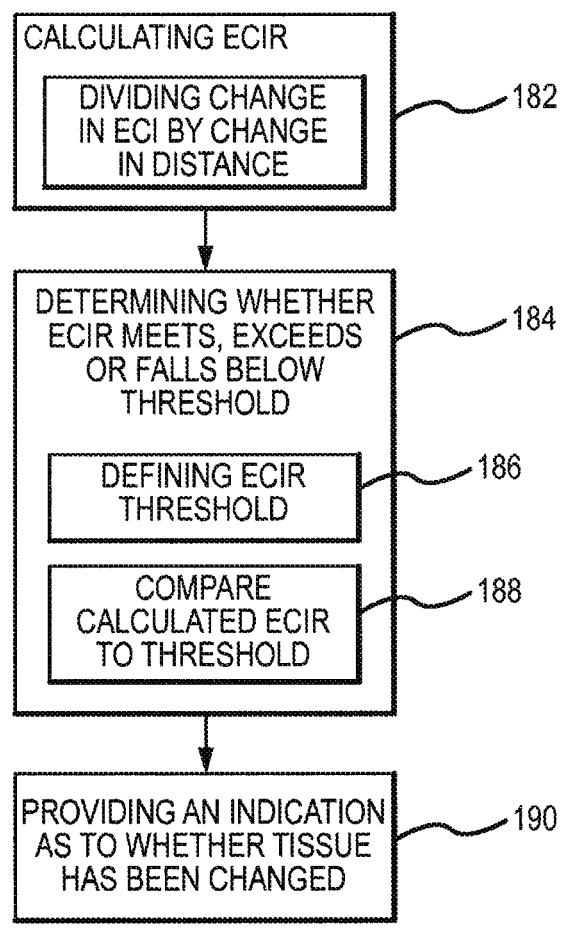
Figure 19B:
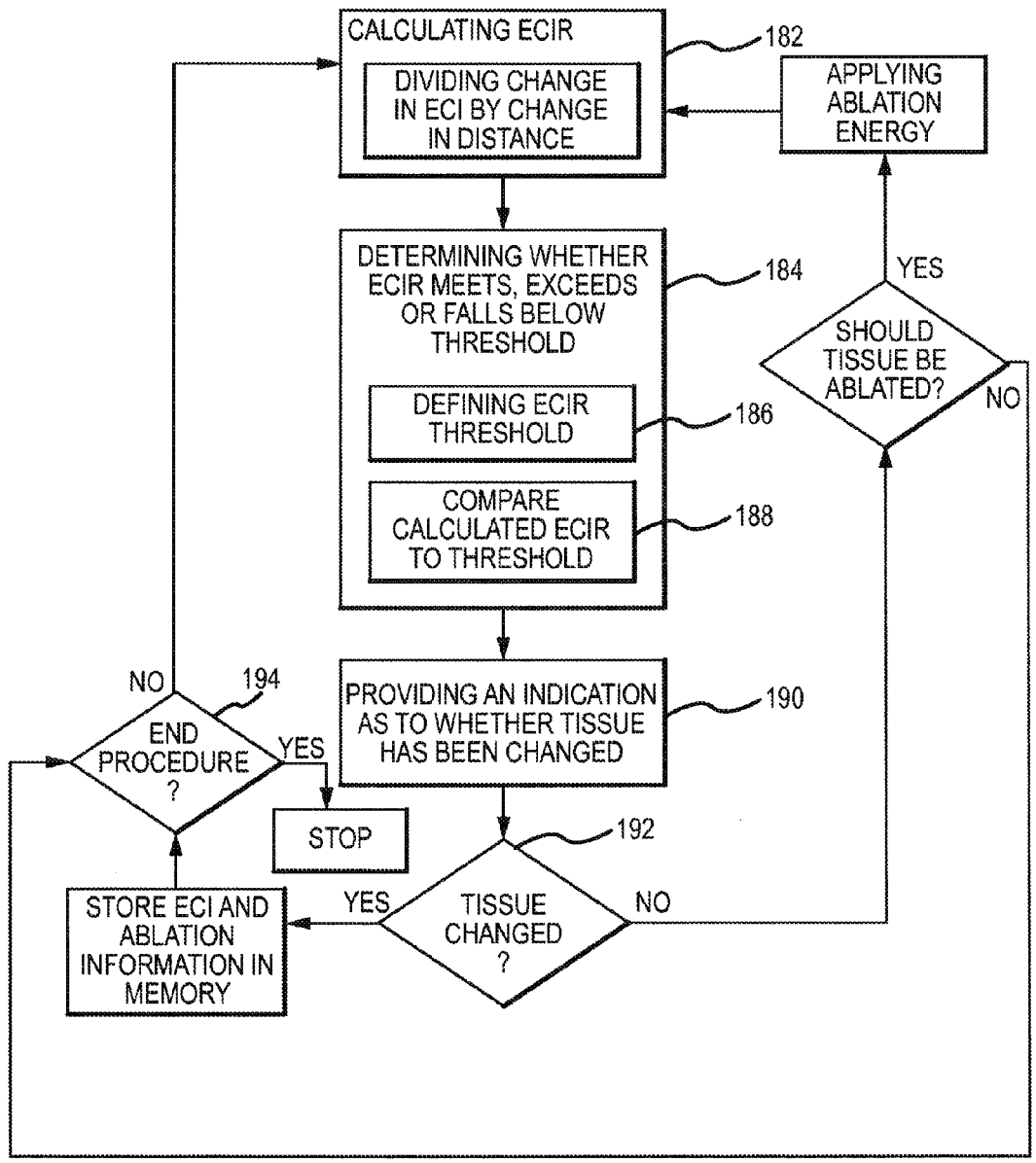

FIG. 19b depicts another exemplary embodiment of the method illustrated in FIG. 19a in which steps relating to an ablation procedure are included. For example, in a fourth step 192, a determination is made as to whether the tissue at the particular location that is being evaluated (i.e., the tissue that electrode 12 is in contact with) has been changed (e.g., ablated). If it has, the calculated ECI and ablation information may be stored in a storage medium, such as, for example, memory 92/116. In a fifth step 194, the system 10 then determines whether the ablation procedure can be ended. If "yes," then the ablation procedure is stopped. If "no," then the process begins again at step 182.

If the tissue has not been changed, or at least not sufficiently changed (e.g., the tissue is unablated or not fully ablated), then the physician/clinician can determine whether it should be ablated. Alternatively, in a robotic application, a robotic controller can make such a determination. If tissue should be ablated, ablative energy can be applied to the tissue at that particular location. Accordingly, the physician/clinician may move the catheter 14 to the particular location requiring ablation and then cause the ablative energy to be applied. Alternatively, in a robotic application, the robotic controller may cause the catheter 14 to move to the particular location requiring ablation and to then cause the ablative energy to be applied. In such an embodiment, the system 30 may be used by the robotic controller to determine where the catheter 14 is and where it needs to go, as well as to assist in the direction of the movement of the catheter 14 to the desired location. The process may then proceed starting at step 182. If the tissue should not be ablated, then the ECI and ablation information may be stored in a storage medium, such as, for example, memory 92/116. The system 10 then determines whether the ablation procedure can be ended. If "yes," then the ablation procedure is stopped. If "no," then the process begins again at step 182.

In any of the embodiments above, there are several variables that may have an impact on the calculation of the ECI. For example, the amount of contact force or contact pressure applied to the electrode against the tissue, the particular type of tissue being evaluated (i.e., different types of cardiac tissue, for example), the temperature of the tissue or change in temperature of the tissue, the degree of heating of the tissue, the depth of tissue heated, the volume of tissue heated, the saline flow rate through the catheter, the blood flow rate across the catheter, and the like may individually or collectively cause an impact in the ECI calculation. Therefore, in certain embodiments, these variables can be taken into account in the calculation.

Accordingly, in an exemplary embodiment, offsets may be used to either increase or decrease the calculated ECI to a Corrected ECI ("CECI") to account for one or more variables. These offsets perform a scaling function to ensure that it is the actual ECI of the tissue that is being assessed or evaluated rather than an ECI influenced by one or more variables. These offsets may be stored, for example, in the memory 92/116 such that the ECU 32 can access them when appropriate. These offsets may be arranged in the form of a look-up table or in another equivalent structure or manner and correlated with particular force magnitudes, temperatures, tissue type, etc. Accordingly, when making a CECI calculation, the ECU 32 is configured to receive one or more inputs corresponding to one or more variables, and to then evaluate or process the CECI calculation accordingly.

For example, the ECU 32 may be configured to receive a force measurement from a force gauge that may be mounted proximate the electrode 12 or otherwise associated therewith, representing the amount of contact force being applied to the tissue. The ECU 32 may be configured to access a look up table stored in the memory 92/116, in ECU 32 (or elsewhere in the system 10) that correlates one or more force measurements with corresponding CECI offsets. Likewise, the ECU 32 may be configured to calculate a corresponding CECI offset from a predetermined relationship between the degree of force and the desired CECI offset. Thus, when the ECU 32 makes a CECI calculation, it can look up the force measurement in the table, acquire the appropriate offset, and then add or subtract the offset from the CECI calculation. This permits ECI calculations, among other things, to be compared with each other regardless of the amount of force being applied by the electrode 12 against the tissue at any particular time.

Likewise, the ECU 32 may be configured to receive a pressure measurement from a pressure or force gauge that may be mounted proximate to the electrode 12 or otherwise associated therewith, representing the amount of contact pressure being applied to the tissue. The ECU 32 may be configured to access a lookup table stored in the memory 92/116, in ECU 32 (or elsewhere in the system 10) that correlates one or more pressure or force measurements with corresponding CECI offsets. Likewise, the ECU 32 may be configured to calculate a corresponding CECI offset from a predetermined relationship between the pressure and the desired CECI offset. If the measurement is a force measurement, it can be corrected based on the characteristics of the catheter used into a pressure measurement. Thus, when the ECU 32 makes a CECI calculation, it can look up the pressure measurement in the table, acquire the appropriate offset, and then add or subtract the offset from the ECI calculation. This permits CECI calculations, among other things, to be compared with each other regardless of the amount of pressure being applied by the electrode 12 against the tissue at any particular time.

This same process may be used for temperature measurements, and other variables, such as, for example, saline flow rate through the catheter, blood flow rate across the catheter, and other parameters that could affect ECI though coupling to the tissue has not changed. For example, the system may either directly measure a temperature of the tissue or it may receive a temperature input from an outside source. The temperature input can be electrode temperature, a tissue temperature, or another type of measurement. As with force or pressure, this temperature input is sent to the ECU 32, which is configured to access a lookup table stored in the memory 92/116, in ECU 32 (or elsewhere in the system 10) that correlates one or more temperature or heating measurements with corresponding CECI offsets. Likewise, the ECU 32 may be configured to calculate a corresponding CECI offset from a predetermined relationship between the temperature and the desired CECI offset. This process may also be used for evaluating different types of tissue. In such an embodiment, the ECU 32 is configured to receive an input to allow the ECU 32 to recognize the type of tissue being evaluated. In an exemplary embodiment, the user is permitted to indicate the tissue type by way of a conventional I/O interface. Accordingly, different variables may be taken into account in the ECI calculations.

One challenge in assessing lesions and/or determining whether tissue has been ablated lies in the fact that the ECI will change if contact between the electrode 12 and the tissue changes. Accordingly, a change in the ECI alone may not always be sufficiently indicative of tissue having been changed (e.g., ablated). For example, the ECI changes if there is a loss of contact between the electrode 12 and the tissue. Similarly, ECI changes as electrode 12 moves from contact with unchanged or insufficiently changed (e.g., unablated or not fully ablated) to changed (e.g., ablated) tissue. As such, the change in ECI resulting from loss of contact may pose a challenge to providing an indication that the tissue at that particular location has been changed (e.g., ablated). One way to address or overcome such a challenge is by measuring either contact force or contact pressure (or both). Accordingly, in order to determine whether the change in the ECI is due to loss of contact or rather change in the tissue, the ECI and the force and/or the pressure are evaluated together. Thus, in another exemplary embodiment, rather than evaluating the ECI alone for lesion assessment, the calculated ECI and force measurements may be evaluated together to determine or assess whether tissue has been changed (e.g., ablated), and such an evaluation may be made in substantially real-time.

For example, prior to the electrode 12 contacting tissue, the force (and/or the pressure) and the ECI are both relatively low. Once contact is made, the force (and/or the pressure) and the ECI increase. When ablation commences, the force may not dramatically change, but the ECI may change. Accordingly, at the divergence between the force and the ECI, it can be determined that the tissue at that particular location has been or is being ablated, as opposed to a change in the ECI as result of loss of contact. Therefore, both the force and ECI can be evaluated and monitored by the ECU 32, and then a determination can be made based on the changes in each as to whether tissue at a particular location has been changed (e.g., ablated) or not.

Figure 20A:
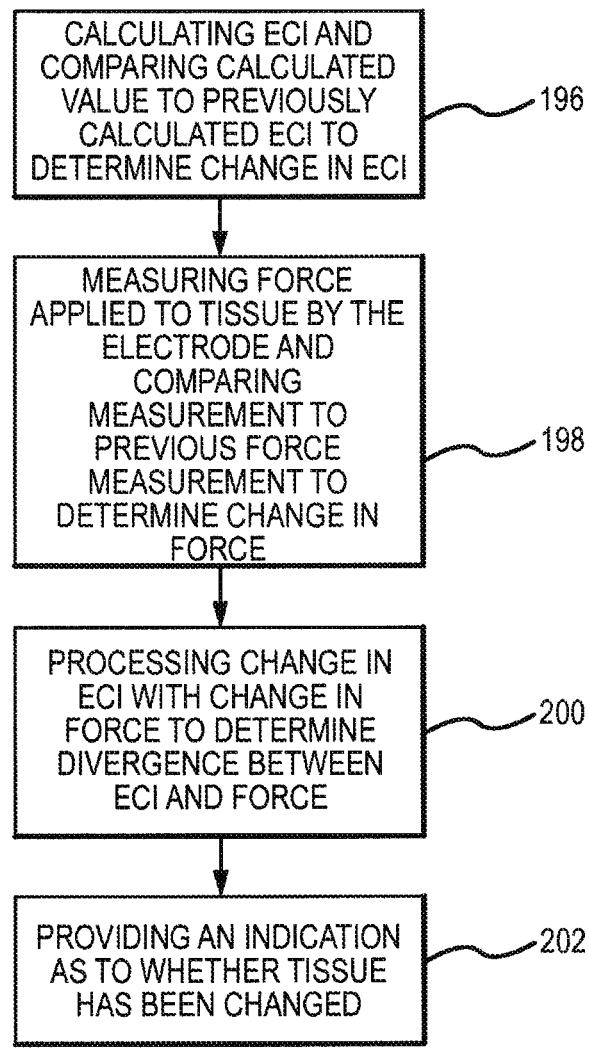

FIG. 20a illustrates an exemplary embodiment of this methodology. In a first step 196, an ECI calculation is made and compared to one or more stored previously calculated ECIs. In a second step 198, a force measurement is made and compared to one or more previously acquired force measurements or to a lookup table. The ECU 32 may be configured to receive and compare the force measurements, or alternatively, the change in force may be calculated elsewhere in the system 10 and provided to the ECU 32. In either instance, in a third step 200, the change in the ECI and the change in the force are processed with each other and then the ECU 32 determines whether the ECI and force have diverged. If so, the ECU 32 recognizes that there has been a change in the type of tissue (i.e., changed (e.g., ablated) or unchanged/insufficiently changed (e.g., unablated or not fully ablated)) with which the electrode 12 is in contact. As described above, in a fourth step 202, an indicator may be generated and/or displayed to communicate the type of tissue. The description set forth in great detail above relating to the generation and/or provision of indicators applies here with equal force, and therefore, will not be repeated.

Figure 20B:
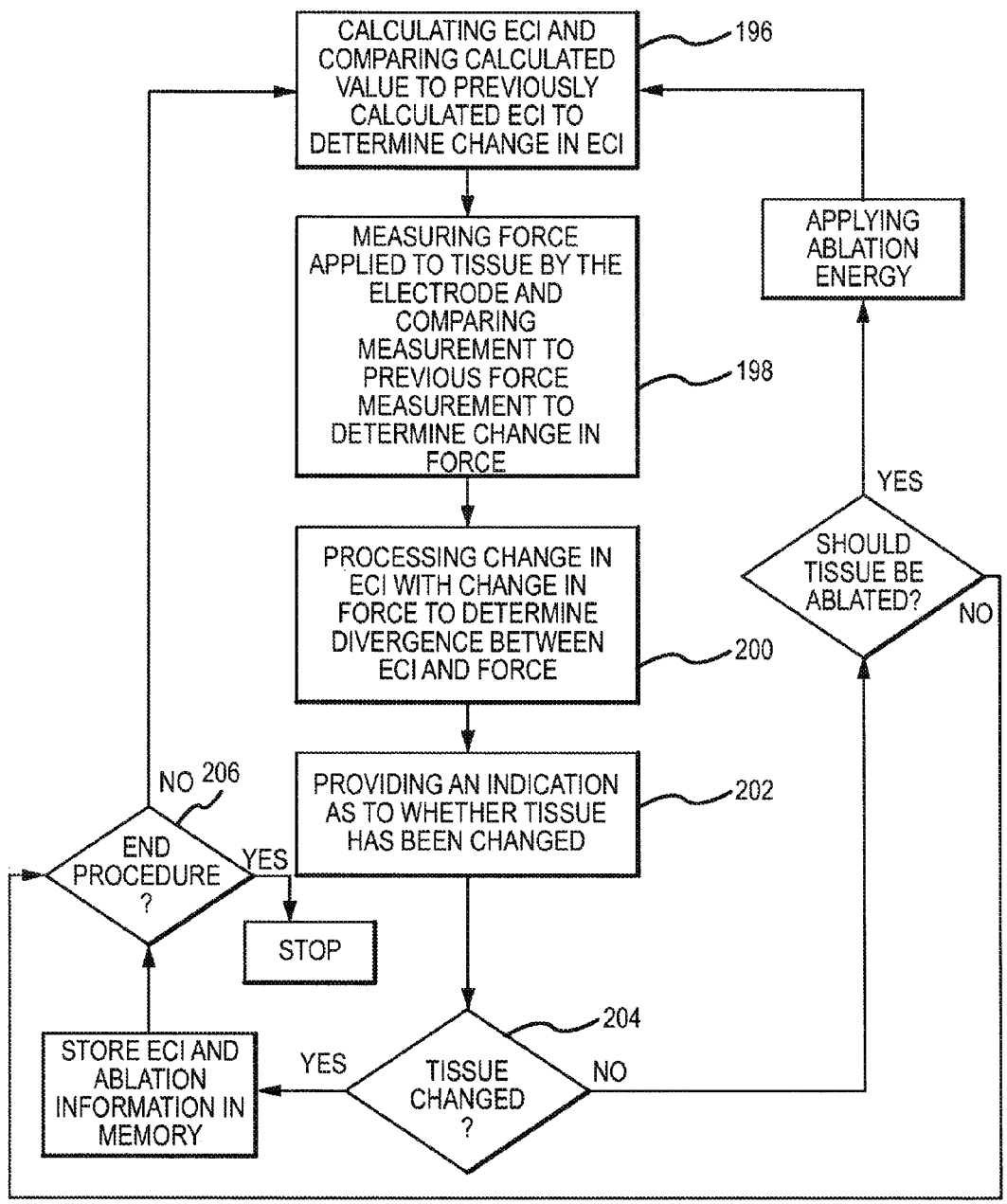

FIG. 20b depicts another exemplary embodiment of the method illustrated in FIG. 20a in which steps relating to an ablation procedure are included. For example, in a fifth step 204, a determination is made as to whether the tissue at the particular location that is being evaluated (i.e., the tissue that electrode 12 is in contact with) has been changed (e.g., ablated). If it has, the calculated ECI and ablation information may be stored in a storage medium, such as, for example, memory 92/116. In a sixth step 206, the system 10 then determines whether the ablation procedure can be ended. If "yes," then the ablation procedure is stopped. If "no," then the process begins again at step 196.

If the tissue has not been changed or at least not sufficiently changed (e.g., the tissue is unablated or not fully ablated), then the physician/clinician can determine whether it should be ablated. Alternatively, in a robotic application, a robotic controller can make such a determination. If tissue should be ablated, ablation energy can be applied to the tissue at that particular location. Accordingly, the physician/clinician may move the catheter 14 to the particular location requiring ablation and then cause the ablative energy to be applied. Alternatively, in a robotic application, the robotic controller may cause the catheter 14 to move to the particular location requiring ablation and to then cause the ablative energy to be applied. In such an embodiment, the system 30 may be used by the robotic controller to determine where the catheter 14 is and where it needs to go, as well as to assist in the direction of the movement of the catheter 14 to the desired location. The process may then proceed starting at step 196. If the tissue should not be ablated, then the ECI and ablation information may be stored in a storage medium, such as, for example, memory 92/116. The system 10 then determines whether the ablation procedure can be ended. If "yes," then the ablation procedure is stopped. If "no," then the process begins again at step 196.

It should be noted that the above described methodology may be employed taking into account variables other than or in addition to force, such as, for example, pressure. In such an instance, the same steps above would apply with equal force, with the exception that the measurements and comparisons would relate to pressure rather than force. Accordingly, the methodology will not be repeated here.

In accordance with another aspect of the invention, indices other than ECI, such as, for example, an ablation lesion index (ALI), may be calculated and evaluated to allow for the assessment of lesions. Such indices may take into account the complex impedance, or the components thereof (i.e., the resistance "R" and the reactance "X", for example), as well as variables such as temperature, pressure, contact force, saline flow rate through the catheter, blood flow rate across the catheter, and/or other parameters that could affect ALI though coupling to the tissue has not changed. As with ECI, in an exemplary embodiment, these indices may be displayed on a display in any number of ways or formats, or otherwise used to provide information in a useful format to a clinician/physician or robotic controller to allow for, or aid in, the assessment of lesion formation.

In an exemplary embodiment, an ALI derived from ECI is defined and calculated. In such an embodiment, the ALI calculation takes into account ECI as well as various confounding variables such as, for example, contact force and tissue temperature. In other exemplary embodiments, additional confounding variables such as, for example, trabeculation, may be taken into account. As will be described in greater detail below, the ALI can be specifically used for determining ablation lesion changes induced in tissue such that one can determine whether tissue has been changed (e.g., ablated), and if so, assess the quality or extent of the formed lesion, as well as to determine lesion volume growth. Since temperature is taken into consideration, such an index would find particular applicability in real-time assessment of lesions as they are created during an ablation procedure. In an embodiment in which the ALI is calculated taking into account temperature and force, the catheter 14 would include temperature and force sensors mounted thereon to obtain measurements for the temperature and force variables. As will be seen below, trabeculation cannot be directly measured, and so this variable can be determined by evaluating other confounding variables.

Accordingly, in an exemplary embodiment in which the ALI is used in the assessment of lesion formation, the ECU 32 may be configured to receive one or more inputs comprising the components of the complex impedance, contact force, temperature, and potentially other variables, such as, for example, pressure. The ECU 32 can then process these inputs and generate an index to allow for the assessment of lesion formation as the lesion is being formed or after formation. Additionally, additional frequencies may be employed to better discriminate lesion changes in tissue from temperature and contact force. Further, the generated index may be calculated based on discrete values for each input, on the respective changes in the input values, or a combination of both. As will be described in greater detail below, once calculated, the index may be evaluated in a similar manner as that described above with respect to ECI calculations to assess lesion formation. Accordingly, in such an embodiment, variables such as, for example and without limitation, contact force and temperature are taken into account in the index calculation itself as opposed to correcting or scaling a previously calculated index as a result of the impact variables may have on the index calculation.

In an exemplary embodiment, the ALI may be calculated using equation (7), which represents the equation in its most general form without accounting for trabeculation:

$$\text{ALI}=a_1 ECI+a_2 T+a_3 F \quad (7)$$

In this equation the terms ECI, T, and F represent calculated or measured values of each of the ECI, temperature (T), and contact force (F) at a particular position or location of the tissue at a particular time. The ECI is calculated as described in great detail above, while the temperature and contact force are measured using sensors mounted to or otherwise associated with the catheter 14. The coefficients $a_1$, $a_2$, and $a_3$ are predetermined values that are intended to account for the dependent relationship between each of the respective variables and the other measurements/calculations. These coefficients can be determined in a number of ways such as, for example, controlled experimentation or linear regression analysis. In the first instance, one of the temperature and force variables is fixed and the other is adjusted. The effect the adjustment has on the ECI is evaluated and a constant of proportionality (i.e., coefficient) is determined. This process is then repeated for each variable until all of the coefficients have been determined. In the second instance, all of the experimental data is input into a linear regression analysis and the "best fit" approach is used to figure out each coefficient. In either instance, once the coefficients are determined, they are stored or programmed into the ECU 32 or a memory/storage device associated therewith. It should be noted that the coefficients are determined and programmed as part of the manufacturing or setup process of the system 10, and thus, are not determined during use of the system 10.

In another exemplary embodiment, ALI may be calculated using equation (8), which takes into account the confounding variable of trabeculation:

$$\text{ALI}(t)=a_0+a_1 ECI(t)+a_2 T(t)+a_3 F(t)+a_4 \text{trab}(t)=a_0'+a_1 ECI(t)+a_2 T(t)+a_3 F(t) \quad (8)$$

As briefly described above, the nature of trabeculation is such that it does not lend itself to direct measurement. However, the effect of trabeculation can be accounted for using other variables, namely, force and temperature. This is represented by the $a_0'$ term in equation (8). In an exemplary embodiment, $a_0'$ is calculated using equation (9):

$$a_0'=a_0+a_4 \text{trab}=-(a_1 ECI_0+a_2 T_0+a_3 F_0) \quad (9)$$

In equation (9), $a_0'$ is calculated at time t=0, which is preablation. As such, each term is measured/calculated prior to the performance of an ablation procedure. The coefficients are determined as described above. The term $a_0'$ serves the function of an offset constant for subsequent ALI calculations assuming the degree of trabeculation remains constant.

As can be seen in equation (8), the ALI is calculated as a function of time. Accordingly, while the offset constant $a_0'$ is calculated at time t=0, the remaining terms in equation (8) are determined at time t=n, where n is a time either during or post-ablation that is later in time than t=0. Therefore, in practice, $a_0'$ is calculated prior to an ablation procedure. In an exemplary embodiment, the ALI is monitored in substantially real-time as the ablation procedure progresses. Accordingly, $a_0'$ is processed with the values of the other terms of equation (8) that are calculated at t=1, for example. As the procedure continues, $a_0'$ may be processed with the other terms that are calculated at t=2, and so on. In another exemplary embodiment, the ALI is monitored after the completion of the ablation procedure (i.e., not necessarily in real-time). Accordingly, if the ablation procedure ends at t=3, for example, $a_0'$ is processed with the other terms that are calculated at t=3. Thus, ALI may be monitored from just after the commencement of an ablation procedure until after the ablation procedure ends in order to evaluate and assess the formation of the lesion. Alternatively, rather than keeping $a_0'$ constant throughout the ablation procedure, in another exemplary embodiment, $a_0'$ may be reevaluated before each individual lesion is formed during the ablation procedure. By reevaluating $a_0'$ in this manner, each lesion site's trabeculation may be compensated for prior to the formation of the respective lesion.

Figure 21:
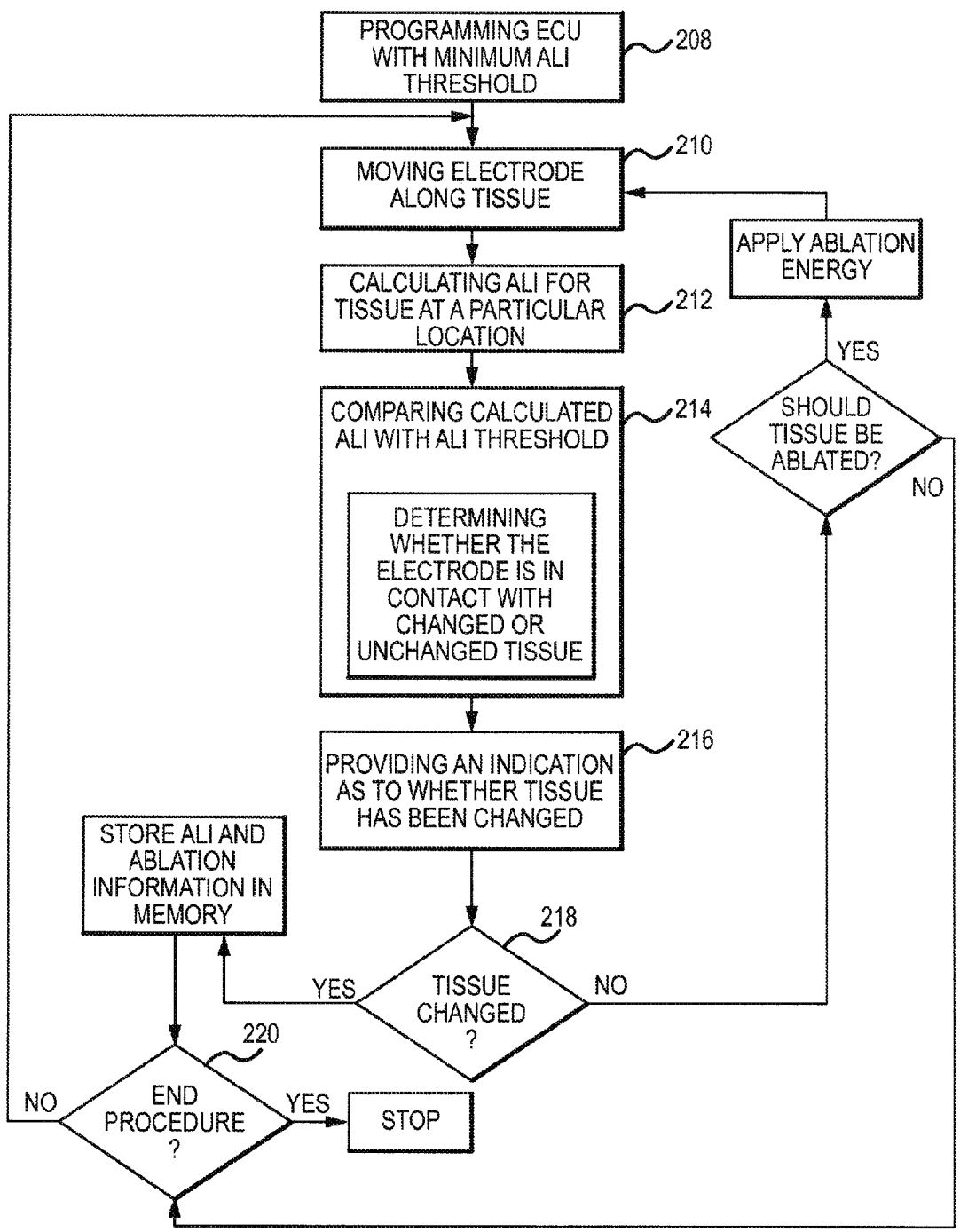
FIGS. 21-27 are flow diagrams illustrative of various exemplary embodiments of ALI-based methods for lesion assessment in tissue in accordance with the present teachings.

Whether the ALI is calculated using equations (7) or (8), or any other equation, the calculated ALI may be used in a number of ways to assess (i) whether the tissue has been changed (e.g., ablated), and/or (ii) the quality or extent of the lesion resulting from the ablation. In one exemplary embodiment illustrated in FIG. 21, a first step 208 comprises programming the ECU 32 with a predetermined minimum ALI threshold that represents the minimum ALI level for which contact between the electrode 12 and unchanged/insufficiently changed (e.g., unablated or not fully ablated) tissue is attained. In an exemplary embodiment, this threshold value is zero, as anything above zero is indicative of at least some degree or extent of ablation. The ECU 32 may be preprogrammed with the threshold or a user may input the threshold via a conventional I/O interface, thereby allowing the threshold to be changed. To evaluate the formation of a lesion line or ablated area, in a second step 210, while maintaining contact with the tissue, the electrode 12 is moved along or about the area of tissue that was subjected to an ablation procedure. In a third step 212, as the electrode 12 is moved, one or more ALI calculations are made at various points in time. For each calculated ALI, a fourth step 214 is performed that comprises comparing the calculated ALI with the predetermined threshold. If the calculated ALI exceeds the threshold, a determination can be made that the tissue at that particular location was changed (e.g., ablated). Otherwise, a determination can be made that the tissue was unchanged or not sufficiently changed (e.g., not ablated or not fully ablated).

In a fifth step 216 an indication is provided to the clinician/physician as to what type of tissue with which the electrode 12 is in contact. Accordingly, the ECU 32 is configured to generate a signal representative of an indicator corresponding to the type of tissue (e.g., changed (e.g., ablated) or unchanged/insufficiently changed (e.g., unablated or not fully ablated), for example) that the electrode 12 is in contact with based on the ALI calculation and comparison. As described in great detail above with respect to the use of ECI in lesion assessment, the indicator may take many forms. The description relating to the various forms of indicators set forth above applies here with equal force, and therefore, will not be repeated.

In an exemplary embodiment, in a sixth step 218 a determination is made as to whether the portion of the tissue at the particular location being evaluated has been changed (e.g., ablated). The particular location of the portion of the tissue may be determined using the mapping, visualization, and navigation system 30. If the tissue has been changed (e.g., ablated), the calculated ALI and ablation information may be stored in a storage medium, such as, for example, memory 92/116. In a seventh step 220, the system 10 then determines whether the ablation procedure can be ended. If "yes," then the ablation procedure is stopped. If "no," then the process begins again at step 210.

If, on the other hand, the tissue has not been changed (e.g., ablated), then the physician/clinician can determine whether it should be ablated. Alternatively, in a robotic application, a robotic controller, or other component of the system, can make such a determination. If the tissue should be ablated, ablative energy can be applied to the tissue at that particular location. Accordingly, the physician/clinician may move the catheter 14 to the particular location requiring ablation and then cause ablative energy to be applied. Alternatively, in a robotic application, the robotic controller may cause the catheter 14 to move to the particular location requiring ablation and then cause ablative energy to be applied. In such an embodiment, the system 30 may be used by the robotic controller to determine where the catheter is and where it needs to go, as well as to assist with the direction of the movement of the catheter to the desired location. Once the tissue is ablated, the process may then proceed starting at step 210. If, however, the tissue should not be ablated, then the ALI and ablation information may be stored in a storage medium, such as, for example, memory 92/116. The system 10 then determines whether the ablation procedure can be ended. If "yes," then the ablation procedure is stopped. If "no," then the process begins again at step 210.

Figure 22:
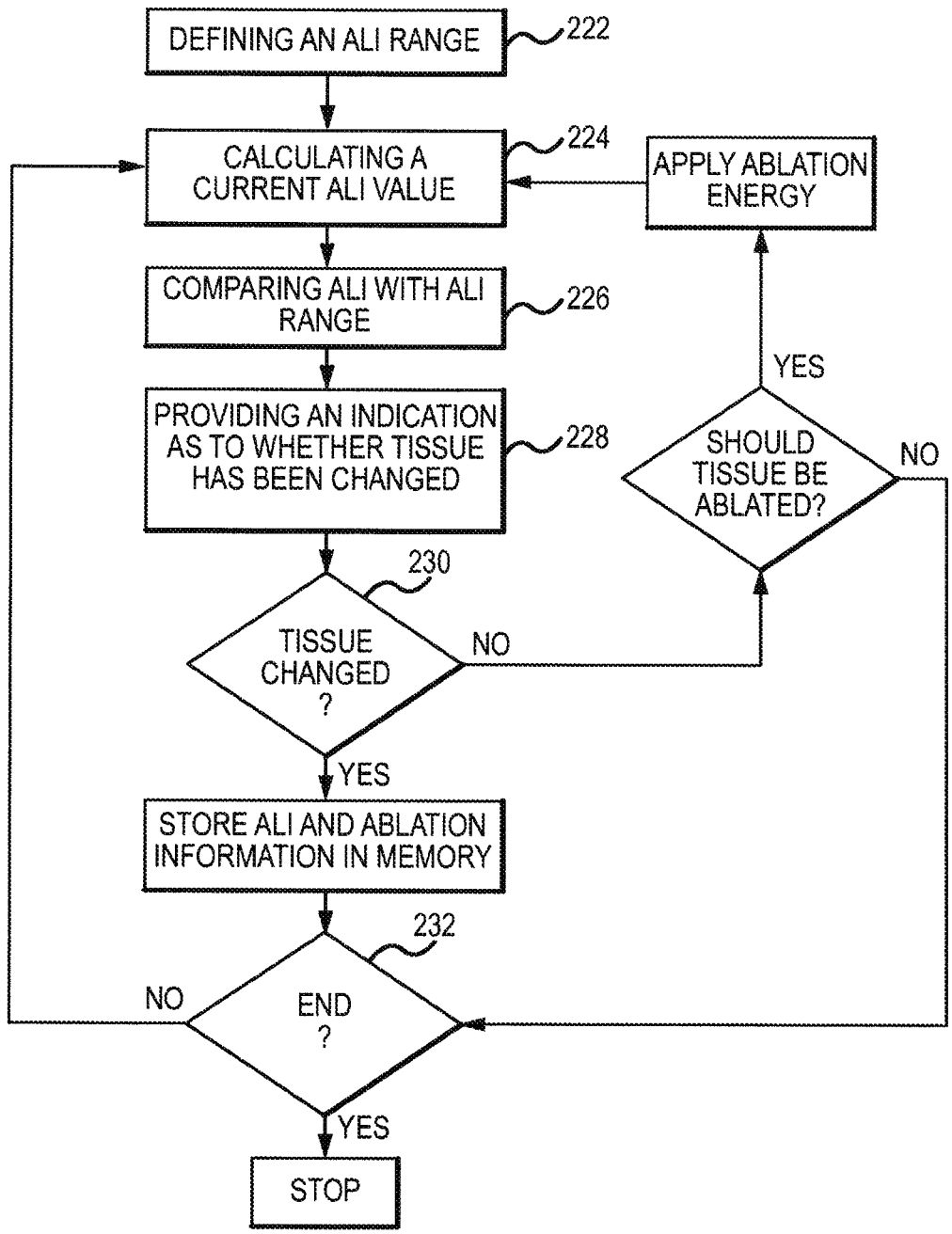

While the aforementioned embodiment is directed towards determining whether tissue has been changed (e.g., ablated), in other exemplary embodiments determinations can be made as to whether tissue has been changed as well as to the quality or extent of change (e.g., ablation) (i.e., the degree of change). One such example is illustrated in FIG. 22. In a first step 222, an ALI range is defined that has a lower threshold corresponding to an ALI value indicative of the tissue being unchanged/insufficiently changed (e.g., unablated or not fully ablated), and an upper threshold corresponding to an ALI value indicative of the tissue being changed (e.g., ablated). In an exemplary embodiment the lower threshold value equals zero and the upper threshold value equals one (i.e., ALI range is 0-1). In such an embodiment, the goal for changed (e.g., ablated) tissue would be to have an ALI value of between 0 and the immediate neighborhood of 1, and to not go much above 1 as anything exceeding 1, in this particular embodiment, would be indicative of over-ablation. These thresholds may be set by either preprogramming them into the ECU 32, or a user may input them using a conventional I/O interface. In a second step 224, a current ALI is calculated corresponding to the portion of the tissue in contact with the electrode 12. In a third step 226, the calculated ALI is compared to the ALI range. Based on this comparison, a determination can be made as to (i) whether the tissue has been changed (e.g., ablated), and (ii) if the tissue has been changed, the quality or extent of the change (e.g., ablation).

More particularly, if the calculated ALI equals zero (or nearly zero), then it can be determined that the tissue at that particular location has not been changed, or at least not sufficiently changed (e.g., the tissue is unablated or not fully ablated). If, on the other hand, the ALI is above zero, then it can be determined that the tissue has, in fact, been changed (e.g., ablated). Further, based on the particular value of the calculated ALI, it can be determined whether the tissue has been mildly changed or ablated (ALI closer to 0) or more substantially changed or ablated (ALI closer to 1). In one exemplary embodiment the ECU 32 may be configured to look up the value of the ALI in a look-up table, for example, stored in the ECU 32 or in another component of the system accessible by the ECU 32 that contains values of ALI and corresponding indications of the extent or degree of the ablation. This indication may then be communicated to the physician/clinician or robotic controller to assess whether the extent of the ablation or change in the tissue is acceptable. While the extent/quality of the ablation aspect of the invention is described with respect to this particular embodiment, it will be appreciated by those of ordinary skill in the art that it applies to any embodiment in which an ALI is calculated.

In a fourth step 228, an indication is provided to the clinician/physician as to whether the tissue that is in contact with the electrode 12 has been changed (e.g., ablated), and/or as to the degree or quality of the change (e.g., ablation). Accordingly, based on the ALI calculation and comparison, the ECU 32 is configured to generate a signal representative of an indicator corresponding to the type of tissue with which the electrode 12 is in contact. In an exemplary embodiment, the indicator, or another indicator, may also indicate the quality or extent of the ablation. As described above in great detail, these indicators may take many forms. The description set forth above relating to the indicators applies here with equal force, and therefore, will not be repeated.

In an exemplary embodiment, in a fifth step 230 a determination is made as to whether the portion of the tissue at the particular location being evaluated has been changed (e.g., ablated). In an exemplary embodiment, this inquiry may further include whether the extent to which the tissue has been changed is acceptable (i.e., meets quantitative standards). The particular location of the portion of the tissue may be determined using the mapping, visualization, and navigation system 30. If the tissue has been changed (e.g., ablated) and/or if the change in the tissue is acceptable, the calculated ALI and ablation information may be stored in a storage medium, such as, for example, memory 92/116. In a sixth step 232, the system 10 then determines whether the ablation procedure can be ended. If "yes," then the ablation procedure is stopped. If "no," then the process begins again at step 222.

If, on the other hand, the tissue has not been changed, or at least not sufficiently changed (e.g., the tissue is unablated or not fully ablated), then the physician/clinician can determine whether it should be ablated or re-ablated. Alternatively, in a robotic application, a robotic controller, or other component of the system, can make such a determination. If the tissue should be ablated or re-ablated, ablative energy can be applied to the tissue at that particular location. Accordingly, the physician/clinician may move the catheter 14 to the particular location requiring ablation and then cause ablative energy to be applied. Alternatively, in a robotic application, the robotic controller may cause the catheter 14 to move to the particular location requiring ablation and then cause ablative energy to be applied. In such an embodiment, the system 30 may be used by the robotic controller to determine where the catheter is and where it needs to go, as well as to assist with the direction of the movement of the catheter to the desired location. Once the tissue is ablated, the process may then proceed starting at step 222. If, however, the tissue should not be ablated or re-ablated, then the ALI and ablation information may be stored in a storage medium, such as, for example, memory 92/116. The system 10 then determines whether the ablation procedure can be ended. If "yes," then the ablation procedure is stopped. If "no," then the process begins again at step 222.

Figure 23:
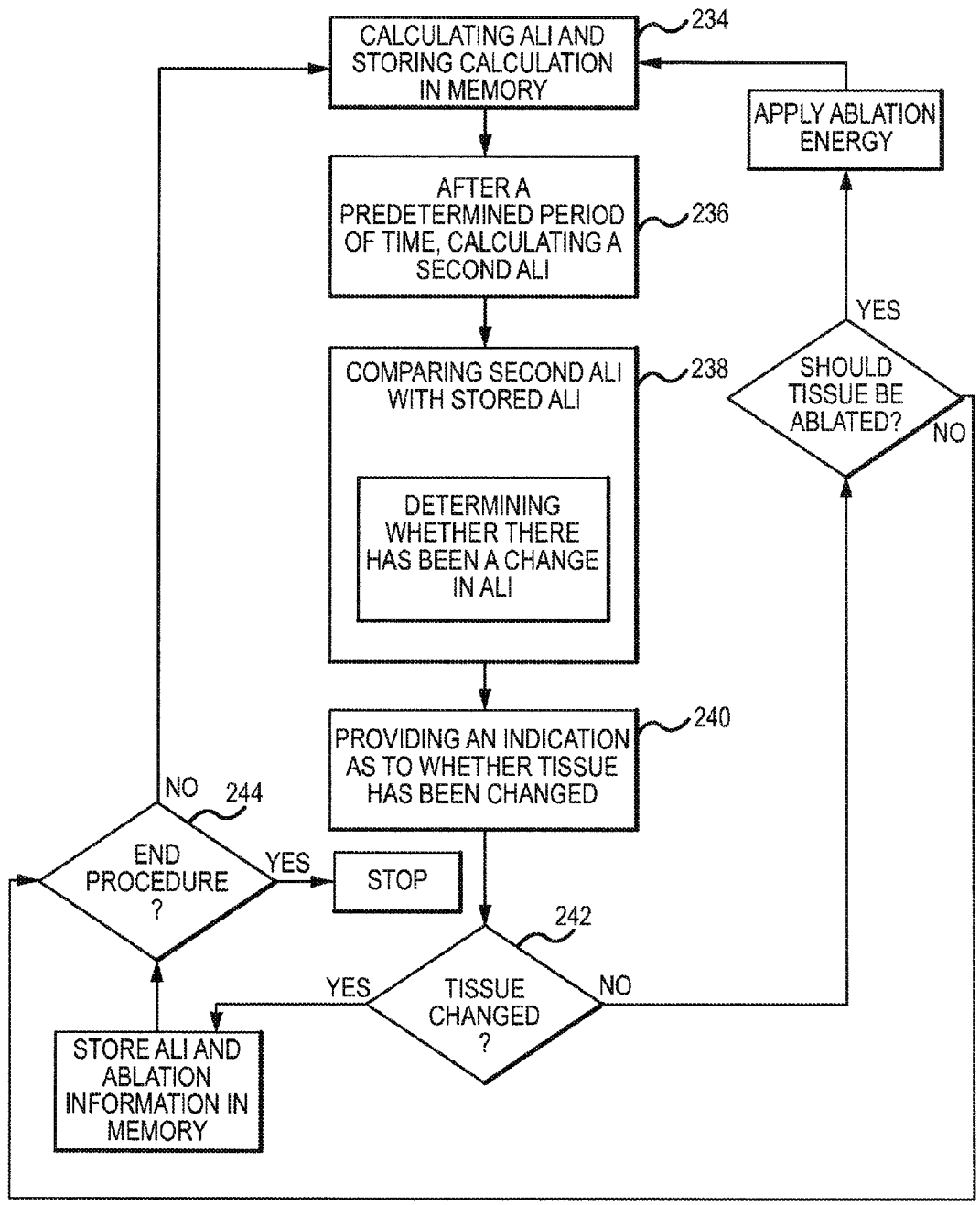

In another exemplary embodiment, rather than comparing a calculated ALI with an ALI threshold or ALI range, the change in ALI over either time or space (i.e., distance) is evaluated. In an exemplary embodiment, the change in ALI over a predetermined amount of time $$\left(\text{i.e., } \frac{dALI}{dt}\right)$$

is determined and evaluated. FIG. 23 illustrates an exemplary embodiment of a methodology based on change in ALI over time.

In a first step 234, an ALI calculation for a particular area of the tissue 16 is made and then stored in a storage medium, such as, for example, memory 92/116. In an exemplary embodiment this may correspond to the ALI at time t=1. In a second step 236, the ECU 32 calculates another ALI after a predetermined period of time has elapsed (i.e., time t=2). This calculated ALI may correspond to the same area of the tissue 16 or a different area of the tissue 16. The ECU 32 may be preprogrammed with the time interval or sampling rate that constitutes the predetermined period of time, or it may be entered by the user via a convention I/O interface.

In a third step 238, the ECU 32 compares the previously stored ALI calculation (ALI at t=1) with the current ALI calculation (ALI at t=2) and determines if there is a change, and if so, the degree of such change. No change in the ALI is indicative of the electrode remaining in contact with either changed or unchanged/insufficiently changed tissue (i.e., the electrode has not moved from unchanged or insufficiently changed (e.g., unablated or not fully ablated) tissue to changed (e.g., ablated) tissue, or vice versa, and therefore, there is no appreciable change in the ALI) or that the particular extent to which the tissue has been changed has not itself changed. A "positive" change value is indicative of the electrode 12 moving from contact with changed (e.g., ablated) tissue to unchanged/insufficiently changed (e.g., unablated or not fully ablated) tissue, or from tissue having a higher extent of change to tissue of lower extent of change (i.e., higher ALI for changed (e.g., ablated) or more changed tissue compared to lower ALI for unchanged or insufficiently changed (e.g., unablated or not fully ablated) or less changed tissue results in a positive number). Finally, a "negative" change value is indicative of the electrode 12 moving from contact with unchanged or insufficient changed (e.g., unablated or not fully ablated) tissue to changed (e.g., ablated) tissue or from tissue having a lower extent of change to tissue of a higher extent of change (i.e., lower ALI for unchanged or insufficiently changed (e.g., unablated or not fully ablated) or less changed tissue compared to higher ALI for changed (e.g., ablated) or more changed tissue results in a negative number).

In an instance where the comparison of the ALI calculations results in a change—whether positive or negative—in an exemplary embodiment, the degree of change may be taken into account such that the change must meet a predetermined threshold to be considered a change in contact from changed (e.g., ablated) to unchanged/insufficiently changed (e.g., unablated or not fully ablated) tissue (or vice versa). This allows for some change in ALI without necessarily indicating a change in the tissue.

With continued reference to FIG. 23, in a fourth step 240, an indication is provided to the clinician/physician, or to a robotic controller in a robotics-based system, as to whether the portion of the tissue that is presently in contact with the electrode 12 is changed (e.g., ablated) or unchanged/insufficiently changed (e.g., unablated or not fully ablated) tissue and/or to what extent the tissue has been changed. Accordingly, based on the comparison of ALI calculations, the ECU 32 is configured to generate signal representative of an indicator corresponding to the type of tissue with which the electrode 12 is in contact. In an exemplary embodiment, the indicator, or another indicator, may also indicate the quality or extent of the change (e.g., ablation). As described above in great detail, these indicators may take many forms. The description set forth above relating to these indicators applies here with equal force, and therefore, will not be repeated. This process repeats itself as the electrode 12 continues to move. Accordingly, each ALI calculation is saved in the memory 92/116 so that it may be compared to one or more subsequent ALI calculations.

With continued reference to FIG. 23, in an exemplary embodiment, in a fifth step 242 a determination is made as to whether the portion of the tissue at the particular location being evaluated has been changed (e.g., ablated). In another exemplary embodiment this inquiry may further include whether the extent to which the tissue has been changed is acceptable (i.e., meets certain standards). The particular location of the portion of the tissue may be determined using the mapping, visualization, and navigation system 30. If the tissue has been changed, and/or if the change is acceptable, the calculated ALI and ablation information may be stored in a storage medium, such as, for example, memory 92/116. In a sixth step 244, the system 10 then determines whether the ablation procedure can be ended. If "yes," then the ablation procedure is stopped. If "no," then the process begins again at step 234.

If, on the other hand, the tissue has not been changed, or at least not sufficiently or acceptably changed (e.g., the tissue is unablated or not fully ablated), then the physician/clinician can determine whether it should be ablated or re-ablated. Alternatively, in a robotic application, a robotic controller, or other component of the system, can make such a determination. If the tissue should be ablated or re-ablated, ablative energy can be applied to the tissue at that particular location. Accordingly, the physician/clinician may move the catheter 14 to the particular location requiring ablation and then cause ablative energy to be applied. Alternatively, in a robotic application, the robotic controller may cause the catheter 14 to move to the particular location requiring ablation and then cause ablative energy to be applied. In such an embodiment, the system 30 may be used by the robotic controller to determine where the catheter is and where it needs to go, as well as to assist with the direction of the movement of the catheter to the desired location. Once the tissue is ablated, the process may then proceed starting at step 234. If, however, the tissue should not be ablated or re-ablated, then the ALI and ablation information may be stored in a storage medium, such as, for example, memory 92/116. The system 10 then determines whether the ablation procedure can be ended. If "yes," then the ablation procedure is stopped. If "no," then the process begins again at step 234.

Figure 24:
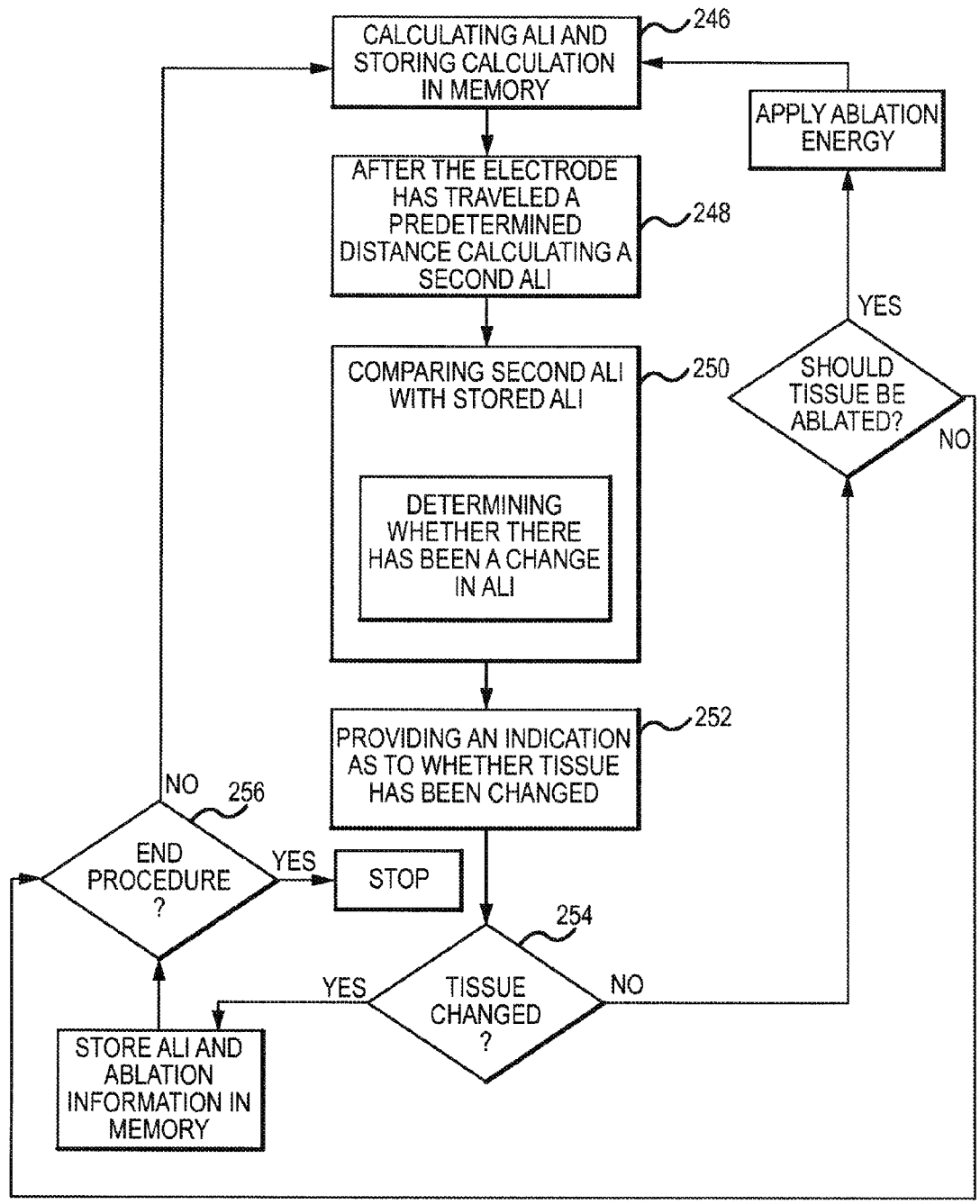

In another exemplary embodiment, besides comparing a calculated ALI with an ALI threshold or evaluating the change in the ALI over a predetermined time interval, the change in the ALI over a predetermined space or surface distance $$\left(\text{i.e., } \frac{d\,ALI}{dt}\right)$$

is determined and evaluated. FIG. 24 illustrates an exemplary embodiment of a methodology based on change in ALI over distance or space. It should be noted that this particular embodiment finds particular application in the instance wherein trabeculation is not a confounding variable or concern (i.e., the tissue being evaluated is smooth and free of trabeculae).

In a first step 246, an ALI calculation is made for a particular area of the tissue 16 and then stored in a storage medium, such as, for example, memory 92/116. In a second step 248, the ECU 32 calculates another ALI calculation after it is determined that the electrode 12 has traveled a predetermined distance either longitudinally along the longitudinal axis of a lesion, or laterally relative to the longitudinal axis to another area of the tissue 16. In an exemplary embodiment, the ECU 32 is configured to receive location data (such as x, y, z coordinates) from the mapping, visualization, and navigation system 30 and to calculate change in distance relative to prior stored location data also received from system 30. In another exemplary embodiment, system 30 is configured to process the location data to calculate a change in distance and to provide the change to the ECU 32 for it determine whether the predetermined sampling distance has been met. Accordingly, the calculation may be triggered when the electrode moves a certain distance. The predetermined distance may be programmed into the ECU 32 or may be entered by a user via a conventional I/O interface.

In a third step 250, the ECU 32 compares the previously stored ALI calculation with the current ALI calculation and determines if there is a change, and if so, the degree of such change. No change in the ALI is indicative of the electrode remaining in contact with the same type of tissue (i.e., the electrode has not moved from unchanged/insufficiently changed (e.g., unablated or not fully ablated) to changed (e.g., ablated) tissue, or vice versa, and therefore, there is no appreciable change in the ALI) or that the particular degree or extent to which the tissue has been changed has itself not changed. A "positive" change value is indicative of the electrode 12 moving from contact with changed (e.g., ablated) tissue to unchanged/insufficiently changed (e.g., unablated or not fully ablated) tissue or from tissue having a higher extent of change to tissue of lower extent of change (i.e., higher ALI for changed (e.g., ablated) or more changed tissue compared to lower ALI for unchanged or not sufficiently changed (e.g., unablated or not fully ablated) or less changed tissue results in a positive number). Finally, a "negative" change value is indicative of the electrode 12 moving from contact with unchanged or insufficiently changed (e.g., unablated or not fully ablated) tissue to changed (e.g., ablated) tissue, or from tissue having a lower extent of change to tissue of a higher extent of change (i.e., lower ALI for unchanged or not sufficiently changed (e.g., unablated or not fully ablated) or less changed tissue compared to higher ALI for changed (e.g., ablated) or more changed tissue results in a negative number).

In an instance where the comparison of the ALI calculations results in a change—whether positive or negative—in an exemplary embodiment, the degree of change may be taken into account such that the change must meet a predetermined threshold to be considered a change in contact from changed (e.g., ablated) to unchanged or insufficiently changed (e.g., unablated or not fully ablated) tissue (or vice versa). This allows for some change in ALI without necessarily indicating a change in the tissue.

With continued reference to FIG. 24, in a fourth step 252, an indication is provided to the clinician/physician, or to a robotic controller in a robotics-based system, as to whether the portion of the tissue that is presently in contact with the electrode 12 is changed (e.g., ablated) or unchanged/insufficiently changed (e.g., unablated or not fully ablated) tissue and/or to what extent the tissue has been changed (e.g., ablated). Accordingly, based on the comparison of ALI calculations, the ECU 32 is configured to generate signal representative of an indicator corresponding to the type of tissue with which the electrode 12 is in contact. In an exemplary embodiment, the indicator, or another indicator, may also indicate the quality or extent of the change (e.g., ablation). As described above in great detail, these indicators may take many forms. The description set forth above relating to these indicators applies here with equal force, and therefore, will not be repeated. This process repeats itself as the electrode 12 continues to move. Accordingly, each ALI calculation is saved in the memory 92/116 so that it may be compared to one or more subsequent ALI calculations.

With continued reference to FIG. 24, in an exemplary embodiment, in a fifth step 254 a determination is made as to whether the portion of the tissue at the particular location being evaluated has been changed (e.g., ablated). In another exemplary embodiment this inquiry may further include whether the extent to which the tissue has been changed is acceptable (i.e., meets certain standards). The particular location of the portion of the tissue may be determined using the mapping, visualization, and navigation system 30. If the tissue has been changed and/or if the change is acceptable, the calculated ALI and ablation information may be stored in a storage medium, such as, for example, memory 92/116. In a sixth step 256, the system 10 then determines whether the ablation procedure can be ended. If "yes," then the ablation procedure is stopped. If "no," then the process begins again at step 246.

If, on the other hand, the tissue has not been changed, or at least not sufficiently or acceptably changed (e.g., the tissue is unablated or not fully ablated), then the physician/clinician can determine whether it should be ablated or re-ablated. Alternatively, in a robotic application, a robotic controller, or other component of the system, can make such a determination. If the tissue should be ablated or re-ablated, ablative energy can be applied to the tissue at that particular location. Accordingly, the physician/clinician may move the catheter 14 to the particular location requiring ablation and then cause ablative energy to be applied. Alternatively, in a robotic application, the robotic controller may cause the catheter 14 to move to the particular location requiring ablation and then cause ablative energy to be applied. In such an embodiment, the system 30 may be used by the robotic controller to determine where the catheter is and where it needs to go, as well as to assist with the direction of the movement of the catheter to the desired location. Once the tissue is ablated, the process may then proceed starting at step 246. If, however, the tissue should not be ablated or re-ablated, then the ALI and ablation information may be stored in a storage medium, such as, for example, memory 92/116. The system 10 then determines whether the ablation procedure can be ended. If "yes," then the ablation procedure is stopped. If "no," then the process begins again at step 246.

Figure 25:
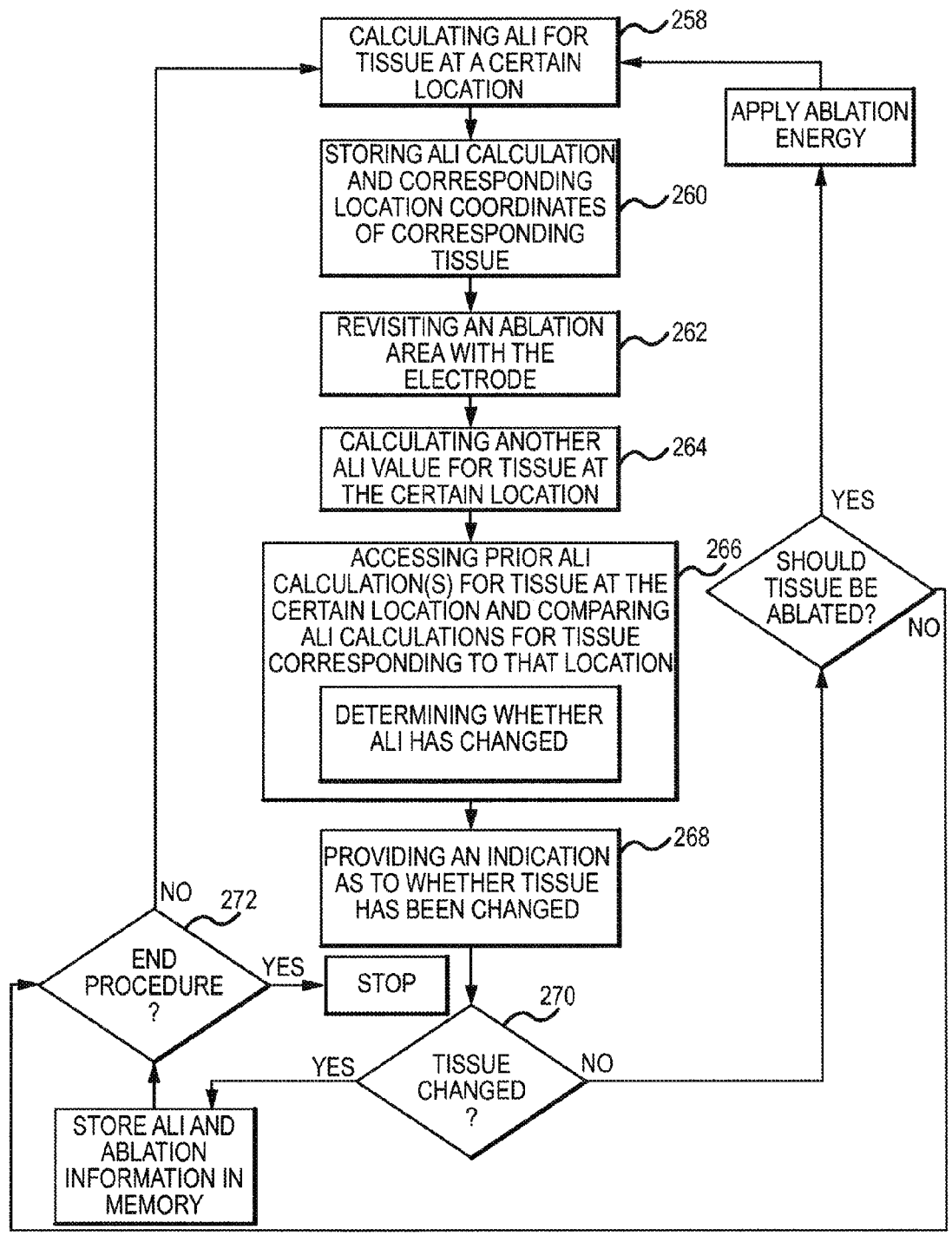

In another exemplary embodiment, two or more ALI calculations for tissue at a particular location at two different points in time can be evaluated to determine whether the tissue at that particular location has been changed (e.g., ablated), and/or to what extent the tissue has been changed. More specifically, and with reference to FIG. 25, in a first step 258 an ALI calculation is made for tissue at a particular location. In a second step 260, the ALI calculation and the corresponding location—which may be acquired from the mapping, visualization and navigation system 30—are saved in a storage medium, such as, for example and without limitation, the memory 92/116.

As the electrode 12 moves, a number of ALI calculations can be made. Once the procedure has been completed, in a third step 262, the electrode 12 can be brought back over the area that was to be ablated to determine if tissue at a particular location was, in fact, changed, and/or to what extent. In a fourth step 264, as the electrode visits each location for which a prior ALI calculation was made, another ALI calculation is made. In a fifth step 266, the ECU 32 accesses the prior ALI calculation that corresponds to the particular location, and compares the ALI calculations corresponding to the particular location to determine whether the ALI has changed. As described in greater detail above, whether the ALI value, or the change therein, meets, exceeds, or falls below a predetermined threshold or ALI range, the ECU 32 is able to determine whether the tissue at that particular location has been changed (e.g., ablated), and/or to what extent. This process then continues as the electrode 12 continues to move along or about a perceived lesion line or area, or as long as the clinician/physician desires.

In an exemplary embodiment, in a sixth step 268, the ECU 32 may be configured to provide an indication of the respective ALI values, which a user may take into consideration and make a determination as to whether the tissue is changed (e.g., ablated) or unchanged/insufficiently changed (e.g., unablated or not fully ablated), and/or to what extent the tissue was changed. In either instance, the description set forth in great detail above relating to the generation and/or provision of indicators applies here with equal force, and therefore, will not be repeated. Additionally, the description set forth above relating to the tolerances and/or the substantiality of the change in ALI applies here with equal force, and therefore, likewise will not be repeated here.

In an exemplary embodiment, in a seventh step 270 a determination is made as to whether the portion of the tissue at the particular location being evaluated has been changed (e.g., ablated). In another exemplary embodiment this inquiry may further include whether the extent to which the tissue has been changed is acceptable (i.e., meets certain standards such that the tissue has been changed). The particular location of the portion of the tissue may be determined using the mapping, visualization, and navigation system 30. If the tissue has been changed and/or if the change is acceptable, the calculated ALI and ablation information may be stored in a storage medium, such as, for example, memory 92/116. In an eighth step 272, the system 10 then determines whether the ablation procedure can be ended. If "yes," then the ablation procedure is stopped. If "no," then the process begins again at step 258.

If, on the other hand, the tissue has not been changed, or at least not sufficiently or acceptably changed (e.g., the tissue is unablated or not fully ablated), then the physician/clinician can determine whether it should be ablated or re-ablated. Alternatively, in a robotic application, a robotic controller, or other component of the system, can make such a determination. If the tissue should be ablated or re-ablated, ablative energy can be applied to the tissue at that particular location.

Accordingly, the physician/clinician may move the catheter 14 to the particular location requiring ablation and then cause ablative energy to be applied. Alternatively, in a robotic application, the robotic controller may cause the catheter 14 to move to the particular location requiring ablation and then cause ablative energy to be applied. In such an embodiment, the system 30 may be used by the robotic controller to determine where the catheter is and where it needs to go, as well as to assist with the direction of the movement of the catheter to the desired location. Once the tissue is ablated, the process may then proceed starting at step 258. If, however, the tissue should not be ablated or re-ablated, then the ALI and ablation information may be stored in a storage medium, such as, for example, memory 92/116. The system 10 then determines whether the ablation procedure can be ended. If "yes," then the ablation procedure is stopped. If "no," then the process begins again at step 258.

In another exemplary embodiment, rather than evaluating the finite or raw ALI calculation or determining a change in two ALI calculations, the rate of change of the ALI or the slope of a line between at least two ALI calculations over a predetermined amount or time $$\left( \text{i.e., } \frac{dALI}{dt} \right)$$

is determined and used to assess lesion formation. More particularly, when the electrode 12 changes from one type of tissue (e.g., changed tissue) to another type of tissue (e.g., unchanged/insufficiently changed tissue), or from tissue that is more changed to tissue that is less changed, the rate of change or the change in the slope over a predetermined amount of time is most evident. In other words, if the electrode 12 remains in contact with either changed (e.g., ablated) tissue or unchanged or insufficiently changed (e.g., unablated or not fully ablated) tissue, respectively, the rate of change in the ALI may not be appreciable. However, when the electrode 12 moves from changed to unchanged or insufficiently changed tissue (or from tissue that is more changed to tissue that is less changed), or vice versa, the rate of change in the ALI may be appreciable. Thus, if the rate of change over a predetermined period of time meets, exceeds, or falls below (depending on the circumstances) a predetermined threshold value, then one is able to determine what type of tissue with which the electrode 12 is currently in contact and/or the extent to which that tissue was changed (e.g., ablated). Accordingly, the rate of change in ALI or the change in the slope over a predetermined period of time can be useful in assessing lesion formation.

Figure 26:
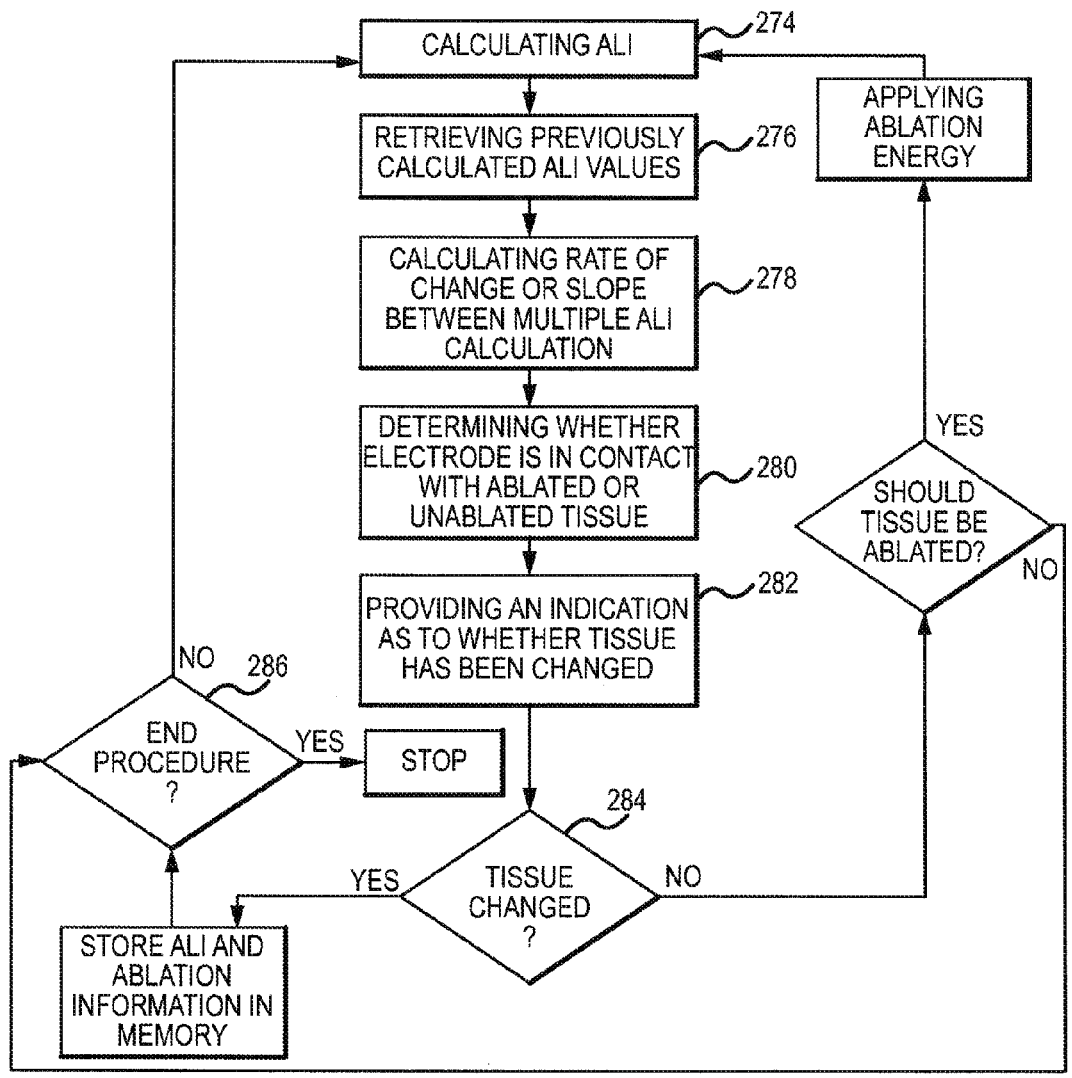

FIG. 26 illustrates one exemplary embodiment of a methodology that uses the rate of change of the ALI. In this embodiment, the memory 92/116 stores a predetermined number of previously calculated ALI calculations. As described above, the memory 92/116 may be part of the ECU 32 or may be a separate and distinct component that is accessible by the ECU 32 such that the ECU 32 may retrieve the stored ALIs. In an exemplary embodiment, the ECU 32 is configured to access the memory 92/116 and to calculate the rate of change in the ALI or the slope of a line drawn between a current or most recent ALI calculation and one or more previously calculated ALIs. Depending on if the rate of change meets, exceeds, or falls below a predetermined threshold that is programmed into ECU 32, the ECU 32 may be configured to recognize that the electrode 12 is in contact with changed (e.g., ablated) or unchanged/insufficiently changed (e.g., unablated or not fully ablated) tissue (or tissue that is more or less changed), or may simply provide the rate of change to a user for the user to determine the type of tissue with which the electrode is in contact or the extent to which the tissue is changed (e.g., ablated).

Accordingly, with continued reference to FIG. 26, in a first step 274 a current ALI is calculated and may be stored in the memory 92/116. In a second step 276, the ECU 32 accesses the memory 92/116 to retrieve one or more previously calculated ALIs. In a third step 278, the rate of change or slope between the current ALI and the one or more previously calculated ALIs stored in the memory 92/116 is calculated. In a fourth step 280, the ECU 32 determines whether the electrode 12 is in contact with changed (e.g., ablated) or unchanged/insufficiently changed (e.g., unablated or not fully ablated) tissue (or the extent to which the tissue was changed) based on the calculated rate of change. In an exemplary embodiment, in a fifth step 282, an indication may be provided to the clinician/physician as to whether the tissue that is presently in contact with the electrode 12 is changed (e.g., ablated) or unchanged/insufficiently changed (e.g., unablated or not fully ablated) tissue, or to determine to what extent that tissue has been changed (e.g., ablated). Accordingly, the ECU 32 may be further configured to generate a signal representative of an indicator corresponding to the type of tissue with which the electrode 12 is in contact. In an exemplary embodiment, this indicator or another indicator may also indicate the extent or quality of the ablation or the change in the tissue. The description set forth in great detail above relating to the generation and/or provision of such indicators applies here with equal force, and therefore, will not be repeated.

In an exemplary embodiment, in a sixth step 286 a determination is made as to whether the portion of the tissue at the particular location being evaluated has been changed (e.g., ablated). In another exemplary embodiment this inquiry may further include whether the extent to which the tissue has been changed is acceptable (i.e., meets certain standards such that the tissue has been changed). The particular location of the portion of the tissue may be determined using the mapping, visualization, and navigation system 30. If the tissue has been changed or ablated and the change (e.g., ablation) is acceptable, the calculated ALI and ablation information may be stored in a storage medium, such as, for example, memory 92/116. In a seventh step 288, the system 10 then determines whether the ablation procedure can be ended. If "yes," then the ablation procedure is stopped. If "no," then the process begins again at step 274.

If, on the other hand, the tissue has not been changed, or at least not sufficiently or acceptably changed (e.g., the tissue is unablated or not fully ablated), then the physician/clinician can determine whether it should be ablated or re-ablated. Alternatively, in a robotic application, a robotic controller, or other component of the system, can make such a determination. If the tissue should be ablated or re-ablated, ablative energy can be applied to the tissue at that particular location. Accordingly, the physician/clinician may move the catheter 14 to the particular location requiring ablation and then cause ablative energy to be applied. Alternatively, in a robotic application, the robotic controller may cause the catheter 14 to move to the particular location requiring ablation and then cause ablative energy to be applied. In such an embodiment, the system 30 may be used by the robotic controller to determine where the catheter is and where it needs to go, as well as to assist with the direction of the movement of the catheter to the desired location. Once the tissue is ablated, the process may then proceed starting at step 274. If, however, the tissue should not be ablated or re-ablated, then the ALI and ablation information may be stored in a storage medium, such as, for example, memory 92/116. The system 10 then determines whether the ablation procedure can be ended. If "yes," then the ablation procedure is stopped. If "no," then the process begins again at step 274.

In another exemplary embodiment, rather than evaluating finite or raw ALI calculations or the rate of change in such calculations, ALI may be used, in part, to calculate an ALI rate (ALIR). The ALIR can be used in lesion assessment. In an exemplary embodiment, the ECU 32 is configured to calculate the ALIR, however, the present invention is not meant to be so limited. Rather, other processors or components may be employed to perform the calculation.

In simple terms, the ALIR is calculated by dividing the change in ALI over a predetermined amount of time by the change in the distance or position of the electrode 12 over the same predetermined amount of time. The change in the ALI is calculated by sampling the ALI calculations performed by the ECU 32 at a predetermined rate and then determining the difference between a current calculation and the most recent previous calculation, for example, that may be stored in the memory 92/116. In another exemplary embodiment, the difference may be between a current calculation and multiple previous calculations, or an average of previous calculations.

In an exemplary embodiment, the ECU 32 samples the calculated ALI at a predetermined sampling rate, and then calculates the change in the ALI over that time interval. It will be appreciated by those of ordinary skill in the art that the ALI may be sampled at any number of time intervals or rates. For example, in one embodiment using known techniques, the sampling is timed or synchronized to coincide with the cardiac cycle of the patient's heart so as to always sample at the same point in the cardiac cycle. In another embodiment, the sampling of the ALI is dependent upon a triggering event rather than a defined time interval. For instance, the sampling of the ALI may be dependent upon the change in the distance/position of the electrode 12 meeting a predetermined threshold. More specifically, when it is determined that the electrode 12 has moved a predetermined distance, the ECU 32 will sample the ALI over the time interval it took the electrode 12 to move the predetermined distance. Accordingly, it will be appreciated by those of ordinary skill in the art that many different sampling rates and/or techniques may be used to determine the change in ALI.

With respect to the change in distance/location of the electrode, as described above this change may be calculated by the ECU 32 based on location coordinates provided to it by the system 30, or may be calculated by the system 30 and then provided to the ECU 32. As with the change in ALI, the change in distance or location is determined by sampling the location coordinates of the electrode 12 at a predetermined sampling rate. From this, the change in distance over time can be derived. As with the sampling of the ALI calculations, the location coordinates of the electrode 12 are sampled at a predetermined sampling rate and then the change in the location is calculated over that time interval. It will be appreciated by those of ordinary skill in the art that the location/position may be sampled at various rates and using various techniques (e.g., synchronization with cardiac cycle). Accordingly, the present invention is not limited one particular sampling rate/technique. It should be noted that this particular embodiment finds particular application in the instance wherein trabeculation is not a confounding variable or concern (i.e., the tissue being evaluated is smooth and free of trabeculae.

Once the two "change" calculations have been made, the ECU 32 is able to calculate the ALIR by dividing the change in the ALI by the change in the distance or location of the electrode 12. In an exemplary embodiment, the calculated ALIR is stored in a storage medium, such as, for example, memory 92/116, that is accessible by the ECU 32.

Figure 27:
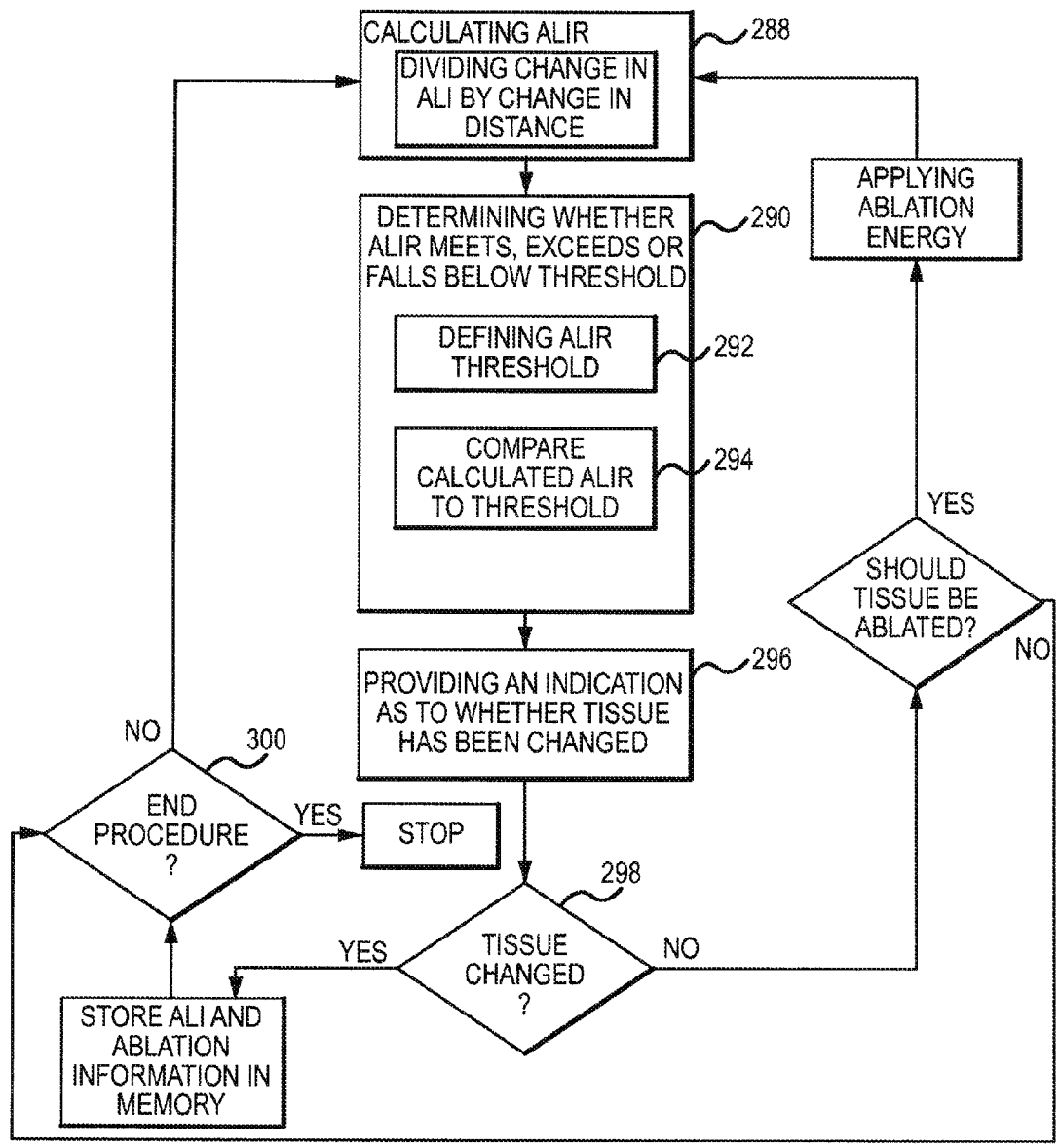

Once the ALIR has been calculated, it may be used to assess, among other things, what type of tissue the electrode 12 is in contact with (e.g., changed (e.g., ablated) versus unchanged/insufficiently changed (e.g., unablated or not fully ablated) tissue), and/or to what extent the tissue has been changed. In an exemplary embodiment illustrated in FIG. 27, the ALIR is calculated in a first step 288 by dividing the change in ALI by the change in distance. In a second step 290, the calculated ALIR is evaluated to determine whether the calculated ALIR meets, exceeds, or falls below a predefined threshold value. Depending on where the calculated ALIR falls with respect to the threshold, a determination can be made as to what type of tissue the electrode 12 is in contact with, and/or to what extent the tissue has been changed.

More particularly, in a first substep 292 of step 290, an ALIR threshold is defined. This threshold may be set by either preprogramming it into the ECU 32, or a user may manually input it into the ECU 32 using a conventional I/O interface.

In a second substep 294 of second step 290, the calculated ALIR is compared to the predefined threshold. Based on this comparison, the determination is made as to what type of tissue the electrode 12 is contacting (e.g., changed (e.g., ablated) or unchanged/insufficiently changed (e.g., unablated or not fully ablated)) or from what type of tissue from which the electrode has traveled. To what extent the tissue has been changed may also be determined. In an exemplary embodiment, in a third step 296, the ECU 32 may be configured to provide an indication as to the value of the ALIR, which a user may take into consideration and make a determination as to whether the tissue is changed (e.g., ablated) or unchanged/insufficiently changed (e.g., unablated or not fully ablated), and/or to what extent the tissue has been changed. The description set forth in great detail above relating to the generation and/or provision of indicators applies here with equal force, and therefore, will not be repeated.

In an exemplary embodiment, in a fourth step 298 a determination is made as to whether the portion of the tissue at the particular location being evaluated has been changed (e.g., ablated). In another exemplary embodiment this inquiry may further include whether the extent to which the tissue has been changed is acceptable (i.e., meets certain standards such that the tissue has been changed). The particular location of the portion of the tissue may be determined using the mapping, visualization, and navigation system 30. If the tissue has been changed (e.g., ablated) and the change (e.g., ablation) is acceptable, the calculated ALI/ALIR and ablation information may be stored in a storage medium, such as, for example, memory 92/116. In a fifth step 300, the system 10 then determines whether the ablation procedure can be ended. If "yes," then the ablation procedure is stopped. If "no," then the process begins again at step 288.

If, on the other hand, the tissue has not been changed, or at least not sufficiently or acceptably changed (e.g., the tissue is unablated or not fully ablated), then the physician/clinician can determine whether it should be ablated or re-ablated. Alternatively, in a robotic application, a robotic controller, or other component of the system, can make such a determination. If the tissue should be ablated or re-ablated, ablative energy can be applied to the tissue at that particular location. Accordingly, the physician/clinician may move the catheter 14 to the particular location requiring ablation and then cause ablative energy to be applied. Alternatively, in a robotic application, the robotic controller may cause the catheter 14 to move to the particular location requiring ablation and then cause ablative energy to be applied. In such an embodiment, the system 30 may be used by the robotic controller to determine where the catheter is and where it needs to go, as well as to assist with the direction of the movement of the catheter to the desired location. Once the tissue is ablated, the process may then proceed starting at step 288. If, however, the tissue should not be ablated or re-ablated, then the ALI/ALIR and ablation information may be stored in a storage medium, such as, for example, memory 92/116. The system 10 then determines whether the ablation procedure can be ended. If "yes," then the ablation procedure is stopped. If "no," then the process begins again at step 288.

It should be noted that while the ALI described in great detail above is calculated as a function of time and takes into account confounding variables of temperature, contact force, and trabeculation, in other exemplary embodiments indices are calculated that take into account additional or fewer variables. These indices remain within the spirit and scope of the present invention. For example, in another exemplary embodiment, the ECU 32 may be configured to receive one or more inputs of the components of the complex impedance and contact force, for example, and to then generate an index to allow for the assessment of lesion formation. The generated index may be calculated based on discrete values for each input, on the respective changes in the input values, or a combination of both. Once calculated, the index may be evaluated in a similar manner as that described above with respect to ECI and ALI calculations to assess lesion formation. Accordingly, in such an embodiment, contact force is taken into account in the index calculation as opposed to correcting or scaling a calculated index (e.g., ECI) as a result of the impact contact force may have on the index calculation.

Accordingly, indices taking into account different variables may be calculated that reduce the influence these variables have on the calculated index. As a result, one or more indices can be calculated that are substantially insensitive to variables such as temperature and contact force, and responsive virtually solely on tissue changes caused by ablation to determine simply whether the tissue has been changed or ablated and/or to what extent the tissue has been changed (e.g., ablated).

While the description with respect to lesion assessment has been generally focused on the use of ECI, or other derivatives thereof, lesion assessment can be carried out using other methodologies or techniques. For example, in an exemplary embodiment, the complex impedance, and/or the components thereof, may be used to assess tissue temperature and/or lesion formation.

In one exemplary embodiment, the change in the phase angle of the impedance can be evaluated to determine what type of tissue the electrode 12 is in contact with. More particularly, a constant voltage source, or more preferably, a constant current source, is used and the shift in the phase angle (i.e., change in the phase angle) is measured. When the electrode 12 is in contact with a lesion or tissue that has been changed (e.g., ablated), the phase angle change decreases. When the electrode 12 moves from contact with changed (e.g., ablated) to unchanged/insufficiently changed (e.g., unablated or not fully ablated) tissue, the phase angle change increases. Accordingly, by assessing or evaluating the change in the phase angle, a determination can be made as to what type of tissue with which the electrode is in contact.

In another exemplary embodiment, the complex impedance itself can be used to assess lesion formation. One challenge with the use of complex impedance is that the change in the impedance caused by temperature—as opposed to change in the tissue (i.e., ablation of tissue)—must be taken into account and separated from the calculation. One difference between the two is that when a change in the impedance is induced by a change in the temperature, the impedance may appreciably recover once the tissue has cooled. However, if the change is induced due to actual change in the tissue (i.e., the tissue has been changed (e.g., ablated)), the change in the impedance is residual and does not recover to predetermined levels/values. Accordingly, once the two changes in impedance are separated such that the change due to ablation is isolated, one can assess the lesion formation based on the magnitude of the change in the impedance, and therefore, determine whether the tissue at a particular location has been changed (e.g., ablated) or unchanged/insufficiently changed (e.g., unablated or not fully ablated).

Likewise, one could use the temperature induced change in complex impedance to calculate temperature changes. For example, if the electrode 12 is held in a constant position (or returned to a position previously measured), the electrode 12 may observe an impedance change over time, e.g., the phase angle, that corresponds to a drop in tissue temperature after ablation. As the tissue cools and returns to ambient temperatures, the change in the phase angle will level off. Particularly in use with an irrigated catheter, where tissue temperature changes may be difficult to measure, the changes in the impedance may allow the clinician to determine the tissue temperature and, as a result, determine when it is either safe or dangerous to resume ablation without over heating the tissue.

One additional variable to account for in this technique or methodology is the contact force applied to the electrode 12 against the tissue. The contact force may change with tissue temperature, which can have an impact on the impedance measurements. Accordingly, the contact force can be measured as described above and taken into account to determine and isolate the change in impedance induced solely by the change in the tissue properties or attributes.

Whether the complex impedance or constituent components thereof are used to assess lesion formation, an indication of the measurements/calculations and/or determinations as to whether tissue at a particular location has been changed (e.g., ablated) may be communicated or displayed in the same manner described above. Accordingly, such discussion will not be repeated here.

Whether ECI, a derivative thereof, ALI or other similar index, complex impedance, or the constituent components of the impedance are used for lesion assessment, in an exemplary embodiment the ECU 32 is programmed with a computer program (i.e., software) encoded on a computer storage medium for assessing whether tissue at a particular location has been changed (e.g., ablated). Accordingly, the program includes code for carrying out one or more of the various techniques/methodologies described above.

The computer program may be a part of a system provided for identifying the location of a device or for visualization, mapping, and navigation of internal body structures, such as, for example, system 30. As described above, such systems include the EnSite NavX™ System commercially available from St. Jude Medical, Inc. and as generally shown with reference to commonly assigned U.S. Pat. No. 7,263,397 entitled "Method and Apparatus for Catheter Navigation and Location and Mapping in the Heart," the disclosure of which is hereby incorporated herein by reference in its entirety. Alternative systems include Biosense Webster Carto™ System, commonly available fluoroscopy systems or a magnetic location system such as the gMPS system from Mediguide Ltd., and as generally shown with reference to U.S. Pat. No.

7,386,339 entitled "Medical Imaging and Navigation System", the disclosure of which is incorporated herein by reference in its entirety.

Figure 28:
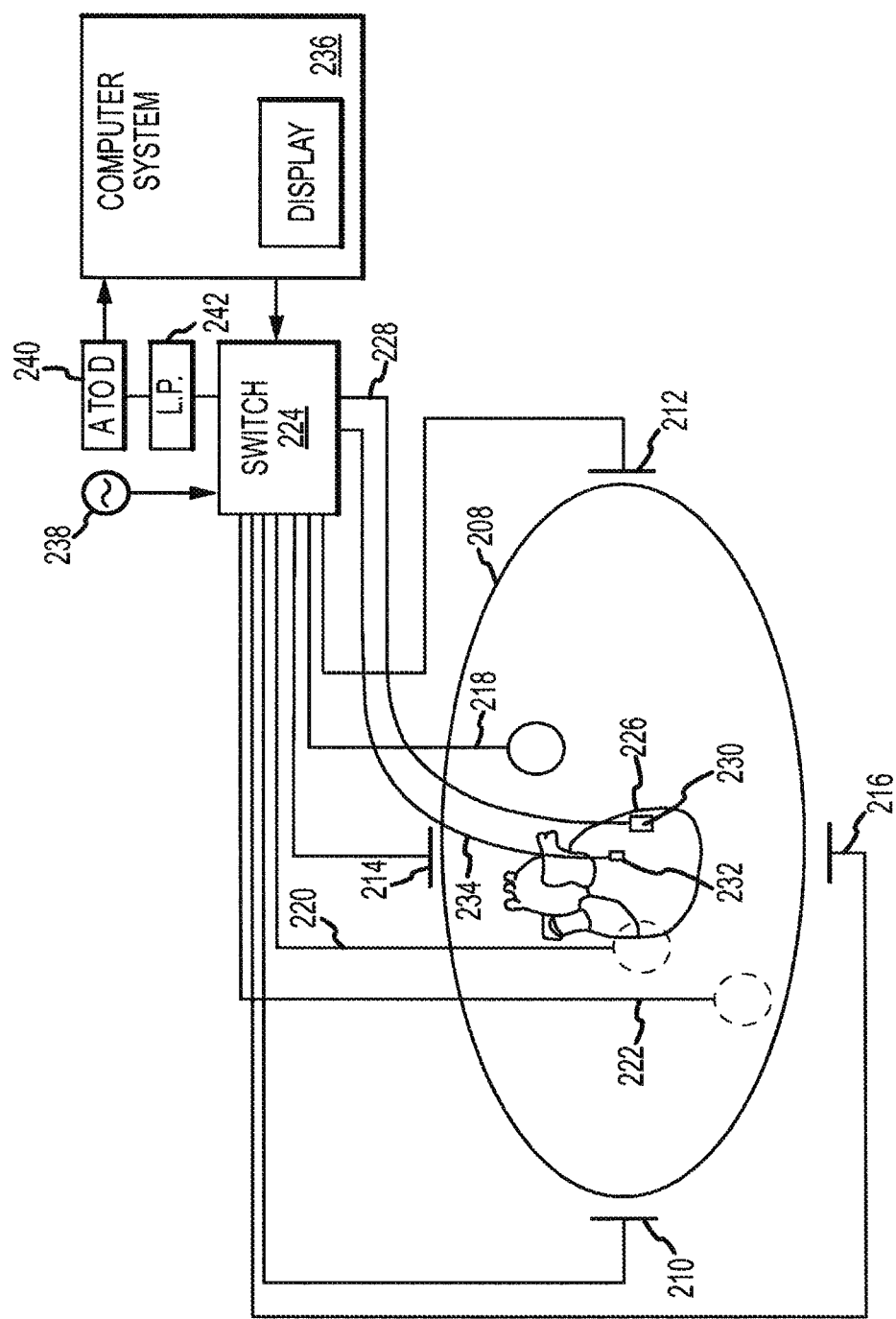
FIG. 28 is a schematic diagram of a visualization, mapping, and 3D navigation system in accordance with the present teachings.

In use, it can be advantageous to create a map in real time. This step is conducted differently in each of the systems known in the art. For illustration purposes only, it will be described in the context of the EnSite System, but may be readily adapted for use in other systems. Briefly, FIG. 28 shows a system level diagram in schematic form. The patient 208 is depicted as an oval for clarity. Three sets of surface electrodes are shown as 210, 212 along a Y-axis; as 214, 216 along an X-axis; and 218, 220 along a Z-axis. Patch electrode 218 is shown on the surface closest the observer and patch 220 is shown in outline form to show the placement on the back of patient 208. An additional patch electrode called a "belly" patch is also seen in the figure as patch electrode 222. Each patch electrode is independently connected to a multiplex switch 224. The subject tissue 226 lies between these various sets of patch electrodes. Also seen in this figure is a representative catheter 228 having a single distal electrode 230 for clarity. A fixed reference electrode 232 attached to a heart wall is also seen in the figure on an independent catheter 234.

Each patch electrode is coupled to the switch 224 and pairs of electrodes are selected by software running on computer 236, which couples the patches to the signal generator 238. A pair of electrodes, for example 210, 212, are excited by the signal generator 238 and they generate a field in the body of the patient 208 and the heart 226. During the delivery of the current pulse the remaining patch electrodes are referenced to the belly patch 208 and the voltages impressed on these remaining electrodes are measured by the A to D converter 240. Suitable low pass filtering of the digital data is subsequently performed in software to remove electronic noise and cardiac motion artifact after suitable low pass filtering in filter 242. In this fashion, the surface patch electrodes are divided into driven and non-driven electrode sets. While a pair of electrodes is driven by the current generator 238, the remaining non-driven electrodes are used as references to synthesize the orthogonal drive axes.

All of the raw patch voltage data is measured by the A to D converter 240 and stored in the computer under the direction of software. This electrode excitation process occurs rapidly and sequentially as alternate sets of patch electrodes are selected and the remaining members of the set are used to measure voltages. This collection of voltage measurements is referred to herein as the "patch data set." The software has access to each individual voltage measurement made at each patch during each excitation of each pair of electrodes.

The raw patch data is used to determine the "raw" location in three dimensional space (x, y, z) of the electrodes inside the heart, such as the roving electrode 230. The patch data is also used to create a respiration compensation value used to improve the raw location data for the electrode locations.

In use, the roving electrode 230 is swept around in the heart chamber while the heart is beating collecting a large number of electrode locations. Electrode 230 may be moved manually by a physician/clinician or, alternatively, may be manipulated by a robotic system that is driven, at least in part, by system 30. These data points are taken at all stages of the heart beat and without regard to the cardiac phase. Since the heart changes shape during contraction only a small number of the points represent the maximum heart volume. By selecting the most exterior points, it is possible to create a "shell" representing the shape of the tissue. The location attribute of the electrodes within the heart are measured while the electric field is impressed on the heart by the surface patch electrodes.

It is possible to also collect electrophysiological (EP) data and ECI data at the same time that the location data is collected. If the ECI data, for example, is collected at the same time the location data is collected, a particular set of ECI data may be associated by the ECU 32 with a particular location. This data may later be used in a number of fashions. First, the ECI data may be used to determine or assist in determining which location data points represent the outermost data points, or those points that are in actual contact with the tissue 226, and thus, are the most reliable points for generating the shell representing the shape of the tissue 226.

Likewise, the stored ECI data may be used to generate an ECI map, which can be used to display tissue characteristics to the operator, e.g., display tissue types, existing lesions from prior procedures, and the like. Likewise, it would be advantageous to allow the operator to add markers to the map, e.g., to mark manually mark a location he expects a lesion to have formed, but which is not reflected in an ECI reading, or to allow for the automatic marking of locations that have certain characteristics or that are of interest. While the above discusses the combination of ECI with location data, it is understood that the location data can also be combined with CECI data, or ALI data as well.

The combination of ECI, CECI, or ALI data with a robotic system would be particularly advantageous, as ECI/CECI/ALI assisted electroanatomical maps could be quickly and safely generated by a robotic system. As ECI would allow the robotic controller to slow the system as it approached tissue, it would increase safety as well as accuracy. In addition, ECI data, CECI data, ALI data, or any of the other data described above would allow the system to highlight areas of concern for the robotic controller to return to for further ablation.

The stored ECI data along with the location data can also be used later in the procedure to provide a baseline comparison to a current ECI reading, and thus, demonstrate if tissue changes have occurred, e.g., due to ablation. A map of these tissue changes can be generated, e.g., displaying a change in ECI ($\Delta$ECI) or a rate of change in ECI. This information can be displayed in a number of fashions, with, for example, different colors on a 3D map of the subject tissue representing particular ECI values, or representing changes in ECI values (e.g., $\Delta$ECI). This data can be placed onto a geographical map of the location points selected as the shell for display.

Additionally, the system 30 may include the ECU 32 and the display 34 among other components. However, in another exemplary embodiment, the ECU 32 is a separate and distinct component that is electrically connected to the system 30.

Figure 29:
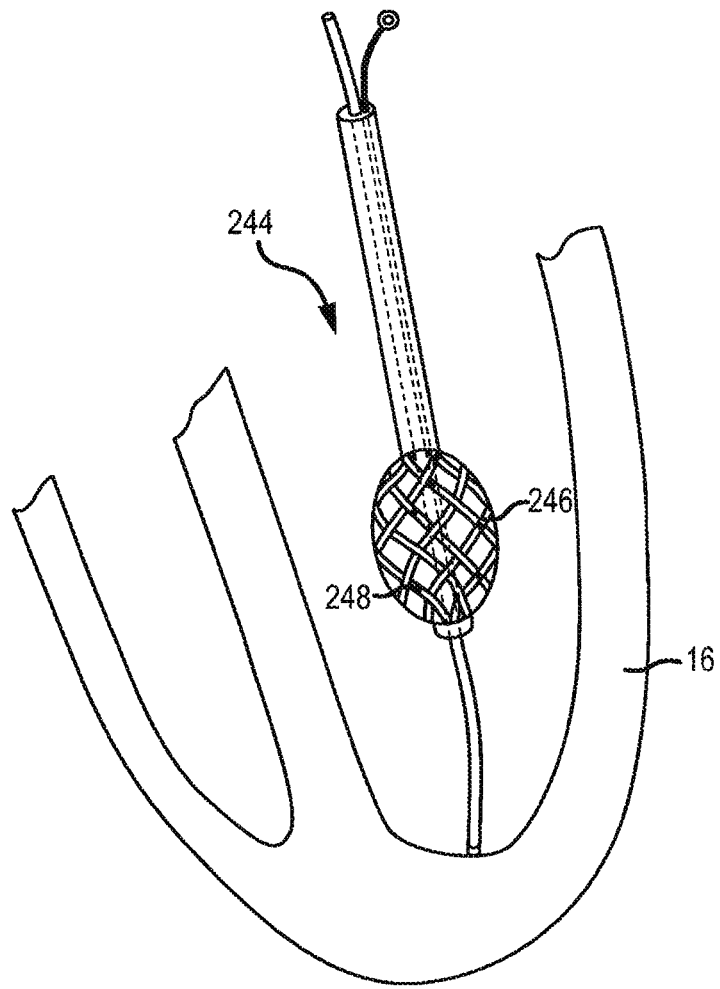
FIG. 29 is a diagrammatic view of a multi-electrode, array catheter illustrating one embodiment of a system in accordance with present teachings.

In addition to the above, the present invention may also find application in systems having multiple electrodes used for mapping the heart or other tissues, obtaining electrophysiological (EP) information about the heart or other tissues or ablating tissue. Referring to FIG. 29, one example of an EP catheter 244 is shown. The EP catheter 244 may be a non-contact mapping catheter such as the catheter sold by St. Jude Medical, Atrial Fibrillation Division, Inc. under the registered trademark "ENSITE ARRAY." Alternatively, the catheter 244 may comprise a contact mapping catheter in which measurements are taken through contact of the electrodes with the tissue surface. The catheter 244 includes a plurality of EP mapping electrodes 246. The electrodes 246 are placed within electrical fields created in the body 17 (e.g., within the heart). The electrodes 246 experience voltages that are dependent on the position of the electrodes 246 relative to the tissue 16. Voltage measurement comparisons made between the electrodes 246 can be used to determine the position of the electrodes 246 relative to the tissue 16. The electrodes 246 gather information regarding the geometry of the tissue 16 as well as EP data. For example, voltage levels on the tissue surface over time may be projected on an image or geometry of the tissue as an activation map. The voltage levels may be represented in various colors and the EP data may be animated to show the passage of electromagnetic waves over the tissue surface. Information received from the electrodes 246 can also be used to display the location and orientation of the electrodes 246 and/or the tip of the EP catheter 244 relative to the tissue 16. The electrodes 246 may be formed by removing insulation from the distal end of a plurality of braided, insulated wires 248 that are deformed by expansion (e.g., through use of a balloon) into a stable and reproducible geometric shape to fill a space (e.g., a portion of a heart chamber) after introduction into the space.

In the case of contact mapping catheters, the ECI can be used to determine which the electrodes 246 are in contact with or in close proximity to the tissue 16 so that only the most relevant information is used in mapping the tissue 16 or in deriving EP measurements or so that different data sets are more properly weighted in computations. As with the systems described hereinabove, the signal source 61 of the sensing circuit 26 may generate excitation signals across source connectors SOURCE (+) and SOURCE (−) defined between one or more electrodes 246 and the patch electrode 22. The impedance sensor 58 may then measure the resulting voltages across sense connectors SENSE (+) and SENSE (−)) defined between each electrode 246 and the patch electrode 20. The ECU 32 may then determine which the electrodes 246 have the highest impedance and/or ECI to determine the most relevant electrodes 246 for purposes of mapping or EP measurements. Similarly, in the case of a multiple electrode ablation catheter (not shown), the ECI can be used to determine which electrodes are in contact with the tissue 16 so that ablation energy is generated through only those electrodes, or can be used to adjust the power delivered to different electrodes to provide sufficient power to fully ablate the relevant tissue.

In either contact or non-contact mapping catheters, the multiple electrodes can provide a stable and highly accurate method of measuring changes in ECI over time, and thus can be used to determine the efficacy of an ablation. For example, the multiple electrodes 246 can each provide data for calculating an ECI value for that electrode. As an ablation catheter ablates tissue 16, the ECI values of the nearest electrodes will change dramatically, allowing the ECU 32 to calculate the location and efficacy of the lesion formed. The specific methods of calculating location will depend on the nature and shape of the mapping catheter, e.g., spherical, cylindrical, lariat, but may involve using LaPlace's equation and/or boundary element analysis as disclosed in U.S. Pat. No. 6,978,168 entitled "Software for Mapping Potential Distribution of a Heart Chamber," the disclosure of which is hereby incorporated herein by reference in its entirety.

The present invention also permits simultaneous measurements by multiple electrodes 246 on the catheter 244, or multiple measurements by a single electrode using multiple frequencies or duty cycles. Signals having distinct frequencies or multiplexed in time can be generated for each electrode 246. In one constructed embodiment, for example, signals with frequencies varying by 500 Hz around a 20 kHz frequency were used to obtain simultaneous distinct measurements from multiple electrodes 246. Because the distinct frequencies permit differentiation of the signals from each electrode 246, measurements can be taken for multiple electrodes 246 simultaneously thereby significantly reducing the time required for mapping and/or EP measurement procedures. Microelectronics permits precise synthesis of a number of frequencies and at precise quadrature phase offsets necessary for a compact implementation of current sources and sense signal processors. The extraction of information in this manner from a plurality of transmitted frequencies is well known in the field of communications as quadrature demodulation. Alternatively, multiple measurements can be accomplished essentially simultaneously by multiplexing across a number of electrodes with a single frequency for intervals of time less than necessary for a significant change to occur.

In accordance with another aspect of the invention, and as briefly described above, the system 10 may take the form of an automated catheter system 250, such as, for example and without limitation, a robotic catheter system or a magnetic-based catheter system. As will be described below, the automated catheter system 250 may be fully or partially automated, and so may allow for at least a measure of user control through a user input.

Figure 30:
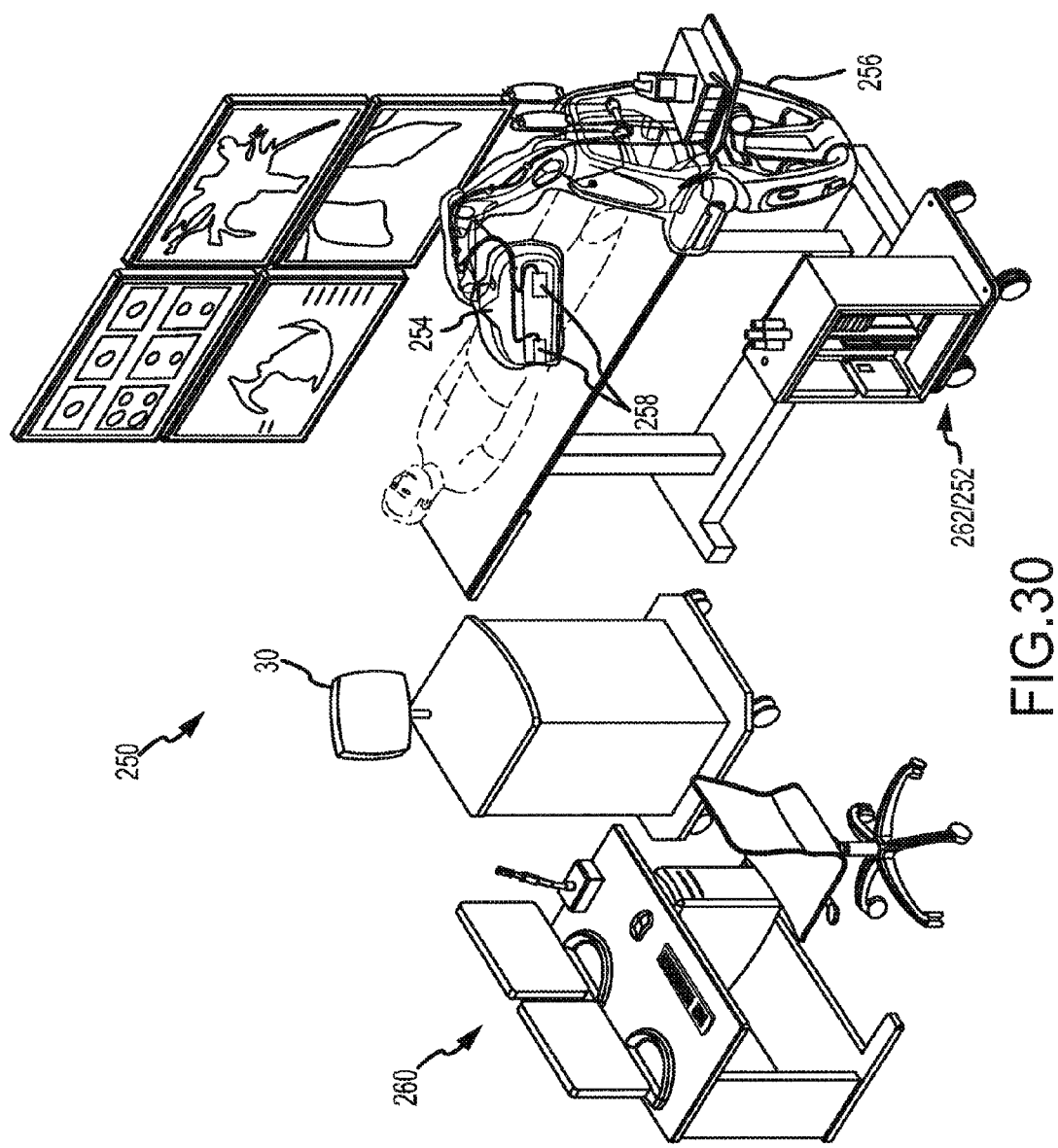
FIG. 30 is an isometric diagrammatic view of a robotic catheter system illustrating an exemplary layout of various system components in accordance with the present teachings.
Figure 31:
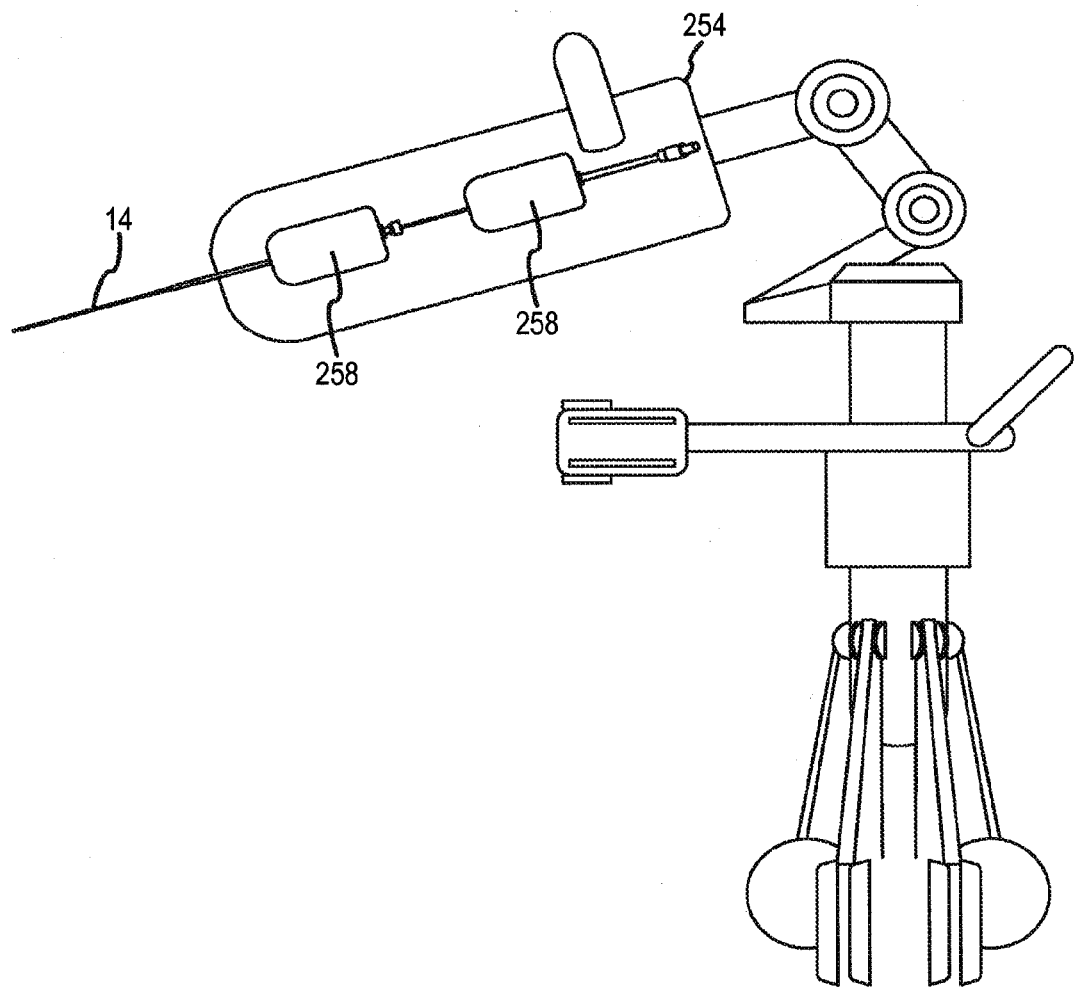
FIG. 31 is an isometric diagrammatic view of an exemplary embodiment of a robotic catheter manipulator support structure in accordance with the present teachings.

In the embodiment wherein the automated catheter system 250 is a robotic catheter system (i.e., robotic catheter system 250), a robot is used, for example, to control the movement of the catheter 14 and/or to carry out therapeutic, diagnostic, or other activities. In an exemplary embodiment, the robotic catheter system 250 may be configured such that information relating to contact sensing, proximity sensing, and/or lesion formation determined, for example, using the above-described calculated ECI, CECI, ALI, or other index or calculated indicator, may be communicated from the ECU 32 to a controller or control system 252 of the robotic catheter system 250. In an exemplary embodiment, the ECU 32 and the controller 252 are one in the same. However, in another exemplary embodiment, the two are separate and distinct components. For ease of description purposes only, the following description will be directed to the latter, separate and distinct arrangement. It should be noted, however, that the embodiment wherein the controller 250 and the ECU 32 are the same remains within the spirit and scope of the present invention. The information communicated to the controller 252 may be in the form of the signal(s) described above representative of an indicator relating to contact, proximity, and/or lesion formation. As will be described in greater detail below, the controller/control system 252 may use this information in the control and operation of the robotic catheter system 250. With reference to FIGS. 30 and 31, the robotic catheter system 250 will be briefly described. A full description of the robotic catheter system 250 is set forth in commonly-assigned and co-pending U.S. patent application Ser. No. 12/347,811 entitled "Robotic Catheter System," the disclosure of which is hereby incorporated by reference herein in its entirety.

Accordingly, FIGS. 30 and 31 illustrate the robotic catheter system 250. The robotic catheter system 250 provides the ability for precise and dynamic automated control in, for example, diagnostic, therapeutic, mapping, and ablative procedures. In an exemplary embodiment, the robotic catheter system 250 includes one or more robotic catheter manipulator assemblies 254 supported on a manipulator support structure 256. The robotic catheter manipulator assembly 254 may include one or more removably mounted robotic catheter device cartridges 258, for example, that are generally linearly movable relative to the robotic catheter manipulator assembly 254 to cause the catheter associated therewith (i.e., catheter 14) to be moved (e.g., advanced, retracted, etc.). The catheter manipulator assembly 254 serves as the mechanical control for the movements or actions of the cartridge 258. The robotic catheter system 250 may further include a human input device and control system ("input control system") 260, which may include a joystick and related controls with which a physician/clinician may interact to control the manipulation of the cartridge 258, and therefore, the catheter 14 of the system 250. The robotic catheter system 250 may still further include an electronic control system 262, which, in an exemplary embodiment, consists of or includes the controller 252, that translates motions of the physician/clinician at the input device into a resulting movement of the catheter. As with the system 10 described above, the robotic catheter system 250 may further include the visualization, mapping and navigation system 30, to provide the clinician/physician with real-time or near-real-time positioning information concerning the catheter and various types of anatomical maps, models, and/or geometries of the cardiac structure of interest, for example.

In addition to, or instead of, the manual control provided by the input control system 260, the robotic catheter system 250 may involve automated catheter movement. For example, in one exemplary embodiment, a physician/clinician may identify locations (potentially forming a path) on a rendered computer model of the cardiac structure. The system 250 can be configured to relate those digitally selected points to positions within the patient's actual/physical anatomy, and may command and control the movement of the catheter 14 to defined positions. Once in a defined position, either the physician/clinician or the system 250 could perform desired treatment or therapy, or perform diagnostic evaluations. The system 250 could enable full robotic control by using optimized path planning routines together with the visualization, mapping, and navigation system 30.

As briefly described above, in an exemplary embodiment, information relating to contact sensing, proximity sensing, and/or lesion formation is input into controller 252 and may be used in the control and operation of the robotic catheter system 250. In an exemplary embodiment, the information (e.g., ECI, CECI, ALI, etc.) is generated by, for example, the ECU 32 as described in great detail above. This information is then communicated by the ECU 32 to the controller 252. In one exemplary embodiment the information is simply stored within the robotic catheter system 250. Accordingly, no affirmative action is taken by the controller 252, or any other component of the robotic catheter system 250, in response to the information. In another exemplary embodiment, however, the information relating to contact, proximity, and/or lesion formation may be used by the robotic catheter system 250 to control one or more aspects of the operation of the system 250.

More particularly, in an exemplary embodiment, when it is determined, based on the calculated or determined index (e.g., ECI, ALI, CECI, etc.) described in great detail above, that the electrode 12 is in contact with the tissue 16, the controller 252 is configured to stop the movement of the catheter so as to prevent, or at least substantially reduce, the risk of the catheter pushing through, puncturing, or otherwise causing damage to the tissue. The controller 252 may also be configured to direct diagnostic or therapeutic activities once contact is sensed. For example, the controller 252 may be configured to initiate an ablative action once contact is sensed. In such an instance, the controller 252 would be connected to the ablation generator 24 either directly or indirectly through, for example, the ECU 32 to allow communication between the controller 252 and the ablation generator 24 to initiate ablative action.

Similarly, in another exemplary embodiment, when it is determined, based on the calculated or determined index (e.g., ECI, ALI, CECI, etc.) described in great detail above, that the electrode 12 is within a certain distance of the tissue 16 such that it is in close proximity to the tissue 16, the controller 252 may be configured to cause the movement of the catheter to stop, or to cause the speed at which the electrode 12 approaches the tissue 16 to be reduced. Conversely, the controller 252 may be further configured to cause the speed at which the catheter is travelling to increase if it is determined that the electrode 12 is a sufficient distance from the tissue 16. The controller 252 may be further configured to direct diagnostic or therapeutic activities depending on the sensed proximity of the electrode 12 to the tissue 16. As described above, in such an instance, the controller 252 would be connected to the ablation generator 24 either directly or indirectly through, for example, the ECU 32 to allow communication between the controller 252 and the ablation generator 24 to initiate ablative action.

Finally, in yet another exemplary embodiment, information relating to lesion formation may be used by the robotic catheter system 250 in a number of ways. For example, in one embodiment, the controller 252 may be configured to direct the catheter 14 to travel to a location where tissue was to be ablated, and then travel over the expected ablation site. More particularly, the controller 252 may be configured to control the movement of the catheter 14 to revisit an ablation site post-ablation and to cause the electrode 12 to travel along an ablation line or about an ablated area. This permits the system 250, as described in great detail above and using the calculated or determined index (e.g., ECI, ALI, CECI, etc.) also described in great detail above, to search for gaps in an ablation line or to determine whether tissue at an ablation site that should have been changed (e.g., ablated) was, in fact, changed (e.g., ablated). If unchanged/insufficiently changed (e.g., unablated or not fully ablated) tissue is found, the controller 252 may cause the catheter 14 to stop and inquire as to whether the tissue should be changed (e.g., ablated). This inquiry may be directed to a physician/clinician, the ECU 32, or another component of the system 250. If the answer is "yes," the controller 252 may be configured to direct the ablation generator 24 to initiate ablative action. In such an instance, the controller 252 would be connected to the ablation generator 24 either directly or indirectly through, for example, the ECU 32 to allow communication between the controller 252 and the ablation generator 24 to initiate ablative action. Alternatively, when unchanged/insufficiently changed (e.g., unablated or not fully ablated) tissue is found that the controller 252 knows should be changed (e.g., ablated), the controller 252 may cause the ablation generator 24 to initiate ablative action automatically and without inquiry.

In another exemplary embodiment, instead of or in addition to searching for unchanged/insufficiently changed (e.g., unablated or not fully ablated) tissue, the robotic control of the catheter movement may permit the system 250 to, as described in great detail above, assess the extent or quality of lesions formed in the tissue. If it is determined, based on the calculated or determined index (e.g., ECI, ALI, CECI, etc.) described in great detail above, that a particular area of tissue requires additional ablation, the controller 252 may cause the catheter to stop and inquire as to whether the tissue should be re-ablated. This inquiry may be directed to a physician/clinician the ECU 32, or another component within the system 250. If the answer is "yes," the controller 252 may be configured to direct the ablation generator 24 to initiate ablative action. In such an instance, the controller 252 would be connected to the ablation generator 24 either directly or indirectly through, for example, the ECU 32 to allow communication between the controller 252 and the ablation generator 24 to initiate ablative action. Alternatively, when tissue is found that requires additional ablation, the controller 252 may be configured to cause the ablation generator 24 to initiate ablative action automatically and without inquiry.

In another exemplary embodiment, rather than controlling the movement of the catheter 14 to search for unchanged/insufficiently changed (e.g., unablated or not fully ablated) tissue or to determine the quality of previous ablation, the controller 252 may be configured to direct the catheter to travel to a known location requiring ablation/re-ablation, and then directing the ablation generator 24 to initiate an ablative action once the desired location is reached. Alternatively, the controller 252 may be configured to move the catheter 14 to a desired location and then stop to allow for an inquiry to a physician/clinician, the ECU 32, or another component of system 250 to determine whether ablation should be initiated.

It should be noted that in each of the embodiments described above, the controller 252 may be configured to respond to a user input by a physician/clinician via the input control system 260, or may configured to carry out the processes described above in a fully or partially automated fashion requiring little or no user involvement.

Figure 32:
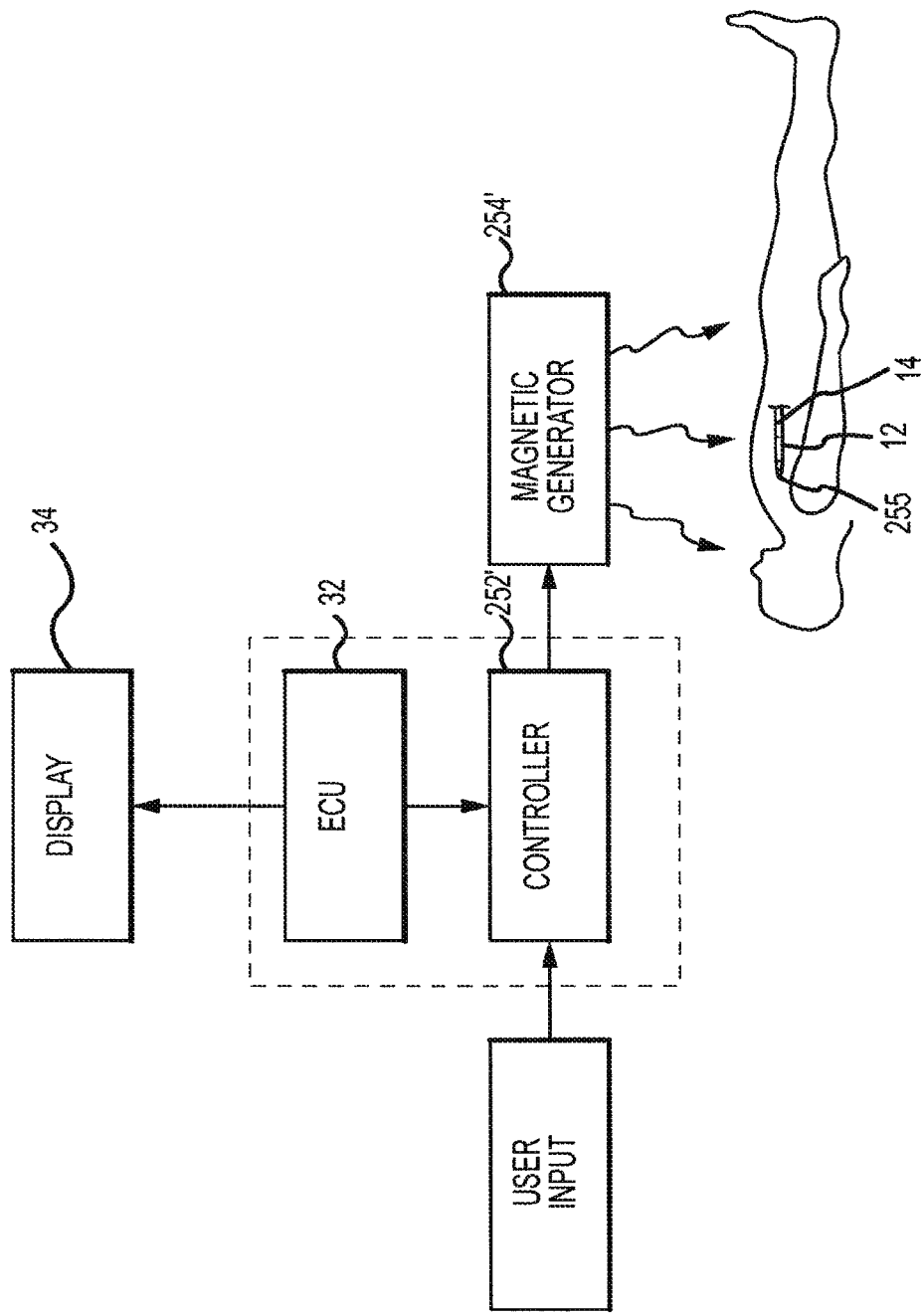
FIG. 32 is a schematic diagram of a magnetic-based catheter manipulation system in accordance with the present teachings.

With reference to FIG. 32, an exemplary embodiment of the automated catheter guidance system 250 comprising a magnetic-based catheter system (i.e., magnetic-based catheter system 250') is illustrated. In one exemplary embodiment, one or more externally generated magnetic fields produced by one or more electromagnets are used to move, guide, and/or steer a magnetically-tipped catheter through a patient's body. The externally generated magnetic fields exert a desired torque on the catheter to cause the position of the catheter to be manipulated in a desired way (e.g., advance, retract, bend, rotate, speed up, slow down, etc.). Accordingly, as with the robotic catheter system described above, the magnetic fields may be used to control the movement of the catheter 14 and/or to allow the system 10 to carry out therapeutic, diagnostic, or other activities at given locations within the patient's body. A full description of a magnetic-based catheter system is set forth in U.S. Pat. No. 6,507,751 entitled "Method and Apparatus Using Shaped Field of Repositionable Magnet to Guide Implant," and U.S. Published Patent Application No. 2007/0016006 A1 entitled "Apparatus and Method for Shaped Magnetic Field Control for Catheter, Guidance, Control, and Imaging," the disclosures of which are hereby incorporated by reference herein in their entireties.

In an exemplary embodiment, the magnetic-based catheter system 250' may be configured such that information relating to contact sensing, proximity sensing, and/or lesion formation determined, for example, using the above-described calculated ECI, CECI, ALI, or other index or calculated indicator, may be communicated from the ECU 32 to a controller or control system 252' of the magnetic-based catheter system 250'. In an exemplary embodiment, the ECU 32 and the controller 252' are one in the same. However, in another exemplary embodiment, the two are separate and distinct components. For ease of description purposes only, the following description will be directed to the latter, separate and distinct arrangement. It should be noted, however, that the embodiment wherein the controller 250' and the ECU 32 are the same remains within the spirit and scope of the present invention. The information communicated to the controller 252' may be in the form of the signal(s) described above representative of an indicator relating to contact, proximity, and/or lesion formation. As will be described in greater detail below, the controller/control system 252' may use this information in the control and operation of the magnetic-based catheter system 250'.

As with the robotic catheter system described above, the magnetic-based catheter system 250' provides the ability for precise and dynamic automated control in, for example, diagnostic, therapeutic, mapping, and ablative procedures. In an exemplary embodiment, the magnetic-based catheter system 250' includes somewhat similar structure to that of the robotic catheter system described above to effect the movement of the catheter 14. For example, system 250' may comprise a catheter manipulator assembly 254' that includes, in part, one or more external magnetic field generators configured to create the magnetic field(s) required to induce the movement of the catheter 14, and a magnetic element 255 mounted thereon or therein. The system 250' may further comprise support structures and the like to support catheter 14. As also with the robotic catheter system, the magnetic-based catheter system 250' may further include a human input device and control system ("input control system"), which may include a joystick and related controls with which a physician/clinician may interact to control the manipulation the catheter 14. In one exemplary embodiment, the system 250' is configured such that the physician or clinician may input a command for the catheter to move in a particular way. The system 250' processes that input and adjusts the strength and/or orientation of the external magnetic fields to cause the catheter 14 to move as commanded. The magnetic-based catheter system 250' may also still further include an electronic control system, which, as with the electronic control system of the robotic catheter system described above, may consist of or include the controller 252', that translates motions of the physician/clinician at the input device into a resulting movement of the catheter. Finally, in an exemplary embodiment, the magnetic-based catheter system 250' may further include the visualization, mapping and navigation system 30, to provide the clinician/physician with real-time or near-real-time positioning information concerning the catheter and various types of anatomical maps, models, and/or geometries of the cardiac structure of interest, for example.

As briefly described above, in an exemplary embodiment, information relating to contact sensing, proximity sensing, and/or lesion formation is input into controller 252' and may be used in the control and operation of the magnetic-based catheter system 250'. In an exemplary embodiment, the information (e.g., ECI, CECI, ALI, etc.) is generated by, for example, the ECU 32 as described in great detail above. This information is then communicated by the ECU 32 to the controller 252'. In one exemplary embodiment the information is simply stored within the magnetic-based catheter system 250'. Accordingly, no affirmative action is taken by the controller 252', or any other component of the magnetic-based catheter system 250', in response to the information. In another exemplary embodiment, however, the information relating to contact, proximity, and/or lesion formation may be used by the magnetic-based catheter system 250' to control one or more aspects of the operation of the system 250'.

More particularly, in an exemplary embodiment, when it is determined, based on the calculated or determined index (e.g., ECI, ALI, CECI, etc.) described in great detail above, that the electrode 12 is in contact with the tissue 16, the controller 252' is configured to stop the movement of the catheter so as to prevent, or at least substantially reduce, the risk of the catheter pushing through, puncturing, or otherwise causing damage to the tissue. Accordingly, the controller 252' is configured to adjust the external magnetic field to cause the catheter 14 to stop moving. The controller 252' may also be configured to direct diagnostic or therapeutic activities once contact is sensed. For example, the controller 252' may be configured to initiate an ablative action once contact is sensed. In such an instance, the controller 252' would be connected to the ablation generator 24 either directly or indirectly through, for example, the ECU 32 to allow communication between the controller 252' and the ablation generator 24 to initiate ablative action.

Similarly, in another exemplary embodiment, when it is determined, based on the calculated or determined index (e.g., ECI, ALI, CECI, etc.) described in great detail above, that the electrode 12 is within a certain distance of the tissue 16 such that it is in close proximity to the tissue 16, the controller 252' may be configured to cause the movement of the catheter to stop, or to cause the speed at which the electrode 12 approaches the tissue 16 to be reduced, by adjusting the strength and/or orientation of the external magnetic field. Conversely, the controller 252' may be further configured to cause the speed at which the catheter is travelling to increase if it is determined that the electrode 12 is a sufficient distance from the tissue 16. The controller 252' may be further configured to direct diagnostic or therapeutic activities depending on the sensed proximity of the electrode 12 to the tissue 16. As described above, in such an instance, the controller 252' would be connected to the ablation generator 24 either directly or indirectly through, for example, the ECU 32 to allow communication between the controller 252' and the ablation generator 24 to initiate ablative action.

Finally, in yet another exemplary embodiment, information relating to lesion formation may be used by the magnetic-based catheter system 250' in a number of ways. For example, in one embodiment, the controller 252' may be configured to direct the catheter 14 to travel to a location where tissue was to be ablated, and then travel over the expected ablation site. More particularly, the controller 252' may be configured to control the external magnetic field to cause the catheter 14 to revisit an ablation site post-ablation and to cause the electrode 12 to travel along an ablation line or about an ablated area. This permits the system 250', as described in great detail above and using the calculated or determined index (e.g., ECI, ALI, CECI, etc.) also described in great detail above, to search for gaps in an ablation line or to determine whether tissue at an ablation site that should have been changed (e.g., ablated) was, in fact, changed (e.g., ablated). If unchanged/insufficiently changed (e.g., unablated or not fully ablated) tissue is found, the controller 252' may cause the catheter 14 to stop and inquire as to whether the tissue should be changed (e.g., ablated). This inquiry may be directed to a physician/clinician, the ECU 32, or another component of the system 250'. If the answer is "yes," the controller 252' may be configured to direct the ablation generator 24 to initiate ablative action. In such an instance, the controller 252' would be connected to the ablation generator 24 either directly or indirectly through, for example, the ECU 32 to allow communication between the controller 252' and the ablation generator 24 to initiate ablative action. Alternatively, when unchanged/insufficiently changed (e.g., unablated or not fully ablated) tissue is found that the controller 252' knows should be changed (e.g., ablated), the controller 252' may cause the ablation generator 24 to initiate ablative action automatically and without inquiry.

In another exemplary embodiment, instead of or in addition to searching for unchanged/insufficiently changed (e.g., unablated or not fully ablated) tissue, the control of the catheter movement may permit the system 250' to, as described in great detail above, assess the extent or quality of lesions formed in the tissue. If it is determined, based on the calculated or determined index (e.g., ECI, ALI, CECI, etc.) described in great detail above, that a particular area of tissue requires additional ablation, the controller 252' may cause the catheter to stop and inquire as to whether the tissue should be re-ablated. This inquiry may be directed to a physician/clinician the ECU 32, or another component within the system 250'. If the answer is "yes," the controller 252' may be configured to direct the ablation generator 24 to initiate ablative action. In such an instance, the controller 252' would be connected to the ablation generator 24 either directly or indirectly through, for example, the ECU 32 to allow communication between the controller 252' and the ablation generator 24 to initiate ablative action. Alternatively, when tissue is found that requires additional ablation, the controller 252' may be configured to cause the ablation generator 24 to initiate ablative action automatically and without inquiry.

In another exemplary embodiment, rather than controlling the movement of the catheter 14 to search for unchanged/insufficiently changed (e.g., unablated or not fully ablated) tissue or to determine the quality or extent of a previous ablation, the controller 252' may be configured to direct the catheter to travel to a known location requiring ablation/re-ablation, and then directing the ablation generator 24 to initiate an ablative action once the desired location is reached. Alternatively, the controller 252' may be configured to move the catheter 14 to a desired location and then stop to allow for an inquiry to a physician/clinician, the ECU 32, or another component of system 250' to determine whether ablation should be initiated.

It should be noted that in each of the embodiments described above, the controller 252' may be configured to respond to a user input by a physician/clinician via the input control system, or may configured to carry out the processes described above in a fully or partially automated fashion requiring little or no user involvement.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:
1. A guidance system for a catheter, comprising:
   an electronic control unit (ECU) configured to:
      analyze first and second components of a complex impedance between an electrode and tissue;
      analyze a state of contact between the electrode and the tissue;
      determine location coordinates of the electrode over a period of time to analyze a stability of the electrode location; and
      assess lesion formation in at least one site on the tissue according to the first and second complex impedance components, according to the state of contact, and according to the stability of the electrode location; and a display device, electrically coupled with said ECU, configured to provide feedback to a user for manipulating the catheter according to said lesion formation assessment.

2. The guidance system of claim 1, wherein the state of contact comprises one or more of a contact pressure, a contact force, a temperature, a change in temperature, and a fluid flow rate.

3. The guidance system of claim 1, wherein said ECU is configured to assess lesion formation by calculating an index responsive to at least the first and second complex impedance components and to the state of contact.

4. The guidance system of claim 3, wherein said ECU is configured to assess lesion formation by calculating an index rate by:
receiving a first set of said location coordinates corresponding to a first location of the electrode and a second set of said location coordinates corresponding to a second location of the electrode;
calculating an index change between a first index calculated responsive to first and second components of a first complex impedance acquired while the electrode is located at the first location and a second index calculated responsive to first and second components of a second complex impedance acquired while the electrode is located at the second location over a predetermined time interval;
calculating a change in the first and second sets of location coordinates; and
calculating an index rate by dividing the index change by the change in the first and second sets of location coordinates.

5. The guidance system of claim 4, wherein said ECU is configured to assess lesion formation by comparing the index rate to one or more thresholds.

6. The guidance system of claim 3, wherein the index is responsive to at least the first and second complex impedance components, a temperature, and a contact force.

7. The guidance system of claim 6, wherein the index is additionally responsive to a measure of trabeculation.

8. The guidance system of claim 3, wherein said ECU is configured to assess lesion formation by comparing the index to one or more thresholds.

9. The guidance system of claim 1, wherein assessing lesion formation comprises determining whether a change in the complex impedance is due to a change in the state of contact or a change in the tissue.

10. A system for generating an electroanatomical map, comprising:
an electronic control unit (ECU) configured to:
analyze first and second components of a complex impedance between an electrode and tissue;
analyze a state of contact between the electrode and the tissue;
determine location coordinates of the electrode over a period of time to analyze a stability of the electrode location;
assess lesion formation in at least one site on the tissue based on the complex impedance values, the contact state, and the stability of the electrode location; and
generate an electroanatomical map containing a plurality of assessed lesion sites; and
a display device, electrically coupled with said ECU, configured to display respective tissue characteristics associated with each of the plurality of assessed lesion sites.

11. The system of claim 10, wherein the state of contact comprises one or more of a contact pressure, a contact force, a temperature, a change in temperature, and a fluid flow rate.

12. The system of claim 10, wherein said ECU is configured to assess lesion formation by calculating an index responsive to at least the first and second complex impedance components and to the state of contact.

13. The system of claim 10, wherein said ECU is configured to assess lesion formation by calculating an index rate by:
receiving a first set of said location coordinates corresponding to a first location of the electrode and a second set of said location coordinates corresponding to a second location of the electrode;
calculating an index change between a first index calculated responsive to first and second components of a first complex impedance acquired while the electrode is located at the first location and a second index calculated responsive to first and second components of a second complex impedance acquired while the electrode is located at the second location over a predetermined time interval;
calculating a change in the first and second sets of location coordinates; and
calculating an index rate by dividing the index change by the change in the first and second sets of location coordinates.

14. The system of claim 13, wherein said ECU is configured to assess lesion formation by comparing the index rate to one or more thresholds.

15. The system of claim 12, wherein the index is responsive to at least the first and second complex impedance components, a temperature, and a contact force.

16. The system of claim 15, wherein the index is additionally responsive to a measure of trabeculation.

17. The system of claim 12, wherein said ECU is configured to assess lesion formation by comparing the index to one or more thresholds.

18. The system of claim 10, wherein the respective tissue characteristics are placed on the electroanatomical map.

19. The system of claim 10, wherein assessing lesion formation comprises determining whether a change in the complex impedance is due to a change in the state of contact or a change in the tissue.

* * * * *